(12) United States Patent
Adams et al.

(10) Patent No.: US 7,230,004 B2
(45) Date of Patent: Jun. 12, 2007

(54) CYCLOPAMINE ANALOGUES AND METHODS OF USE THEREOF

(75) Inventors: Julian Adams, Boston, MA (US); Alfredo C. Castro, Winchester, MA (US); Michael A. Foley, Chestnut Hill, MA (US); Somarajan Nair Janardanan Nair, Belmont, MA (US); Marta Nevalainen, Quincy, MA (US); James R. Porter, Brighton, MA (US); Martin R. Tremblay, Melrose, MA (US)

(73) Assignee: Infinity Discovery, Inc., Cambridge, MA (US)

( * ) Notice: Subject to any disclaimer, the term of this patent is extended or adjusted under 35 U.S.C. 154(b) by 60 days.

(21) Appl. No.: 11/213,534

(22) Filed: Aug. 26, 2005

(65) Prior Publication Data

US 2006/0074030 A1    Apr. 6, 2006

Related U.S. Application Data

(60) Provisional application No. 60/683,169, filed on May 19, 2005, provisional application No. 60/625,676, filed on Nov. 5, 2004, provisional application No. 60/617,170, filed on Oct. 8, 2004, provisional application No. 60/605,020, filed on Aug. 27, 2004.

(51) Int. Cl.
*A61K 31/438* (2006.01)
*A61K 31/4355* (2006.01)
*C07D 491/10* (2006.01)
*C07D 491/048* (2006.01)

(52) U.S. Cl. .................. 514/278; 546/18; 546/15
(58) Field of Classification Search ............... 514/278; 546/18, 15
See application file for complete search history.

(56) References Cited

U.S. PATENT DOCUMENTS 6,238,876 B1    5/2001    Altaba

| 6,291,516 B1 | 9/2001 | Dudek et al. |
| 6,432,970 B2 | 8/2002 | Beachy et al. |
| 2004/0072913 A1 | 4/2004 | Tas et al. |

FOREIGN PATENT DOCUMENTS

| WO | WO-95/18856 | 7/1995 |
| WO | WO-96/17924 | 6/1996 |
| WO | WO-01/27135 | 4/2001 |
| WO | WO-02/30462 | 4/2002 |
| WO | WO-2005/013800 | 2/2005 |
| WO | WO-2005/032343 | 4/2005 |
| WO | WO-2005/042700 | 5/2005 |

OTHER PUBLICATIONS

Alexandre et al., Genes Dev. (1996) 10:2003-2013.
Belloni et al., Nature Genetics (1996) 14:353-356.
Berman et al., Nature (2003) 425:846-851.
Chen et al., Genes and Development (2002) 16:2743-2748.
Cooper et al., Science (1998) 280:1603-1607.
Fan et al., Endocrinology (2004) 145:3961-3970.
Karhadkar et al., Nature (2004) 431:707-712.
Kubo et al., Cancer Research (2004) 64:6071-6074.
Lewis et al., Journal of Mammary Gland Biology and Neoplasia (2004) 2:165-181.
Quirk et al., Cold Spring Harbor Symp. Quant. Biol. (1997) 62:217-226.
Reifenberger et al., Cancer Res. (1998) 58:1798-1803.
Sheng et al., Molecular Cancer (2004) 3:29-42.
Tas et al., Dermatology (2004) 209:126-131.
Thayer et al., Nature (2003) 425:851-856.
Watkins et al., Nature (2003) 422:313-317.
Xie et al., Nature (1998) 391:90-92.
International Search for PCT/US05/30406, mailed on Apr. 4, 2006, 2 pages.

*Primary Examiner*—Charanjit S. Aulakh
(74) *Attorney, Agent, or Firm*—Morrison & Foerster LLP

(57) ABSTRACT

The present invention provides compositions and methods for modulating smoothened-dependent pathway activation. The present invention provides analogs of cyclopamine that can be used to counteract the phenotypic effects of unwanted activation of a hedgehog pathway, such as resulting from hedgehog gain-of-function, Ptc loss-of-function or smoothened gain-of-function mutations. The compounds of the present invention are particularly useful in treating cancers.

39 Claims, No Drawings

CYCLOPAMINE ANALOGUES AND METHODS OF USE THEREOF

RELATED APPLICATION

This application claims benefit of the following U.S. applications: Ser. No. 60/605,020 filed Aug. 27, 2004, Ser. No. 60/617,170 filed Oct. 8, 2004, Ser. No. 60/625,676 filed Nov. 5, 2004, and Ser. No. 60/683,169 filed May 19, 2005, each of which is incorporated herein by reference in their entirety.

BACKGROUND OF THE INVENTION

The hedgehog signaling pathway is essential for numerous processes during embryonic development. Members of the hedgehog family of secreted proteins control cell proliferation, differentiation and tissue patterning. The pathway was first deciphered in the fruit fly Drosophila, but since has been shown to be highly conserved in invertebrates and vertebrates, including humans. The overall activity of the hedgehog signaling pathway declines after embryogenesis in most cells, but the pathway remains active in certain adult cell types. Recently, it has been shown that uncontrolled activation of the hedgehog pathway results in certain types of cancer as detailed below.

The Hedgehog polypeptide is a secreted protein that functions as a signaling ligand in the hedgehog pathway. Exemplary hedgehog genes and proteins are described in PCT publications WO 95/18856 and WO 96/17924. Three different forms of the hedgehog protein are found in humans; Sonic hedgehog (Shh), Desert hedgehog (Dhh) and Indian hedgehog (Ihh). Sonic hedgehog is the most prevalent hedgehog member in mammals and also is the best characterized ligand of the hedgehog family. Prior to secretion, Shh undergoes an intramolecular cleavage and lipid modification reaction. The lipid modified peptide is responsible for all signaling activities Two transmembrane proteins are involved in signal transduction of in the hedgehog pathway; the twelve-transmembrane Patched receptor (Ptc) and the seven-transmembrane Smoothened protein (Smo).

The findings in the art suggest that Hedgehog acts by binding to Ptc, thereby releasing an inhibitory effect of Ptc on Smo. Since Ptc and Smo are both transmembrane proteins, a proposed scenario is that they physically associate to form a receptor complex, though indirect mechanisms of action are also plausible. The derepression of Smo from Ptc inhibition most likely involves a conformational change in Smo. Ptc, however, is not essential for Smo's activity, since Smo becomes constitutively activated in the complete absence of Patched protein (Alcedo et al., supra; Quirk et al. (1997) Cold Spring Harbor Symp. Quant. Biol. 62: 217–226). Once Smo is derepressed it is rapidly and highly phosphorylated and transduces a signal that activates transcription via the Gli transcription factors (homologue of Dropophila Ci protein) (Alexandre et al. (1996) Genes Dev. 10: 2003–13)). The Gli1 transcription factor up-regulates many genes involved in growth and development (Alexandre et al., supra). Hedgehog signaling is essential in many stages of development, especially in formation of left-right symmetry. Loss or reduction of hedgehog signaling leads to multiple developmental deficits and malformations, one of the most striking of which is cyclopia (Belloni et al. (1996) Nature Genetics 14: 353–6).

Recently, it has been reported that activating hedgehog pathway mutations occur in sporadic basal cell carcinoma (Xie et al. (1998) Nature 391: 90–2) and primitive neuroectodermal tumors of the central nervous system (Reifenberger et al. (1998) Cancer Res 58: 1798–803). Uncontrolled activation of the hedgehog pathway has also been shown in numerous cancer types such as GI tract cancers including pancreatic, esophageal, gastric cancer (Berman et al. (2003) Nature 425: 846–51, Thayer et al. (2003) Nature 425: 851–56) lung cancer (Watkins et al. (2003) Nature 422: 313–317, prostate cancer (Karhadkar et al (2004) Nature 431: 707–12, Sheng et al. (2004) Molecular Cancer 3: 29–42, Fan et al. (2004) Endocrinology 145: 3961–70), breast cancer (Kubo et al. (2004) Cancer Research 64: 6071–74, Lewis et al. (2004) Journal of Mammary Gland Biology and Neoplasia 2: 165–181) and hepatocellular cancer (Sicklick et al. (2005) ASCO conference, Mohini et al. (2005) AACR conference).

Small molecule inhibition of hedgehog pathway activity has been shown to result in cell death in a number of different cancer types having uncontrolled hedgehog pathway activation (See, for example, Berman et al., 2003 Nature 425: 846–51).

Hedgehog pathway antagonists are currently being explored in a large number of clinical conditions where a therapeutic effect can be obtained for a condition or disorder by inhibiting one or more aspects of Hedgehog pathway activity. Although the primary focus has been on cancer, investigators have found that small molecule inhibition of the hedgehog pathway has been shown to ameliorate the symptoms of psoriasis (Tas, et al., 2004 Dermatology 209: 126–131, published US patent application 20040072913 (herein incorporated by reference)). Psoriasis is a very common, chronic skin disorder typically characterized by skin lesions usually containing erythematous papules and plaques with a silver scale, although there are variations both on the skin and in other parts of the body. Psoriasis is currently thought to be an autoimmune disease but its etiology is still poorly understood.

A hedgehog pathway inhibitor that has attracted considerable interest is the natural product cyclopamine. Cyclopamine was first isolated from the lily Veratrum californicum in 1966 after it was found that the offspring of grazing sheep were born with severe birth deformities. In an effort to identify the agent(s) responsible for causing these birth deformities, the FDA investigated possible sources of tetragens and identified the jervine family of steroidal alkaloids, including the compound cyclopamine, as the tetragens responsible for the birth deformities.

Much later, it was found that cyclopamine's mechanism of action was through the inhibition of hedgehog pathway activity (Cooper et al. (1998) Science 280: 1603–7, Chen et al., (2002) Genes and Development 16: 2743–8). Cyclopamine and related compounds have been shown to have anticancer activities through action on the hedgehog pathway. Despite initial promise, no members of this family of compounds, or analogues thereof, have been successfully developed as an anticancer agent. The present invention fulfills this need and has other related advantages.

SUMMARY OF THE INVENTION

The present invention provides analogs of steroidal alkaloids of the cyclopamine family that are useful for inhibiting proliferation of cells and/or promoting apoptosis in a cell, such as in the treatment of proliferative disorders such as cancers. The hedgehog pathway antagonists of the present invention may be used to inhibit proliferation (or other biological consequences) of cells or tissues, such as in a patient, characterized as having a Ptc loss-of-function phenotype, a Smo gain-of-function phenotype or a Hedgehog gain-of-function phenotype.

In certain uses, the present methods are used to counteract the phenotypic effects of unwanted activation of a Hedgehog pathway, such as resulting from hedgehog gain-of-function, Ptc loss-of-function or Smo gain-of-function mutations. For instance, the present methods can involve contacting a cell (in vitro or in vivo) with a hedgehog pathway antagonist of the present invention (defined below) in an amount sufficient to antagonize Smo-dependent pathway activation. Such antagonism will stop or slow unwanted cell proliferation and can lead to cell death.

In certain embodiments, the methods and compounds of the present invention may be used to regulate proliferation of cells and/or cell death in vitro and/or in vivo such as in the treatment of malignant disorders of the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain.

In certain embodiments, the methods and compounds of the present invention may be used to treat the symptoms of psoriasis in a subject. The compounds of the present invention may be used to treat psoriasis as a single agent or in combination with one or more anti-psoriasis agents. In particular embodiments, the compounds of the present invention are topically administered to a subject in need thereof.

The compounds of the present invention may be further formulated as a pharmaceutical preparation comprising a pharmaceutically acceptable excipient, for administration to a patient as a means of treating cancer. The hedgehog pathway antagonists of the present invention and/or preparations comprising them may be administered to a patient to treat conditions involving unwanted cell proliferation, e.g., cancer and/or tumors of the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain. In certain embodiments, such compounds or preparations are administered systemically, e.g. parenterally and/or locally, e.g., topically.

DETAILED DESCRIPTION OF THE INVENTION

Definitions

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. Alkyl groups, unless otherwise specified, may optionally be substituted with suitable substituents. The number of substituents is typically limited by the number of available valences on the alkyl group; thus an alkyl group may be substituted by replacement of one or more of the hydrogen atoms that would be present on the unsubstituted group. suitable substituents for alkyl groups include halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, $C_1$–$C_6$ alkyl, $C_2$–$C_6$ heteroalkyl, $C_1$–$C_6$ acyl, $C_2$–$C_6$ heteroacyl, $C_6$–$C_{10}$ aryl, $C_5$–$C_{10}$ heteroaryl, $C_7$–$C_{12}$ arylalkyl, or $C_6$–$C_{12}$ heteroarylalkyl, each of which is optionally substituted with one or more groups selected from halo, $C_1$–$C_4$ alkyl, $C_1$–$C_4$ heteroalkyl, $C_1$–$C_6$ acyl, $C_1$–$C_6$ heteroacyl, hydroxy, amino, and =O; and wherein two R' on the same substituent or on adjacent atoms can be linked to form a 3–7 membered ring optionally containing up to three heteroatoms selected from N, O and S;

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively and may contain a mixture of both double and triple bonds. Alkenyl and alkynyl groups are also optionally substituted unless otherwise specified, by the same substituents described above for alkyl groups.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1–3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a sulfonyl group.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine", "amino" and "ammonium" are art-recognized and refer to both unsubstituted and substituted amines, e.g., a moiety that may be represented by the general formulas:

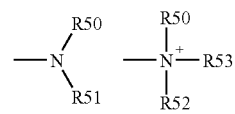

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

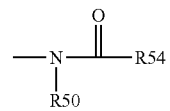

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

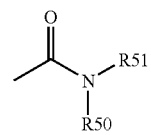

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

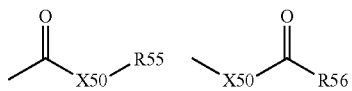

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

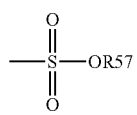

in which R57 is an electron pair, hydrogen, alkyl, cycloalkyl, or aryl.

The term "sulfate" is art recognized and includes a moiety that may be represented by the general formula:

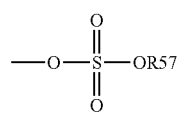

in which R57 is as defined above.

The term "sulfonamido" is art recognized and includes a moiety that may be represented by the general formula:

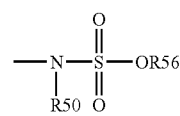

in which R50 and R56 are as defined above.

The term "sulfamoyl" is art-recognized and refers to a moiety that may be represented by the general formula:

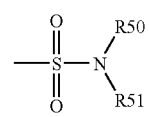

in which R50 and R51 are as defined above.

The term "sulfonyl" is art-recognized and refers to a moiety that may be represented by the general formula:

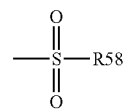

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

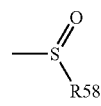

in which R58 is defined above.

The term "phosphoryl" is art-recognized and may in general be represented by the formula:

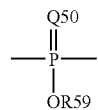

wherein Q50 represents S or O, and R59 represents hydrogen, a lower alkyl or an aryl. When used to substitute, e.g., an alkyl, the phosphoryl group of the phosphorylalkyl may be represented by the general formulas:

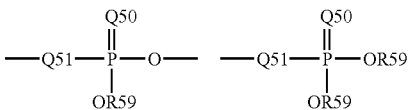

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

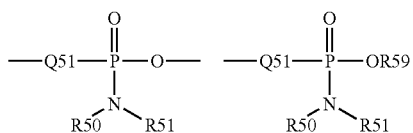

wherein Q51, R50, R51 and R59 are as defined above.

The term "phosphonamidite" is art-recognized and may be represented in the general formulas:

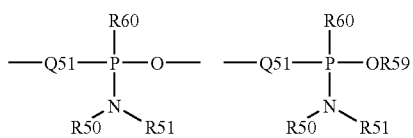

wherein Q51, R50, R51 and R59 are as defined above, and $R^{60}$ represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. Similarly, a particular enantiomer in a racemic mixture can be separated from it's enantiomer via chiral chromatographic methods known in the art.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, $2^{nd}$* ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics,* 67th Ed., 1986–87, inside cover.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as nonwild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of non-melanoma skin cancers fall into this category.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potential for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements.

Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The term "ED50" means the dose of a drug which produces 50% of its maximum response or effect.

An "effective amount" of a subject compound, with respect to the present methods of treatment, refers to an amount of the antagonist in a preparation which, when applied as part of a desired dosage regimen brings about, e.g., a change in the rate of cell proliferation and/or rate of survival of a cell according to clinically acceptable standards for the disorder to be treated.

The terms "epithelia", "epithelial" and "epithelium" refer to the cellular covering of internal and external body surfaces (cutaneous, mucous and serous), including the glands and other structures derived therefrom, e.g., corneal, esophogeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hedgehog pathway antagonist" refers to an agent that inhibits the function of the hedgehog pathway, e.g. represses transcription of target genes (Gli1 and Ptc genes), which in normal cells are induced by contact of the cell with hedgehog. In addition to altering a smoothened dependent pathway, in certain embodiments the hedgehog pathway antagonists of the current invention can be used to overcome a Ptc loss-of-function, smoothened gain-of-function, and/or a hedgehog gain-of-function. The terms "loss-of-function" and "gain-of-function", as appropriate, refer to an aberrant modification or mutation of, e.g., a Ptc gene, hedgehog gene, or smoothened gene, or a decrease or increase in the level of expression of such a gene, which results in a phenotype, e.g., which resembles contacting a cell with a hedgehog protein, such as aberrant activation of a hedgehog pathway or resemble loss of Smo function. The mutation may include a loss of the ability of the Ptc or Smo gene product (s) to regulate the level of activity of Gli/Ci proteins, e.g., Gli1, Gli2, and Gli3.

As used herein, "immortalized cells" refers to cells which have been altered via chemical and/or recombinant means such that the cells have the ability to grow through an indefinite number of divisions in culture.

The term "LD50" means the dose of a drug which is lethal in 50% of test subjects.

A "patient" or "subject" to be treated by the present method can mean either a human or non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity (or other physiological activity) of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

The term "therapeutic index" refers to the therapeutic index of a drug defined as LD50/ED50.

The term "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "subject" as used herein, refers to an animal, typically a mammal or a human, that has been the object of treatment, observation, and/or experiment. When the term is used in conjunction with administration of a compound or drug, then the subject has been the object of treatment, observation, and/or administration of the compound or drug. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly to the site of hedgehog pathway mediated disorder, such that it enters the patient's system and, thus, is subject to metabolism and other like processes, for example, subcutaneous administration.

The term 'sugar' as used herein refers to a natural or an unnatural monosaccharide, disaccharide or oligosaccharide comprising one or more pyranose or furanose rings. The sugar may be covalently bonded to the steroidal alkaloid of the present invention through an ether linkage or through an alkyl linkage. In certain embodiments the saccharide moiety may be covalently bonded to a steroidal alkaloid of the present invention at an anomeric center of a saccharide ring.

The term "diradical" as used herein refers to any of a series of divalent groups from alkyl, alkenyl, alkynyl, aryl, cycloalkyl, heterocycloalkyl, aralkyl, heteroaryl, and heteroaralkyl groups. For example,

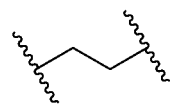

is an alkyl diradical;

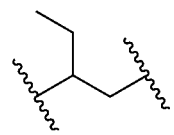

is also an alkyl diradical;

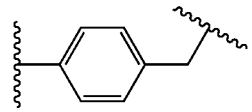

is an aralkyl diradical; and

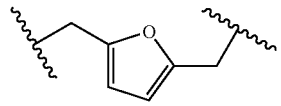

is an (alkyl)heteroaralkyl diradical. Typical examples include alkylenes of general structure $(CH_2)_x$ where X is 1–6, and corresponding alkenylene and alkynylene linkers having 2–6 carbon atoms and one or more double or triple bonds; cycloalkylene groups having 3–8 ring members; and aralkyl groups wherein one open valence is on the aryl ring and one is on the alkyl portion such as

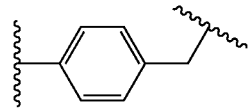

and its isomers.

Compounds of the Invention

The present invention provides analogs of cyclopamine as well as isolated and purified forms thereof, including synthetic and semisynthetic analogs, as well as pharmaceutical compositions containing such analogs. In one embodiment, the present invention provides compounds represented by a compound of Formula 1:

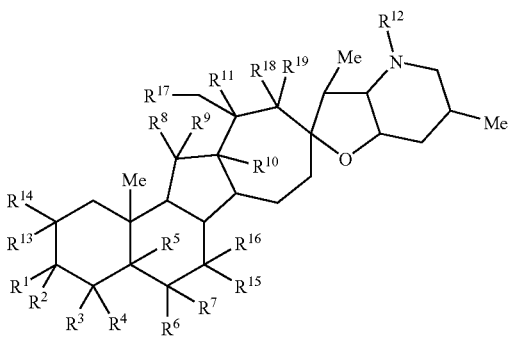

(1)

or a pharmaceutically acceptable salt thereof;
wherein each $R^1$ and $R^8$ is independently H, alkyl, alkenyl, alkynyl, aryl, cycloalkyl, heterocycloalkyl, aralkyl, heteroaryl, heteroaralkyl, halide, sulfhydryl, alkylthio, arylthio, aralkylthio, hydroxyl, alkoxyl, aryloxy, acyloxy, amino, alkylamino, arylamino, acylamino, aralkylamino, nitro, acylthio, carboxamide, sulfonamide, carboxyl, nitrile, sulfate, —OP(L)(OR$^{20}$)$_2$, —X—C(L)-R$^{21}$ or —X—C(L)-X—R$^{21}$;
wherein $R^1$ may also be a sugar;
X is O or NR wherein R is H, alkyl, alkenyl, alkynyl, aryl, cycloalkyl or aralkyl;
L is O or S;
$R^2$ and $R^9$ are independently H, alkyl, alkenyl, alkynyl, aryl, cycloalkyl, heterocycloalkyl, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl;
each $R^5$ and $R^{11}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;
each $R^3$, $R^4$, $R^6$, $R^7$, $R^{13}$ and $R^{14}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, heteroaryl, or heteroaralkyl;
or $R^1$ and $R^2$ and/or $R^8$ and $R^9$ taken together, along with the carbon to which they are bonded, form —(C=O)—, —(C=S)—, —(C=N(OR$^{20}$))—, —(C=N(R$^{20}$))—, —(C=N(N(R$^{20}$)(R$^{20}$))), or form an optionally substituted 3–8 membered ring; or
$R^4$ and $R^5$ taken together and/or $R^5$ and $R^6$ taken together and/or $R^{10}$ and $R^{11}$ taken together form a double bond or form a group represented by 1b

(1b)

wherein Z is NR$^{21}$, O, or C(R$^{23}$)(R$^{23}$);
$R^{12}$ is H, alkyl, alkenyl, alkynyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), [C(R$^{21}$)$_2$]$_q$—R$^{21}$, —[(W)—N(R$^{21}$)C(O)]$_q$R$^{21}$, —[(W)—C(O)]$_q$R$^{21}$, —[(W)—C(O)O]$_q$R$^{21}$, —[(W)—OC(O)]$_q$R$^{21}$, —[(W)—SO$_2$]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—N(R$^{21}$)]$_q$R$^{21}$, or —[(W)—S]$_q$R$^{21}$;
wherein W is a diradical, and q is 1, 2, 3, 4, 5, or 6;
$R^{15}$, $R^{16}$, and $R^{17}$ are independently H, alkoxyl, aryloxy, acyloxy, halide, hydroxyl, amino, alkylamino, arylamino, acylamino, aralkylamino; or $R^{15}$ and $R^{16}$ taken together, along with the carbon to which they are bonded, form —C(O)— or —C(S)—;
$R^{18}$ and $R^{19}$ are independently H, alkyl, aralkyl, halide, amido, or ester;
$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent can be taken together to form a 4–8 membered optionally substituted ring;
$R^{21}$ is H, alkyl, alkenyl, alkynyl, aryl, cycloalkyl, heterocycloalkyl, aralkyl, heteroaryl, heteroaralkyl or —[C(R$^{20}$)$_2$]$_p$—R$^{25}$ wherein p is 0–6; or any two occurrences of $R^{21}$ on the same substituent can be taken together to form a 4–8 membered optionally substituted ring;
$R^{23}$ is H, alkyl, alkenyl, alkynyl, aryl, cycloalkyl, heterocycloalkyl, aralkyl, heteroaryl, heteroaralkyl, halide, alkoxyl, aryloxy, acyloxy, silyloxy, nitrile, —C(O)R$^{21}$, —CO$_2$R$^{21}$, —SO$_2$R$^{21}$, and —C(O)N(R$^{21}$)$_2$;
$R^{25}$ is hydroxyl, acylamino, —N(R$^{20}$)COR$^{20}$, —N(R$^{20}$)C(O)OR$^{20}$, —N(R$^{20}$)SO$_2$(R$^{20}$), —COR$^{20}$N(R$^{20}$)$_2$, —OC(O)R$^{20}$)N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^{20}$, —S(O)$_2$OR$^{20}$, —OP(L)(OR$^{20}$)(OR$^{20}$), —NP(O)(OR$^{20}$)(OR$^{20}$), or —P(O)(OR$^{20}$)(OR$^{20}$).

In certain embodiments, the compounds of the present invention are represented by 1 and the attendant definitions, wherein $R^{13}$, $R^{14}$, $R^{15}$, $R^{16}$, and $R^{17}$ are hydrogen.

In certain embodiments, the compounds of the present invention are represented by 1 and the attendant definitions, wherein $R^1$ is hydroxyl, sugar, —OP(L)(OR$^{20}$)$_2$, —X—C(L)-R$^{21}$, or —X—C(L)-X—R$^{21}$; or $R^1$ and $R^2$ taken together, along with the carbon to which they are bonded, form —C(O)—.

In certain embodiments, the compounds of the present invention are represented by 1 and the attendant definitions, wherein $R^4$ and $R^5$ taken together form a double bond.

In certain embodiments, the compounds of the present invention are represented by 1 and the attendant definitions, wherein $R^1$ and $R^2$ taken together, along with the carbon to which they are bonded, form —C(O)—.

In certain embodiments, the compounds of the present invention are represented by 1 and the attendant definitions, wherein $R^1$ is hydroxyl and $R^2$ is H.

In certain embodiments, the compounds of the present invention are represented by 1 and the attendant definitions, wherein $R^1$ is hydroxyl, $R^2$ is H; and $R^5$ and $R^6$ taken together form a double bond; or $R^5$ and $R^6$ taken together form a group represented by 1b;

(1b)

wherein:

Z is $C(R^{23})(R^{23})$.

In certain embodiments, the compounds of the present invention are represented by 1 and the attendant definitions, wherein $R^{10}$ and $R^{11}$ taken together form a double bond; or $R^{10}$ and $R^{11}$ taken together form a group represented by 1b;

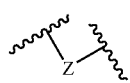
(1b)

wherein:

Z is $C(R^{23})(R^{23})$.

In certain embodiments, the compounds of the present invention are represented by 1 and the attendant definitions, wherein $R^5$ and $R^6$ taken together form a double bond and $R^{10}$ and $R^{11}$ taken together form a double bond.

In certain embodiments, the compounds of the present invention are represented by 1 and the attendant definitions, wherein $R^1$ and $R^2$ taken together, along with the carbon to which they are bonded, form —C(O)—; $R^4$ and $R^5$ taken together form a double bond; and $R^{10}$ and $R^{11}$ taken together form a double bond; or $R^{10}$ and $R^{11}$ taken together form a group represented by 1b;

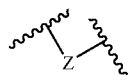
(1b)

wherein:

Z is $C(R^{23})(R^{23})$.

In certain embodiments, the compounds of the present invention are represented by 1 and the attendant definitions, wherein $R^1$ is hydroxyl and $R^2$ is H; $R^{10}$ and $R^{11}$ taken together form a double bond; or $R^{10}$ and $R^{11}$ taken together form a group represented by 1b;

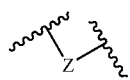
(1b)

wherein:

Z is $C(R^{23})(R^{23})$.

In certain embodiments, the compounds of the present invention are represented by 1 and the attendant definitions, wherein $R^8$ and $R^9$ are hydrogen; or $R^8$ and $R^9$ taken together, along with the carbon to which they are bonded, is —C(O)—.

In certain embodiments, the compounds of the present invention are represented by 1 and the attendant definitions, wherein $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q$R, —[(W)—C(O)]$_q$R, or [(W)—C(O)O]$_q R^{21}$.

In certain embodiments, the compounds of the present invention are represented by 1 and the attendant definitions, wherein $R^{13}$, $R^{14}$, $R^{15}$, $R^{16}$, and $R^{17}$ are hydrogen; and $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

In certain embodiments, the compounds of the present invention are represented by 1 and the attendant definitions, wherein $R^4$ and $R^5$ taken together form a double bond; $R^1$ and $R^2$ taken together, along with the carbon to which they are bonded, form —C(O)—; and $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

In certain embodiments, the compounds of the present invention are represented by 1 and the attendant definitions, wherein $R^1$ is hydroxyl and $R^2$ is H; and $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

In certain embodiments, the compounds of the present invention are represented by a compound of the formula:

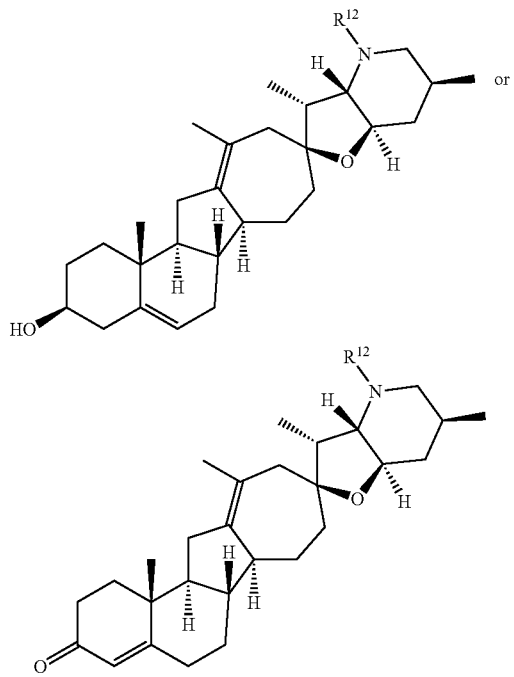

wherein:

$R^{12}$ is H, alkyl, aryl, cycloalkyl, heterocycloalkyl, hydroxyl, aralkyl, heteroaryl, heteroaralkyl, haloalkyl, alkoxyl, —C(O)$R^{21}$, —CO$_2 R^{21}$, —SO$_2 R^{21}$, —C(O)N($R^{21}$)($R^{21}$), [C($R^{21}$)$_2$]—$R^{21}$, —[(W)—N($R^{21}$)C(O)]$_q R^{21}$, —[(W)—C(O)]$_q R^{21}$, —[(W)—C(O)O]$_q R^{21}$, —[(W)—OC(O)]$_q R^{21}$, —[(W)—SO$_2$]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—N($R^{21}$)]$_q R^{21}$, or —[(W)—S]$_q R^{21}$;

wherein each W is independently a diradical;

q is 1, 2, 3, 4, 5, or 6;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ can be taken together to form a 4–8 membered optionally substituted ring;

R²¹ is H, alkyl, aryl, cycloalkyl, heterocycloalkyl, aralkyl, heteroaryl, heteroaralkyl or —[C(R²⁰)₂]ₚ—R²⁵; or any two occurrences of R²¹ can be taken together to form a 4–8 membered optionally substituted ring;

R²⁵ is hydroxyl, acylamino, —N(R²⁰)COR²⁰, —N(R²⁰)C(O)OR²⁰, —N(R²⁰)SO₂(R²⁰), —COR²⁰N(R²⁰)₂, —OC(O)R²⁰N(R²⁰)(R²⁰), —SO₂N(R²⁰)(R²⁰), —N(R²⁰)(R²⁰), —COR²⁰, —C(O)N(OH)(R²¹), —OS(O)₂OR¹⁹, —S(O)₂OR²⁰, —OP(L)(OR²⁰)(OR²⁰), —NP(O)(OR²)(OR²⁰), or —P(O)(OR²⁰)(OR²⁰).

The present invention specifically provides compounds represented by the group consisting of:

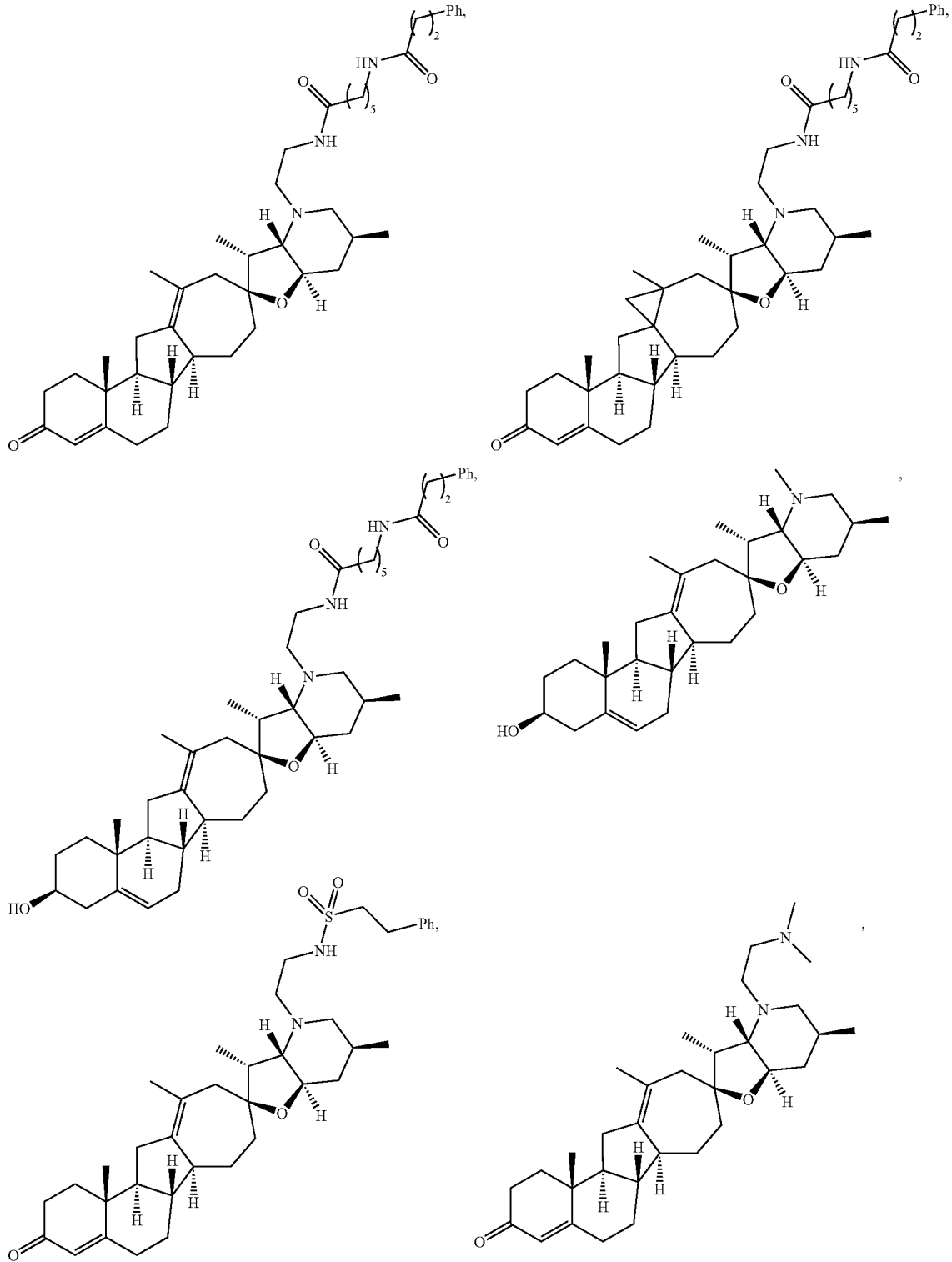

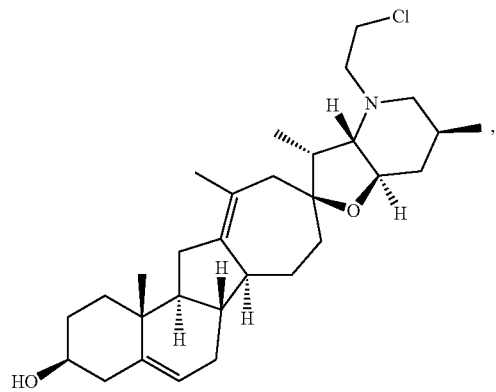
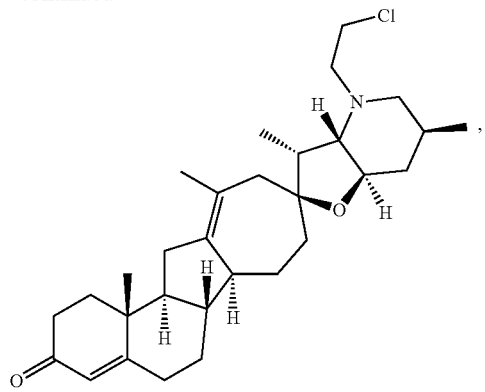
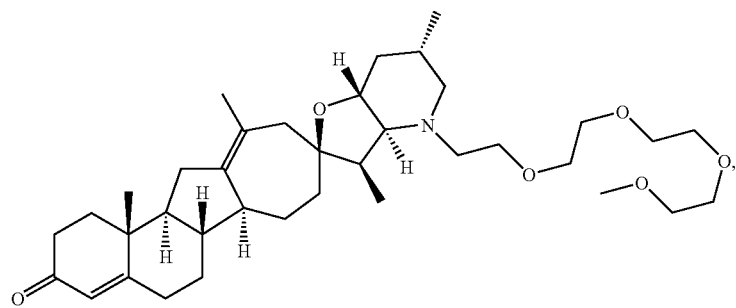
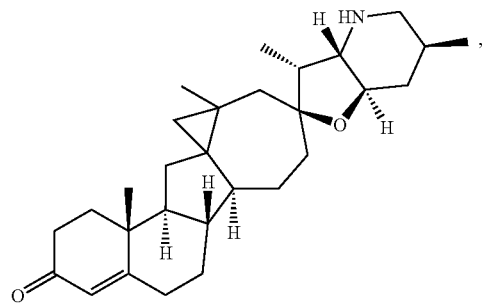
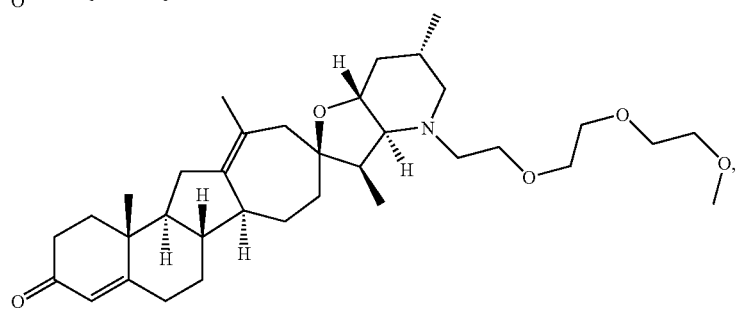
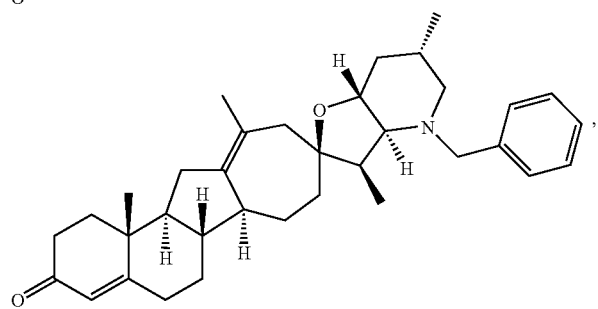

-continued
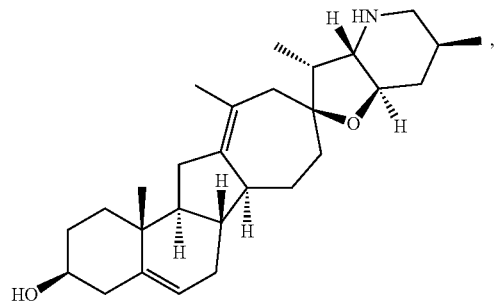
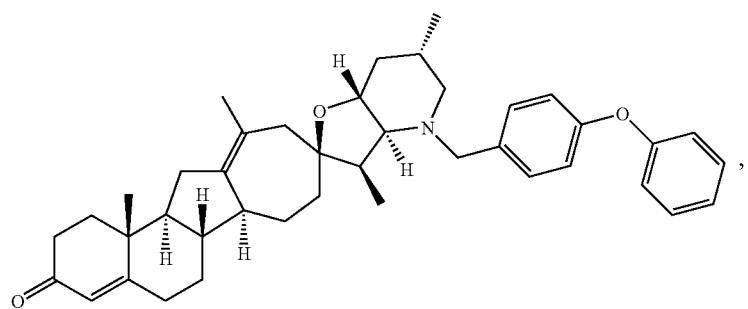
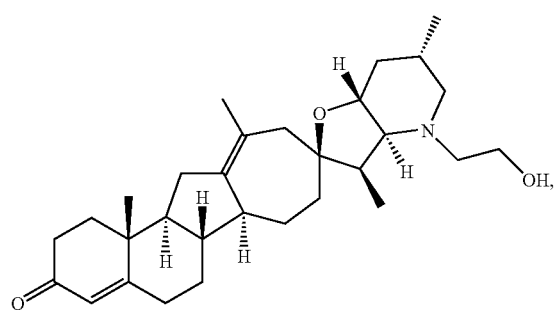
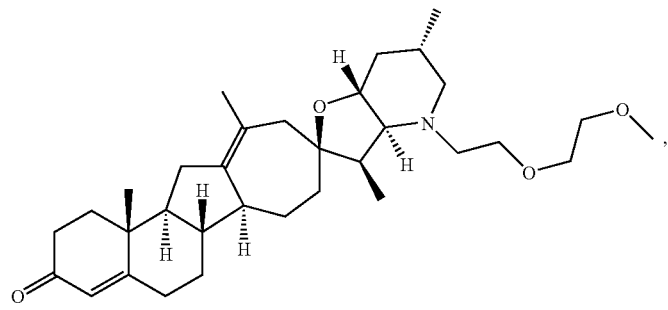
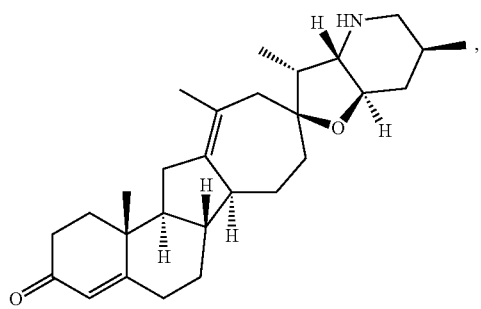
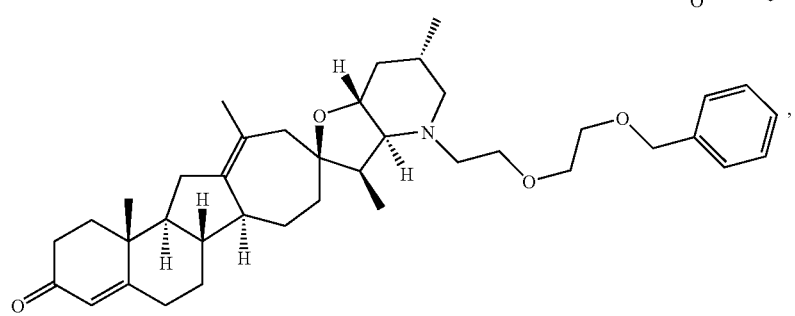

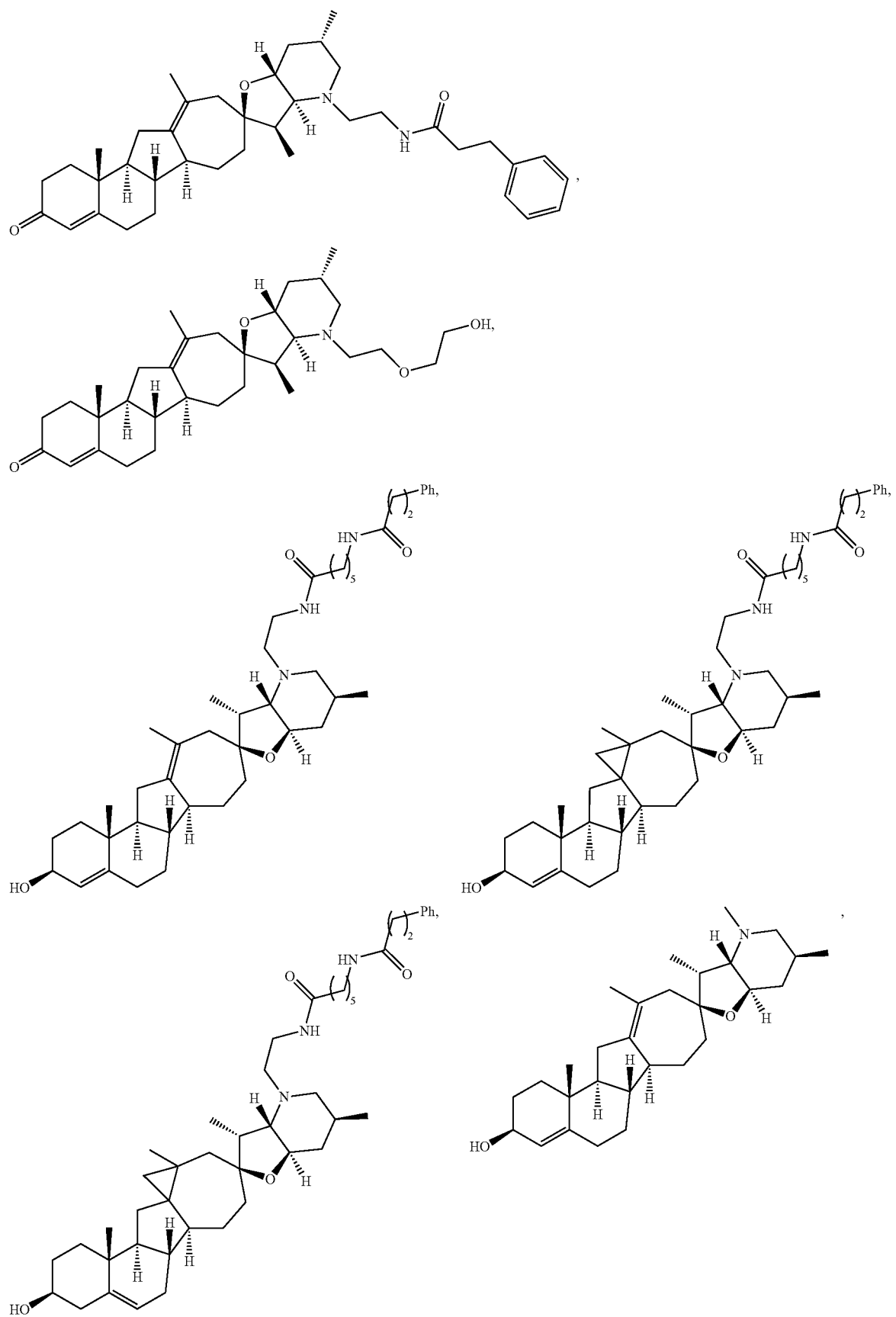

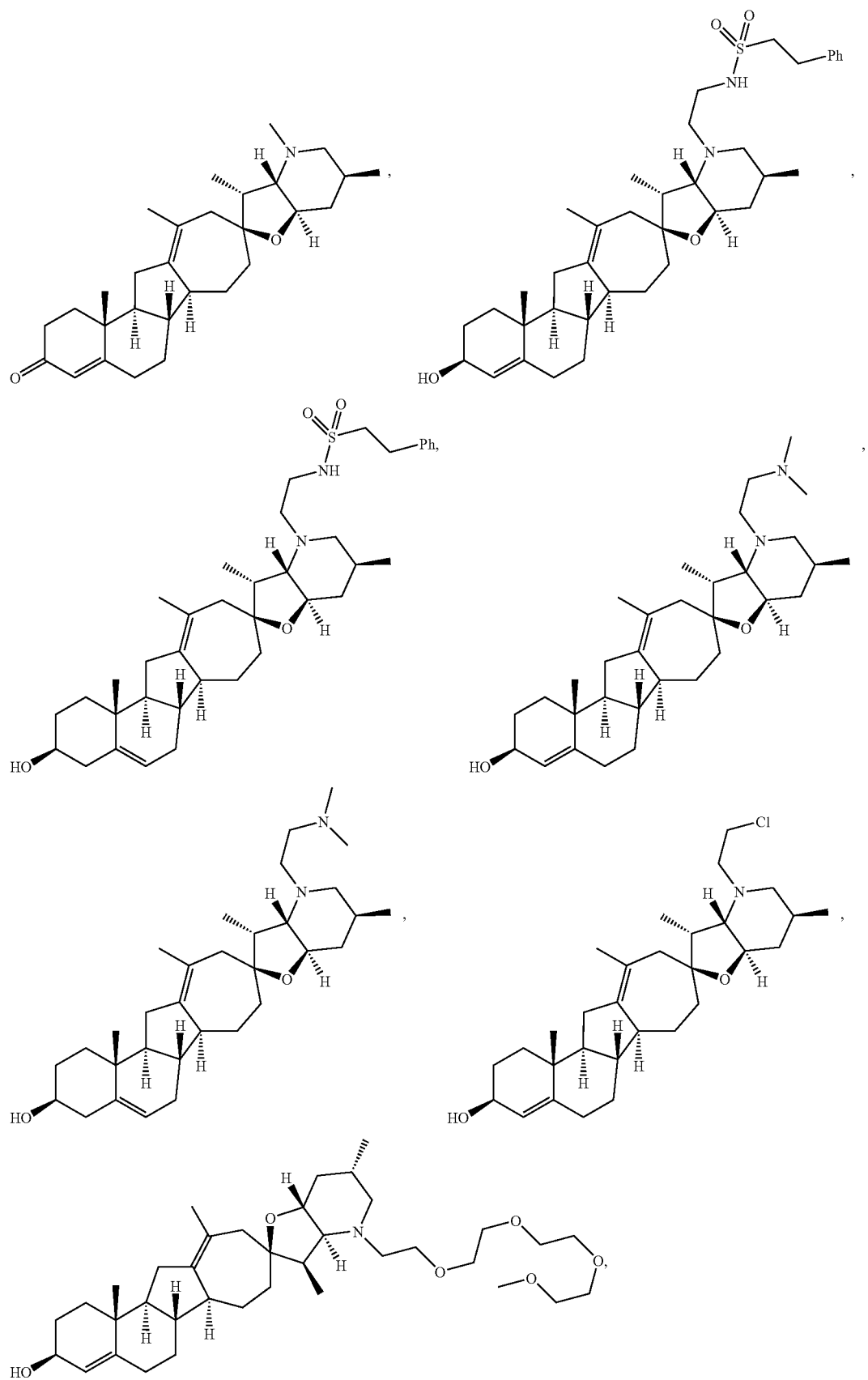

-continued
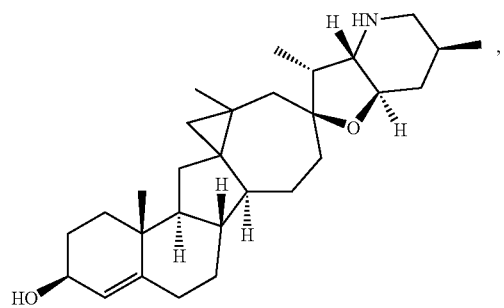
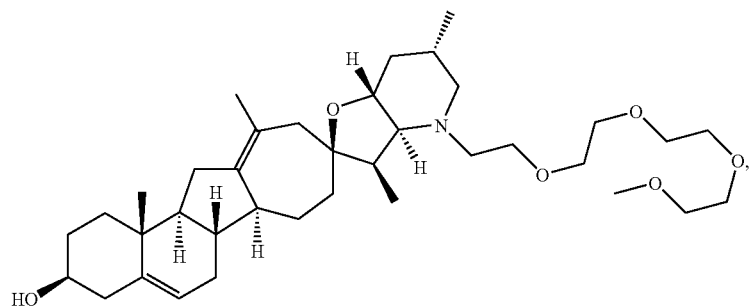
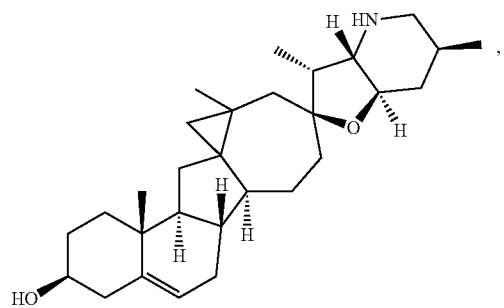
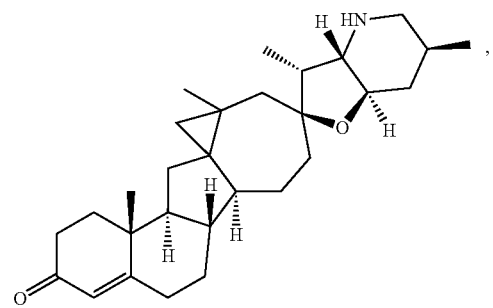
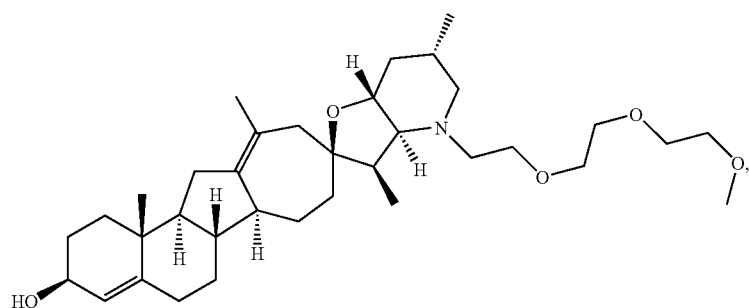
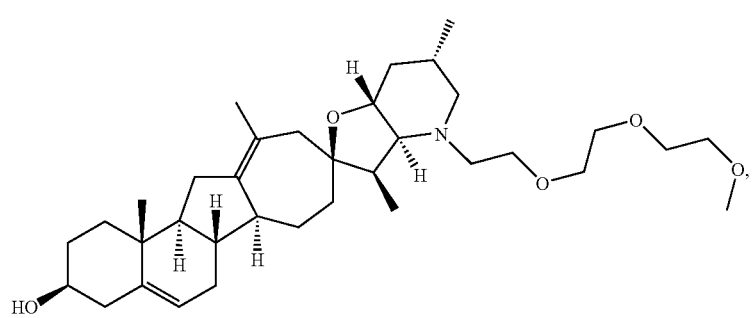

-continued
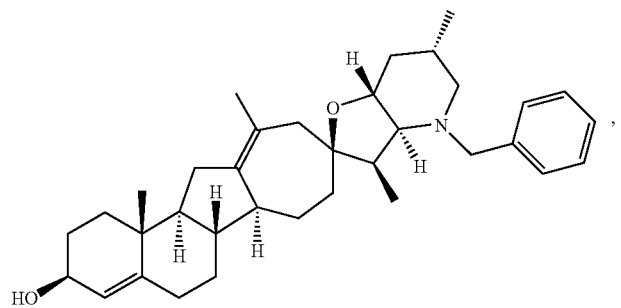
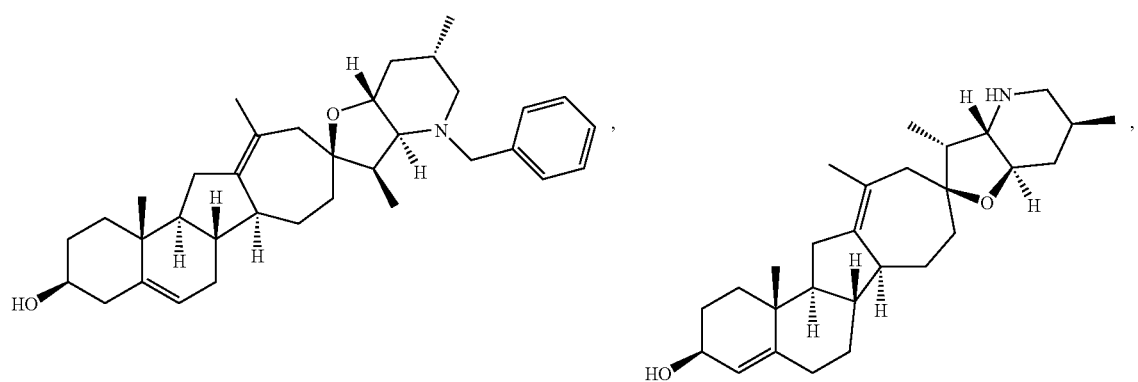
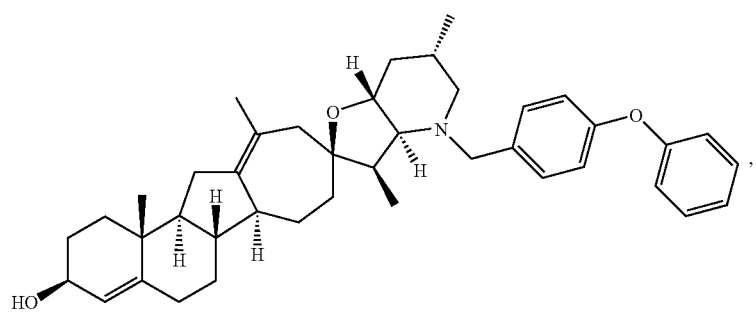
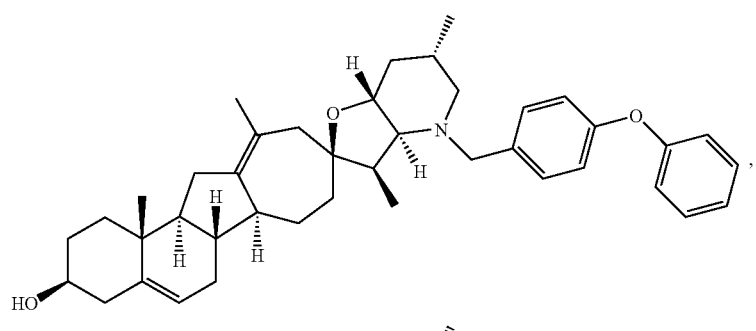
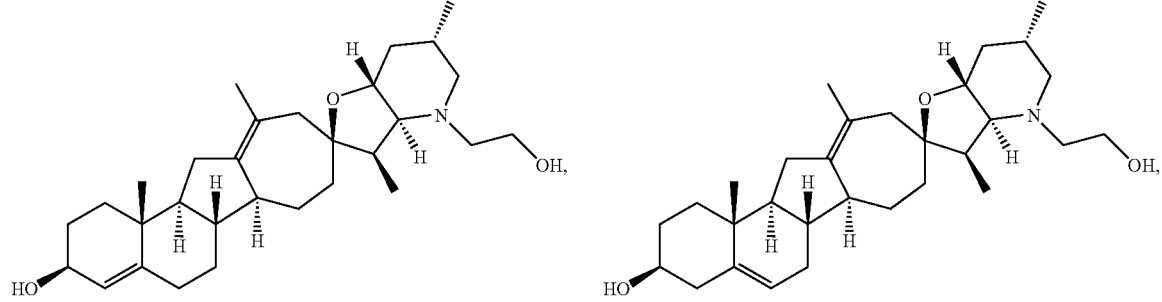

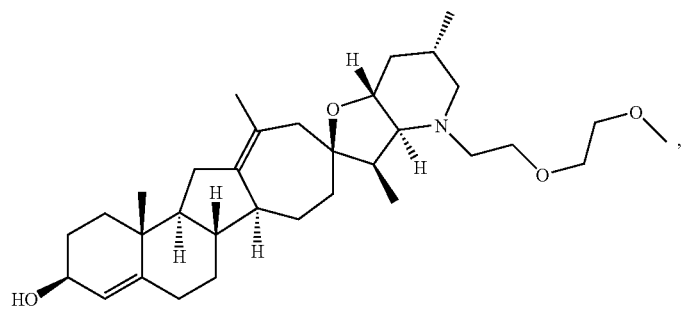
,
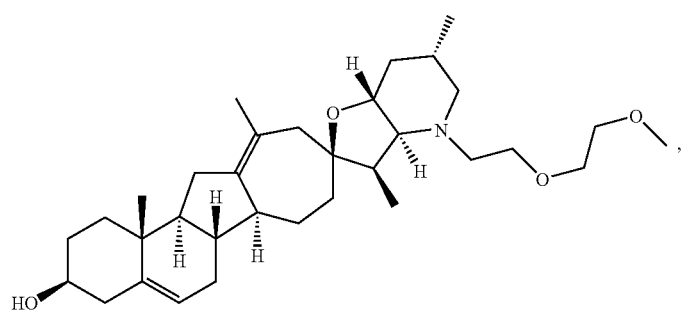
,
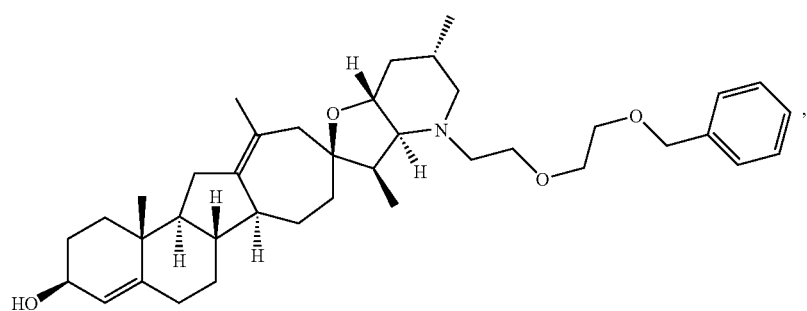
,
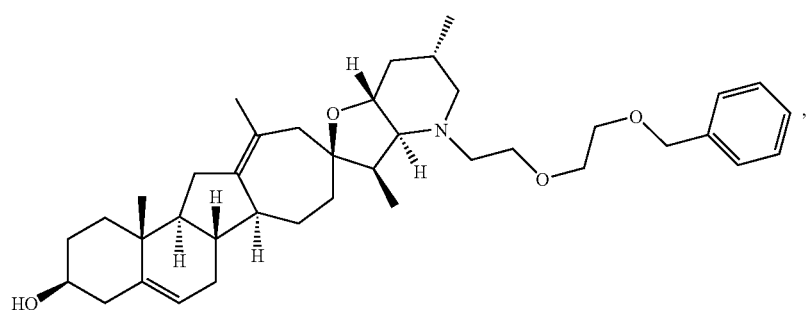
,
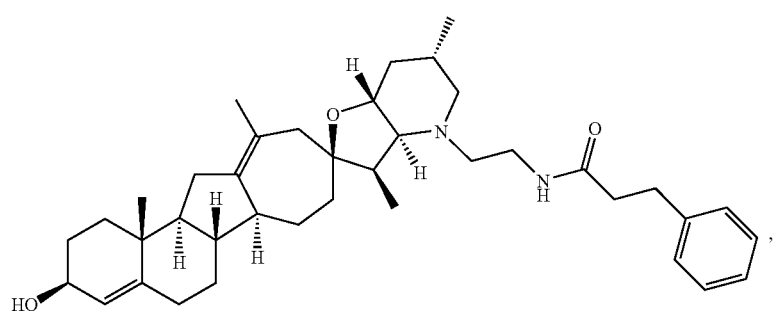
,

-continued
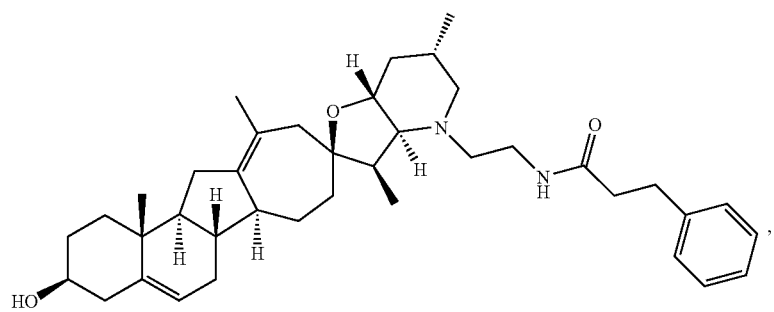
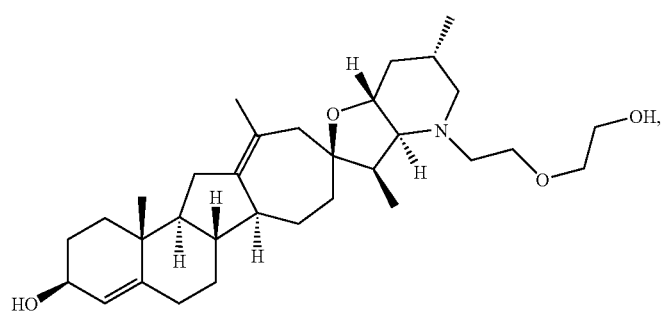
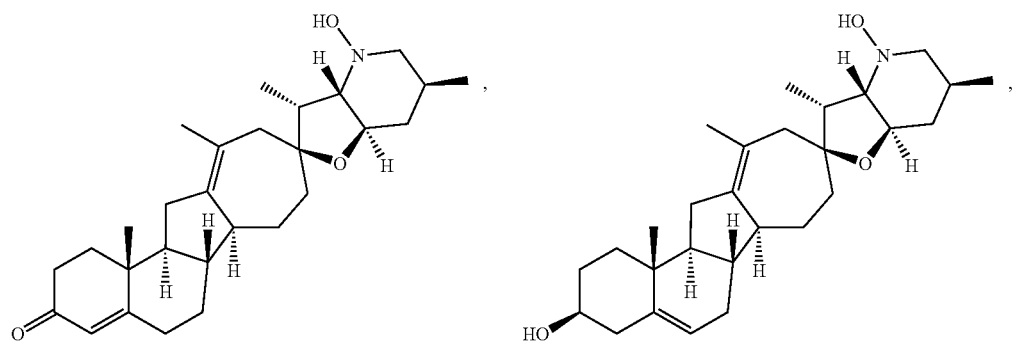
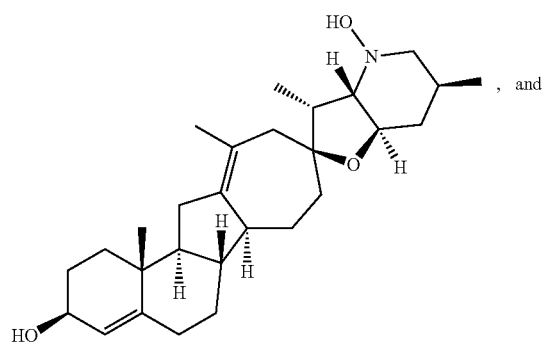, and

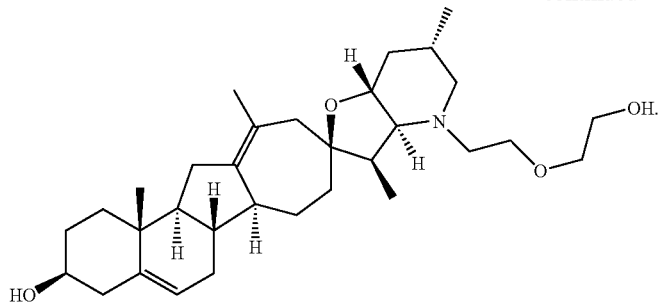

In certain embodiments, the compounds of the present invention are represented by any of the aforementioned compounds and the attendant definitions, wherein the compound is represented by the formula:

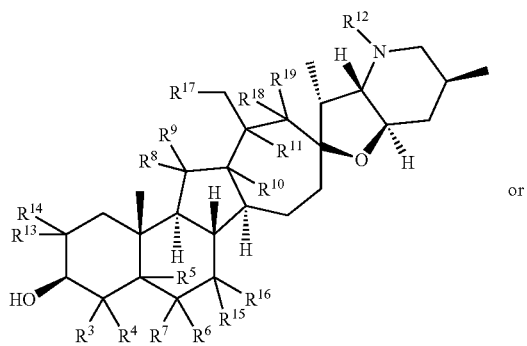

or

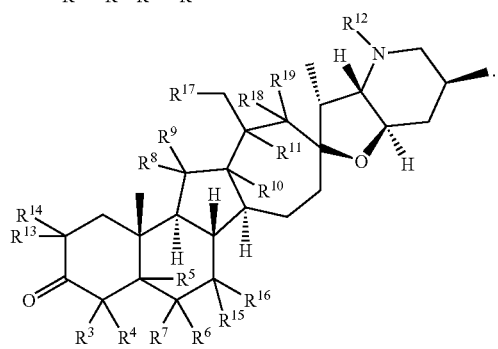

In one embodiment, the present invention provides compounds represented by a compound of Formula 2:

(2)

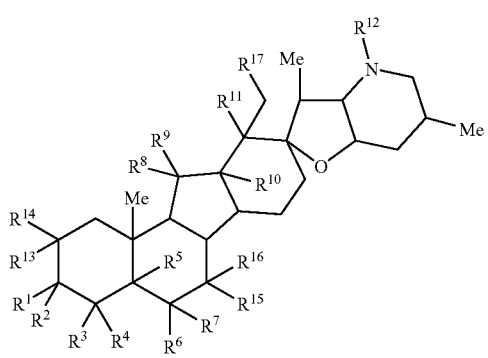

or a pharmaceutically acceptable salt thereof;

wherein each $R^1$ and $R^8$ is independently H, alkyl, alkenyl, alkynyl, aryl, cycloalkyl, heterocycloalkyl, aralkyl, heteroaryl, heteroaralkyl, halide, sulfhydryl, alkylthio, arylthio, aralkylthio, hydroxyl, alkoxyl, aryloxy, acyloxy, amino, alkylamino, arylamino, acylamino, aralkylamino, nitro, acylthio, carboxamide, sulfonamide, carboxyl, nitrile, sulfate, —OP(L)(OR$^{20}$)$_2$, —X—C(L)-R$^{21}$ or —X—C(L)-X—R$^{21}$;

wherein $R^1$ may also be a sugar;

X is O or NR wherein R is H, alkyl, alkenyl, alkynyl, aryl, cycloalkyl or aralkyl;

L is O or S;

$R^2$ and $R^9$ are independently H, alkyl, alkenyl, alkynyl, aryl, cycloalkyl, heterocycloalkyl, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl;

each $R^5$ and $R^{11}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;

each $R^3$, $R^4$, $R^6$, $R^7$, $R^{13}$ and $R^{14}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, heteroaryl, or heteroaralkyl;

wherein $R^1$ and $R^2$ and/or $R^8$ and $R^9$ taken together, along with the carbon to which they are bonded, form —(C=O)—, —(C=S)—, —(C=N(OR$^{20}$))—, —(C=N(R$^{20}$))—, —(C=N(N(R$^{20}$)(R$^{20}$))), or form an optionally substituted 3–8 membered ring; or $R^4$ and $R^5$ taken together and/or $R^5$ and $R^6$ taken together and/or $R^{10}$ and $R^{11}$ taken together form a double bond or form a group represented by 1b (1b)

wherein Z is NR$^{21}$, O, or C(R$^{23}$)(R$^{23}$);

$R^{12}$ is H, alkyl, alkenyl, alkynyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), —[C(R$^{21}$)$_2$]$_q$—R$^{21}$, [(W)—N(R$^{21}$)C(O)]$_q$R$^{21}$, —[(W)—C(O)]$_q$R$^{21}$, [(W)—C(O)O]$_q$R$^{21}$, —[(W)—OC(O)]$_q$R$^{21}$, —[(W)—SO$_2$]$_q$R$^{21}$, —[(W)—N($R^{21}$)$SO_2$]$_q$$R^{21}$, —[(W)—C(O)N($R^{21}$)]$_q$$R^{21}$, —[(W)—O]$_q$$R^{21}$, —[(W)—N($R^{21}$)]$_q$$R^{21}$, or —[(W)—S]$_q$$R^{21}$;

wherein W is a diradical, and q is 1, 2, 3, 4, 5, or 6;

$R^{15}$, $R^{16}$, and $R^{17}$ are independently H, alkoxyl, aryloxy, acyloxy, halide, hydroxyl, amino, alkylamino, arylamino, acylamino, aralkylamino; or $R^{15}$ and $R^{16}$ taken together, along with the carbon to which they are bonded, form —C(O)— or —C(S)—;

$R^{18}$ and $R^{19}$ are independently H, alkyl, araalkyl, halide, amido, or ester;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent can be taken together to form a 4–8 membered optionally substituted ring;

$R^{21}$ is H, alkyl, alkenyl, alkynyl, aryl, cycloalkyl, heterocycloalkyl, aralkyl, heteroaryl, heteroaralkyl or —[C($R^{20}$)$_2$]$_p$—$R^{25}$ wherein p is 0–6; or any two occurrences of $R^{21}$ on the same substituent can be taken together to form a 4–8 membered optionally substituted ring;

$R^{23}$ is H, alkyl, alkenyl, alkynyl, aryl, cycloalkyl, heterocycloalkyl, aralkyl, heteroaryl, heteroaralkyl, halide, alkoxyl, aryloxy, acyloxy, silyloxy, nitrile, —C(O)$R^{21}$, —$CO_2R^{21}$, —$SO_2R^{21}$, and —C(O)N($R^{21}$)$_2$; and $R^{25}$ is hydroxyl, acylamino, —N($R^{20}$)COR$^{20}$, —N($R^{20}$)C(O)OR$^{20}$, —N($R^{20}$)SO$_2$($R^{20}$), —COR$^2$N($R^{21}$)$_2$, —OC(O)$R^{20}$N($R^{20}$)($R^{20}$), —SO$_2$N($R^{20}$)($R^{20}$), —N($R^{20}$)($R^{20}$), —COR$^{20}$, —C(O)N(OH)($R^{21}$), —OS(O)$_2$OR$^{20}$, —S(O)$_2$OR$^{21}$, —OP(L)(OR$^{20}$)(OR$^{20}$), —NP(O)(OR$^{20}$)(OR$^{20}$), or —P(O)(OR$^{20}$)(OR$^{20}$);

provided that there is at least one group represented by formula 1b on said compound of formula 2.

In certain embodiments, the compounds of the present invention are represented by Formula 2 and the attendant definitions, wherein herein $R^{13}$, $R^{14}$, $R^{15}$, $R^{16}$, and $R^{17}$ are hydrogen.

In certain embodiments, the compounds of the present invention are represented by Formula 2 and the attendant definitions, wherein $R^1$ is hydroxyl, sugar, —OP(L)(OR$^{20}$)$_2$, —X—C(L)-$R^{21}$, or —X—C(L)-X—$R^{21}$; or $R^1$ and $R^2$ taken together, along with the carbon to which they are bonded, form —C(O)—.

In certain embodiments, the compounds of the present invention are represented by Formula 2 and the attendant definitions, wherein $R^4$ and $R^5$ taken together form a double bond.

In certain embodiments, the compounds of the present invention are represented by Formula 2 and the attendant definitions, wherein $R^1$ and $R^2$ taken together, along with the carbon to which they are bonded, form —C(O)—.

In certain embodiments, the compounds of the present invention are represented by Formula 2 and the attendant definitions, wherein $R^1$ is hydroxyl and $R^2$ is H.

In certain embodiments, the compounds of the present invention are represented by Formula 2 and the attendant definitions, wherein $R^1$ is hydroxyl, $R^2$ is H; and $R^5$ and $R^6$ taken together form a double bond; or $R^5$ and $R^6$ taken together form a group represented by Formula 2b;

(1b)

wherein:

Z is C($R^{23}$)($R^{23}$).

In certain embodiments, the compounds of the present invention are represented by Formula 2 and the attendant definitions, wherein $R^{10}$ and $R^{11}$ taken together form a double bond; or $R^{10}$ and $R^{11}$ taken together form a group represented by 1b;

(1b)

wherein:

Z is C($R^{23}$)($R^{23}$).

In certain embodiments, the compounds of the present invention are represented by Formula 2 and the attendant definitions, wherein $R^5$ and $R^6$ taken together form a double bond and $R^{10}$ and $R^{11}$ taken together form a double bond.

In certain embodiments, the compounds of the present invention are represented by Formula 2 and the attendant definitions, wherein $R^1$ and $R^2$ taken together, along with the carbon to which they are bonded, form —C(O)—; $R^4$ and $R^5$ taken together form a double bond; and $R^{10}$ and $R^{11}$ taken together form a double bond; or $R^{10}$ and $R^{11}$ taken together form a group represented by 1b;

(1b)

wherein:

Z is C($R^{23}$)($R^{23}$).

In certain embodiments, the compounds of the present invention are represented by Formula 2 and the attendant definitions, wherein $R^1$ is hydroxyl and $R^2$ is H; $R^{10}$ and $R^{11}$ taken together form a double bond; or $R^{10}$ and $R^{11}$ taken together form a group represented by Formula 2b;

(1b)

wherein:

Z is C($R^{23}$)($R^{23}$).

In certain embodiments, the compounds of the present invention are represented by Formula 2 and the attendant definitions, wherein $R^8$ and $R^9$ are hydrogen; or $R^8$ and $R^9$ taken together, along with the carbon to which they are bonded, is —C(O)—.

In certain embodiments, the compounds of the present invention are represented by Formula 2 and the attendant definitions, wherein $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q$$R^{21}$, —[(W)—N($R^{21}$)SO$_2$]$_q$$R^{21}$, —[(W)—C(O)N($R^{21}$)]$_q$$R^{21}$, —[(W)—O]$_q$$R^{21}$, —[(W)—C(O)]$_q$$R^{21}$, or —[(W)—C(O)O]$_q$$R^{21}$.

In certain embodiments, the compounds of the present invention are represented by Formula 2 and the attendant definitions, wherein $R^{13}$, $R^{14}$, $R^{15}$, $R^{16}$, and $R^{17}$ are hydrogen; and $R^{12}$ is H, alkyl, cycloalkyl, aralkyl, heteroaryl, heteroaralkyl, haloalkyl, hydroxyl, alkoxyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

In certain embodiments, the compounds of the present invention are represented by Formula 2 and the attendant definitions, wherein $R^4$ and $R^5$ taken together form a double bond; $R^1$ and $R^2$ taken together, along with the carbon to which they are bonded, form —C(O)—; and $R^{12}$ is H, alkyl, cycloalkyl, aralkyl, heteroaryl, heteroaralkyl, haloalkyl, hydroxyl, alkoxyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

In certain embodiments, the compounds of the present invention are represented by Formula 2 and the attendant definitions, wherein $R^1$ is hydroxyl and $R^2$ is H; and $R^{12}$ is H, alkyl, cycloalkyl, aralkyl, heteroaryl, heteroaralkyl, haloalkyl, hydroxyl, alkoxyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

In certain embodiments, the compounds of the present invention are represented by a compound of the formula:

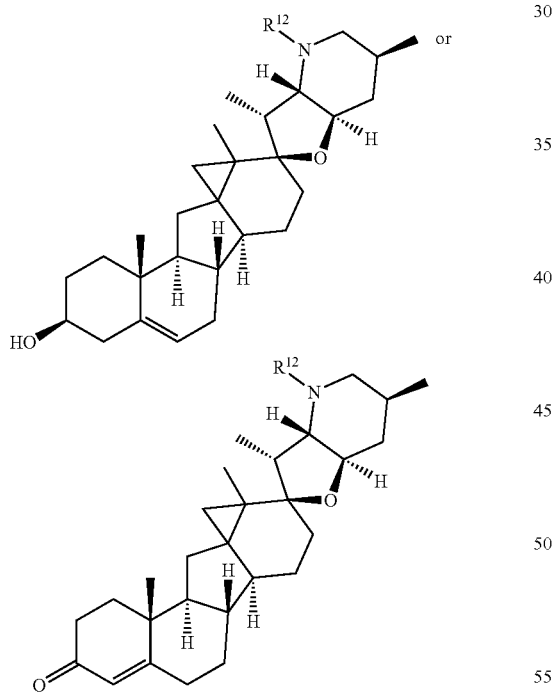

wherein:
$R^{12}$ is H, alkyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), [C(R$^{21}$)$_2$]$_p$—R$^{21}$, —[(W)—N(R$^{21}$)C(O)]$_q$R$^{21}$, —[(W)—C(O)]$_q$R$^{21}$, —[(W)—C(O)O]$_q$R$^{21}$, —[(W)—OC(O)]$_q$R$^{21}$, —[(W)—SO$_2$]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—N(R$^{21}$)]$_q$R$^{21}$, or —[(W)—S]$_q$R$^{21}$;

q is 1, 2, 3, 4, 5, or 6;

$R^{20}$ is H, alkyl, alkenyl, alkynyl, aryl, cycloalkyl, heterocycloalkyl, aralkyl, heteroaryl, or heteroaralkyl; or any two occurrences of R$^{20}$ can be taken together to form a 4–8 membered optionally substituted ring;

$R^{21}$ is H, alkyl, aryl, cycloalkyl, heterocycloalkyl, aralkyl, heteroaryl, heteroaralkyl or —[C(R$^{20}$)$_2$]$_p$—R$^{25}$; or any two occurrences of R$^{21}$ can be taken together to form a 4–8 membered optionally substituted ring;

$R^{25}$ is hydroxyl, acylamino, —N(R$^{20}$)COR$^{20}$, —N(R$^{20}$)C(O)OR$^{20}$, —N(R$^{20}$)SO$_2$(R$^{21}$), —COR$^{20}$N(R$^{20}$)$_2$, —OC(O)R$^{20}$N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^{19}$, —S(O)$_2$OR$^{20}$—OP(L)(OR$^2$)(OR$^2$), —NP(O)(OR$^{20}$)(OR$^{20}$), or —P(O)(OR$^{20}$)(OR$^{20}$).

The present invention specifically provides compounds represented by the group consisting of:

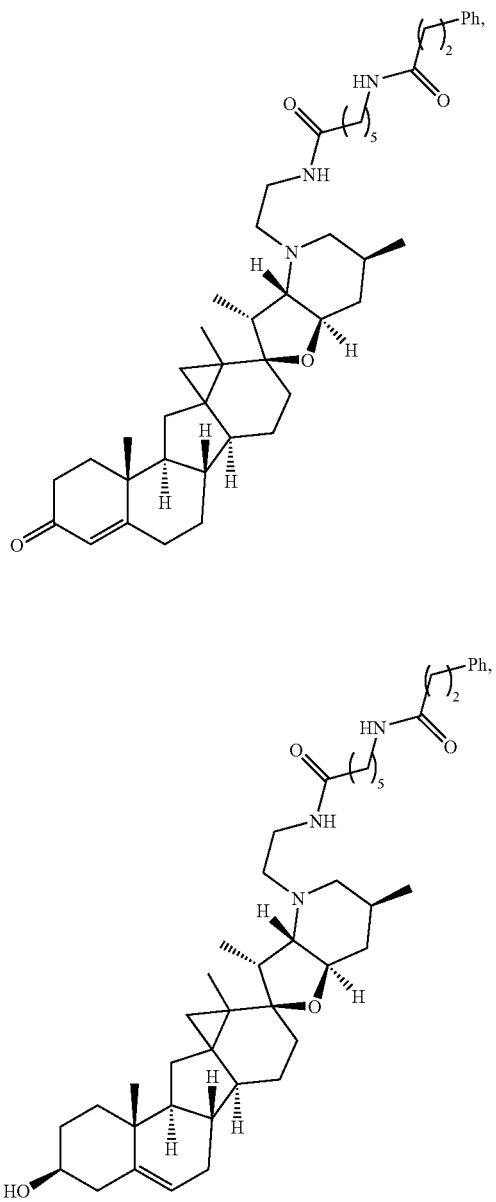

43
-continued
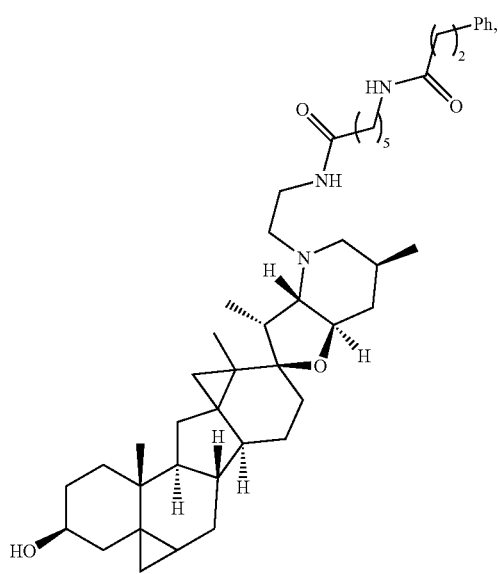
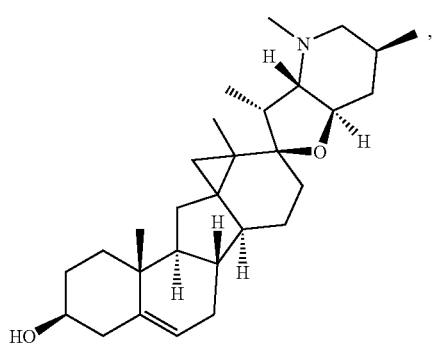
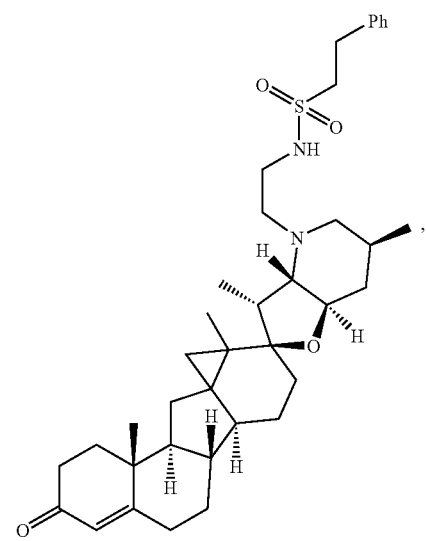
44
-continued
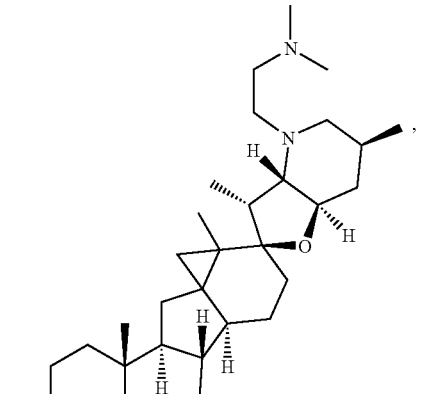
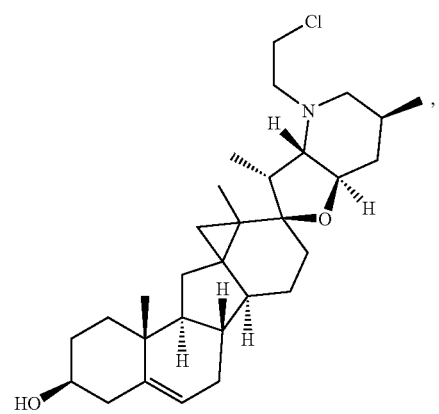
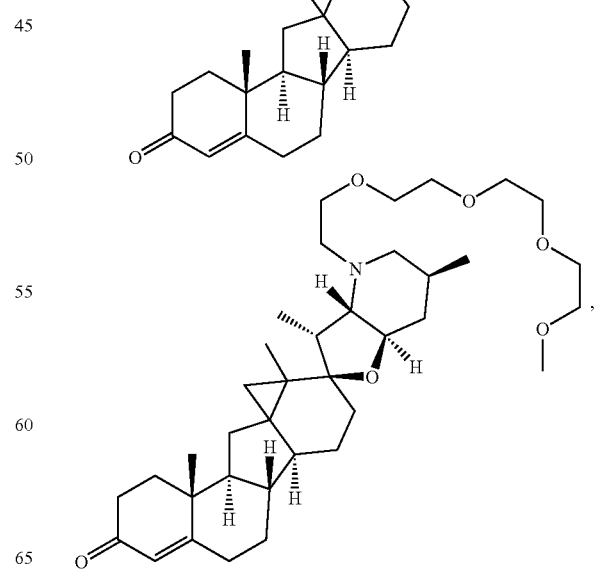

45
-continued
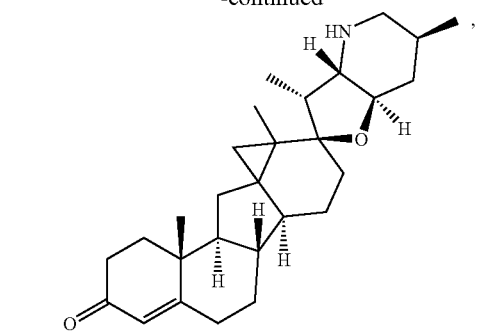
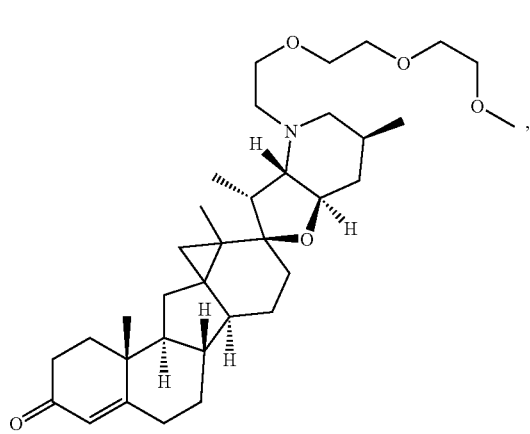
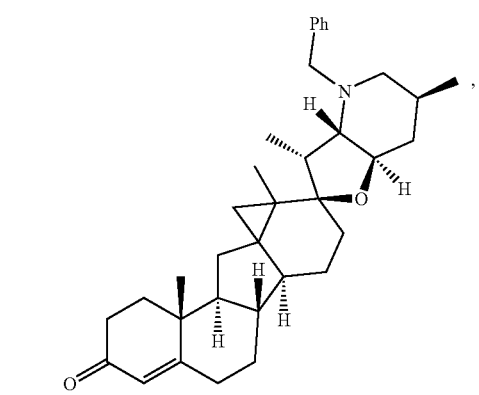
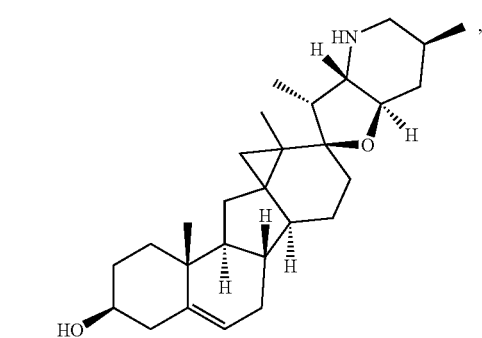
46
-continued
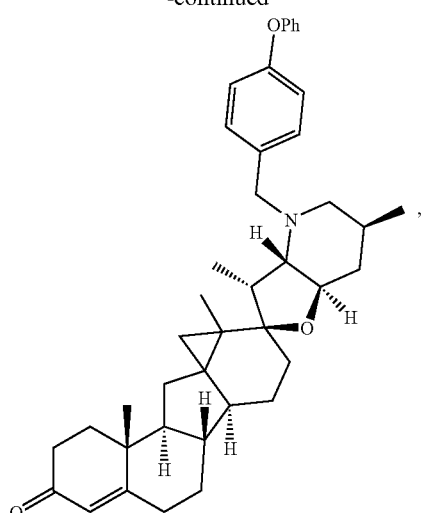
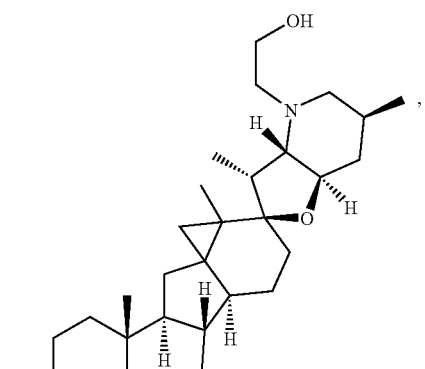
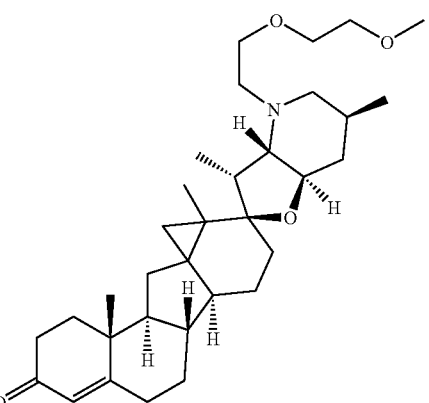
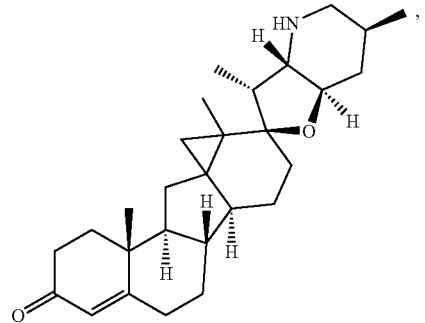

47
-continued
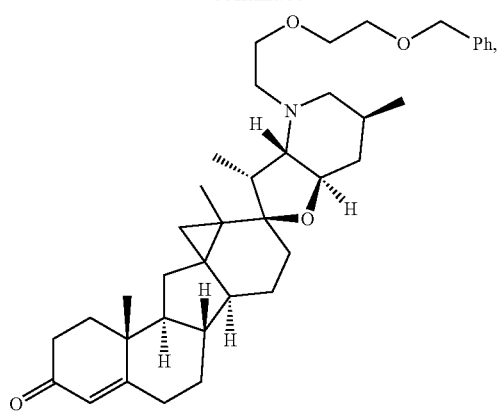
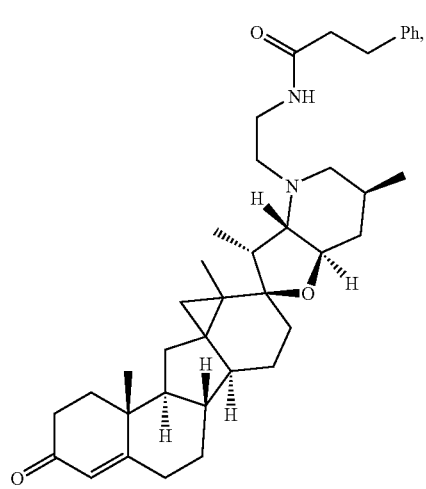
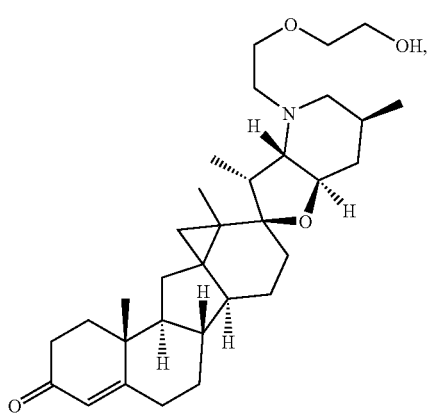
48
-continued
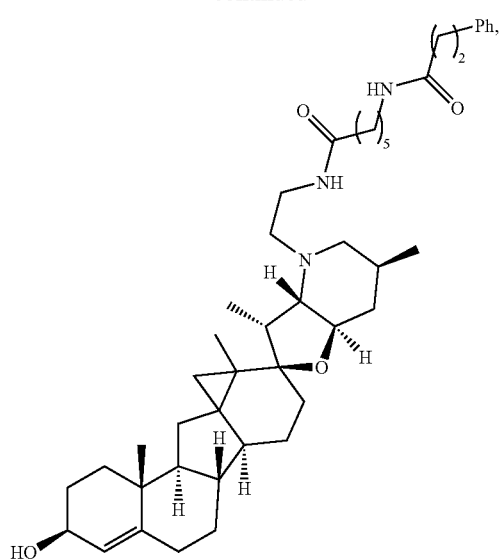
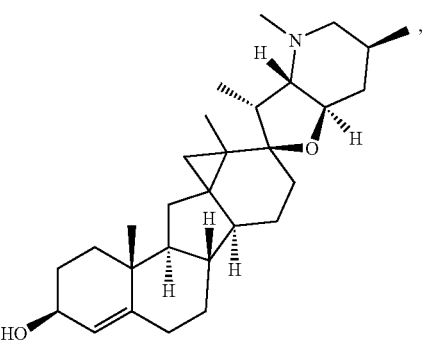
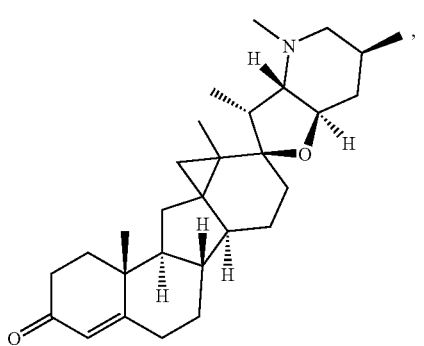

49
-continued
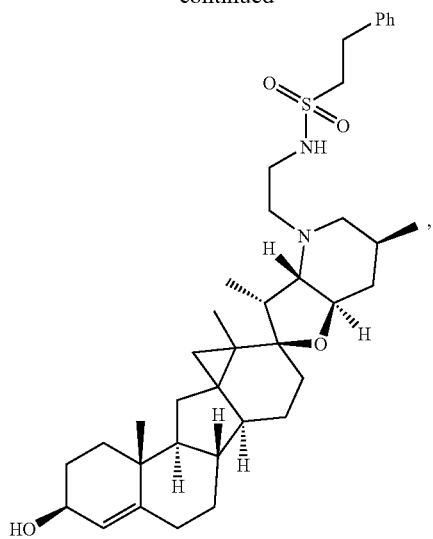
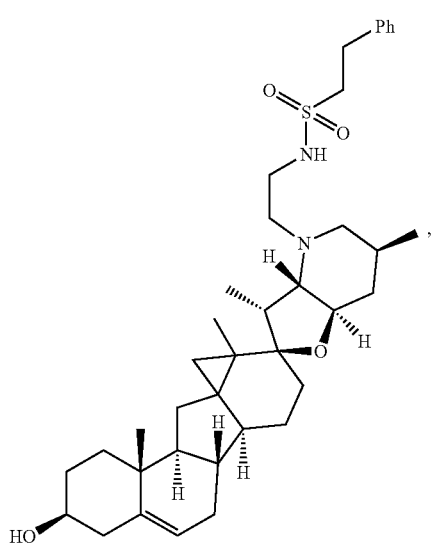
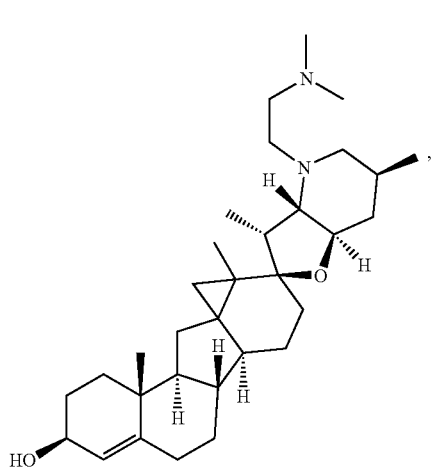
50
-continued
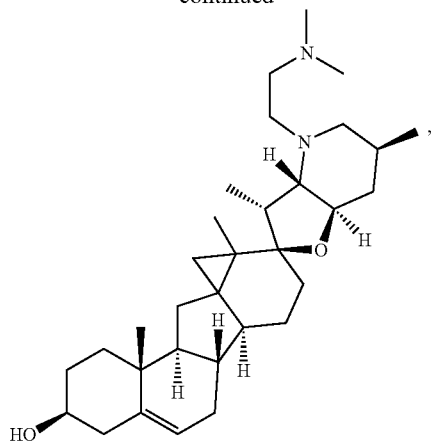
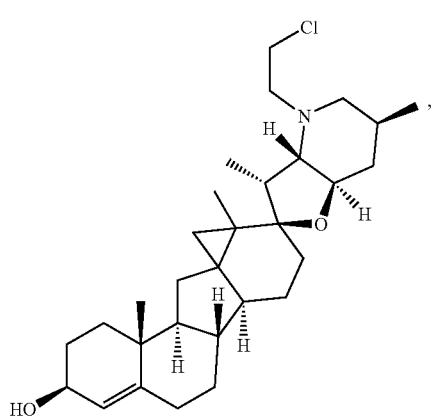
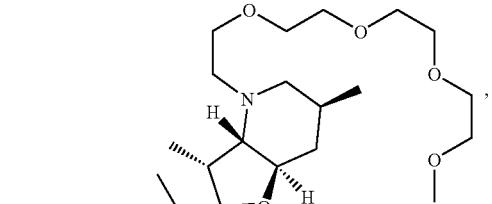
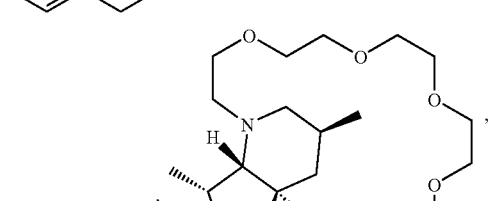

51
-continued
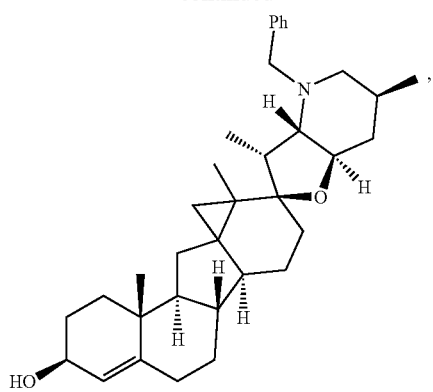
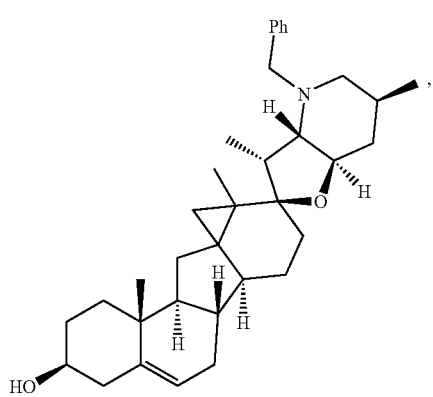
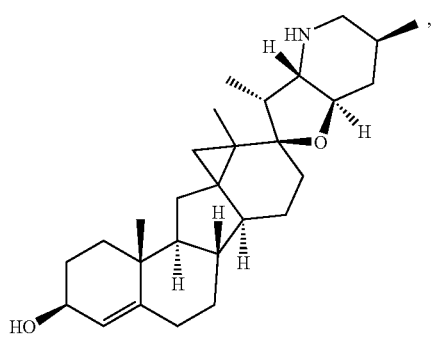
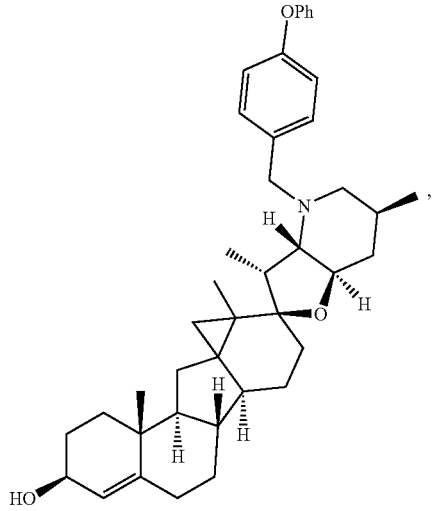
52
-continued
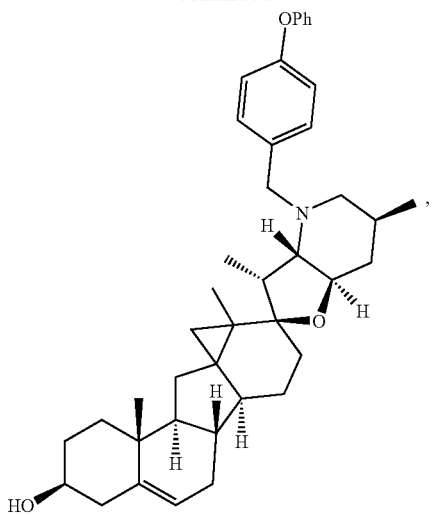
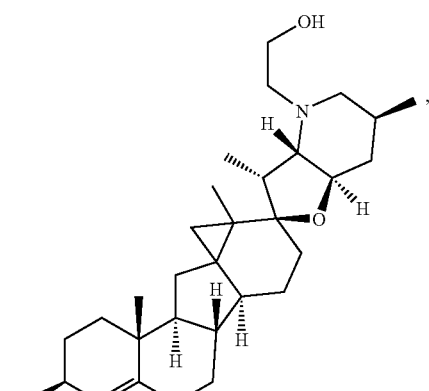
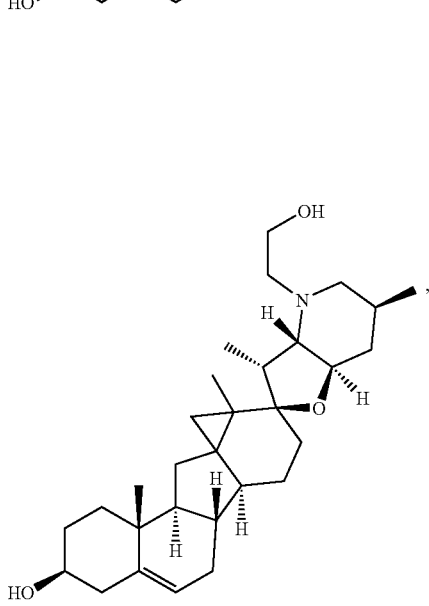

53
-continued
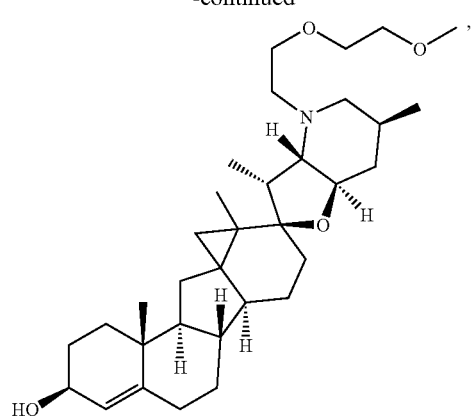
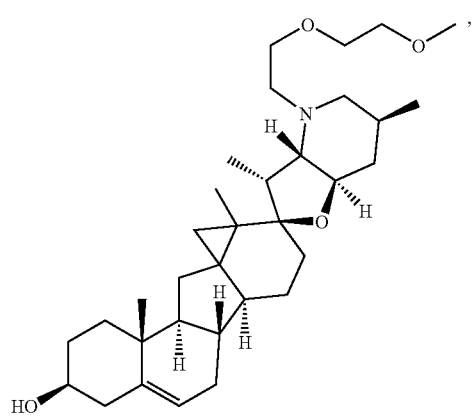
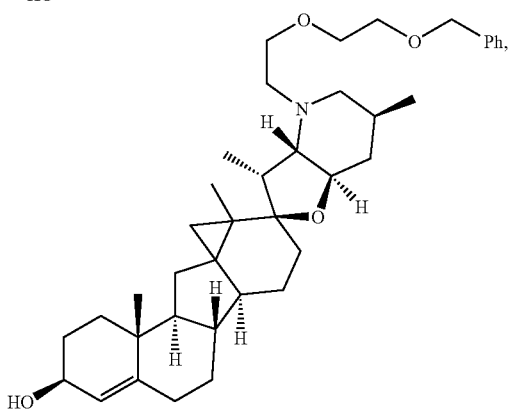
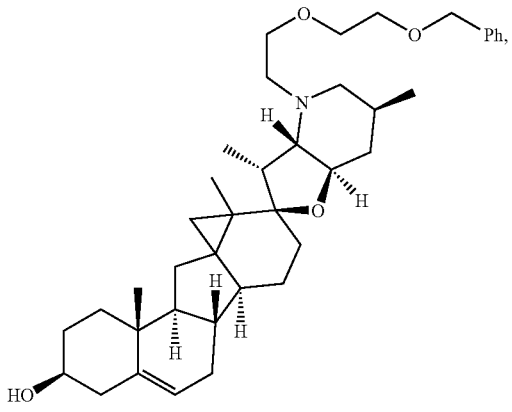
54
-continued
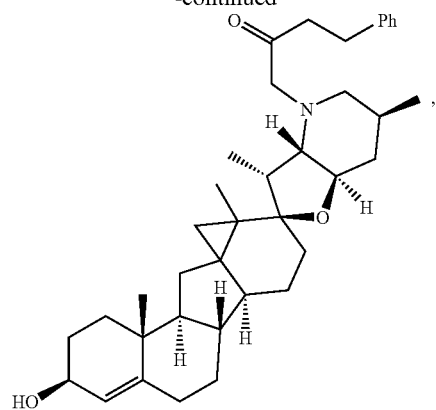
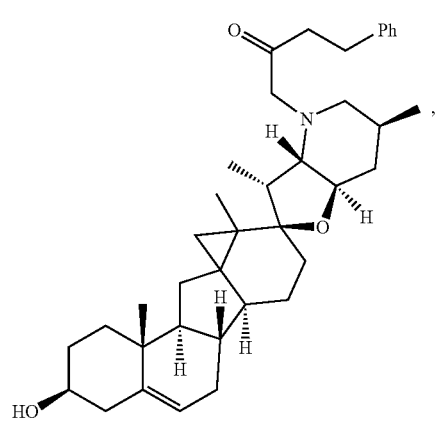
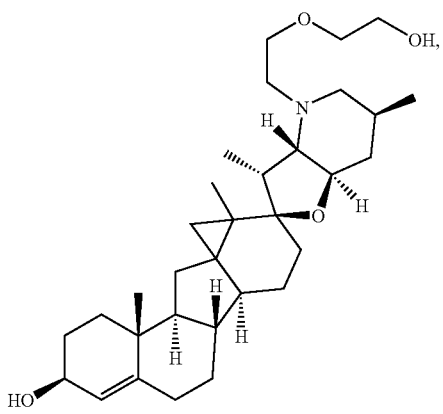
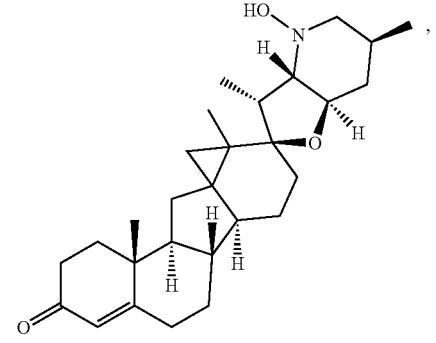

-continued

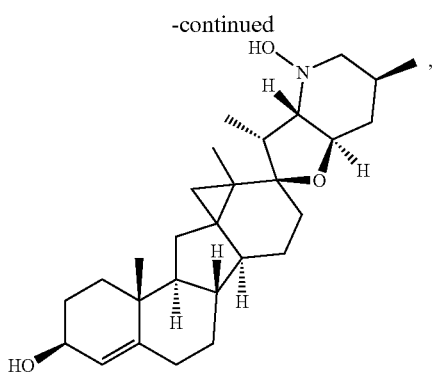

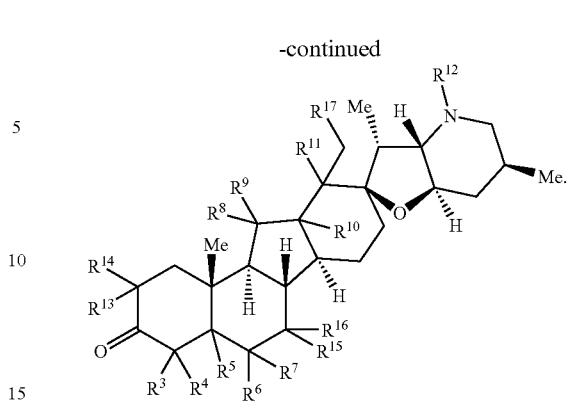

, and

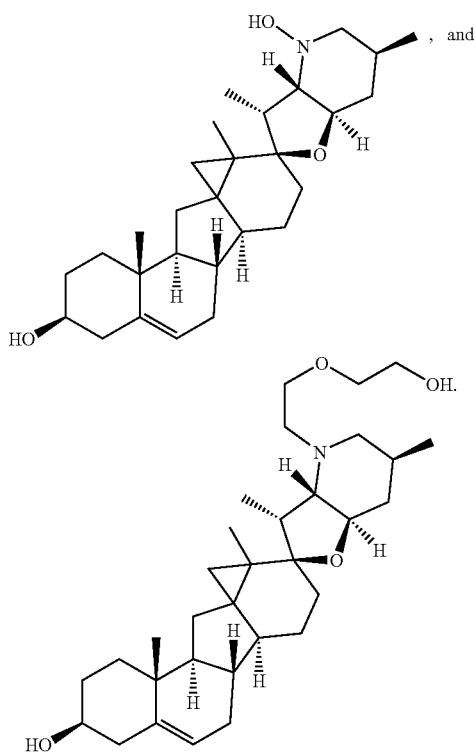

In certain embodiments, the compounds of the present invention are represented by any of the aforementioned compounds and the attendant definitions, wherein the compound is represented by the formula:

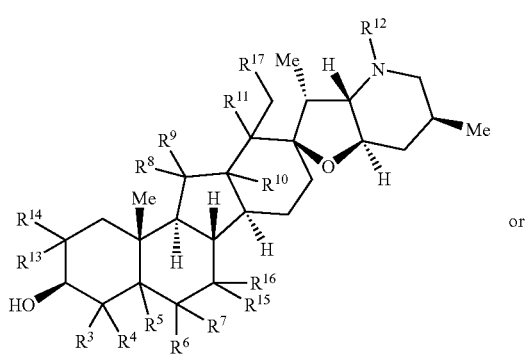

or

-continued

In certain embodiments, the present invention relates to a pharmaceutical composition comprising any one or more of the aforementioned compounds; and a pharmaceutically acceptable excipient.

Synthesis of Steroidal Alkaloid Compounds

The cyclopropyl steroidal alkaloid derivatives of the present invention can be prepared directly from a steroidal alkaloid isolated as a natural product (or synthesized) or N-protected forms of these compounds. Suitable nitrogen protecting groups include, but are not limited to Fmoc, Alloc, Boc, Troc, trifluoroacetate, Tosyl, Cbz, ethyl cyanide, and Bn.

A variety of cyclopropanating agents can be used to cyclopropanate the steroidal alkaloid. 1,1-Haloalkylmetal complexes, including reactive species referred to as carbenoids, are commonly used to cyclopropanate olefins. These reagents are typically made using a diiodoalkane or diazoalkane and a metal or organometalic species such as $Et_2Zn$, $iBu_3Al$, samarium, copper, rhodium, or palladium. In certain embodiments, $Et_2Zn$ and diiodomethane are used to affect the cyclopropanation. Other known cyclopropanation methods such as those utilizing sulfur ylides to react with an olefin conjugated to a carbonyl to add a $CH_2$ or CH-alkyl or CH-aryl group, and metal-catalyzed decomposition of diazoalkyl and α-diazo-carbonyl compounds, such as diazomethane and ethyl diazoacetate, can also be used: these methods readily provide cyclopropanes having alkyl, aryl, alkoxycarbonyl (—COOR), or acyl substituents. For example, the addition of ethyl diazopropionate ($EtO_2C$—C($N_2$)-Me) to an olefinic compound in an organic solvent containing a metal catalyst such as copper or palladium results in formation of a cyclopropane containing a group represented by formula 1b wherein Z represents $C(R^{23})_2$, in which one $R^{23}$ is Me and the other $R^{23}$ is COOEt.

By carefully selecting the cyclopropanating agent, site selectivity can be achieved in the cyclopropanation of steroidal alkaloids with more than one olefin. For example, if diiodomethane and $Et_2Zn$ are used to cyclopropanate jervine under certain conditions only the more electron rich olefin will react.

The diastereoselectivity of the cyclopropanation can be controlled in a number of ways. For example, lowering the temperature of the cyclopropanation reaction can lead to higher diastereoselectivities. Alternatively, a chiral cyclopropanating agent can be used that can distinguish between each diastereo-face of the steroidal alkaloid. Facial selectivity in the cyclopropanation can also be achieved by using substrate directed reactions (i.e. cyclopropanation of allylic alcohols using $Et_2Zn/CH_2I_2$ reagents).

The cyclopropanation reactions may be conducted in an aprotic solvent, preferably one in which the reaction ingredients are substantially soluble. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, and the like; aliphatic or aromatic hydrocarbon solvents, such as benzene, xylene, toluene, hexane, pentane and the like; esters and ketones, such as ethyl acetate, acetone, and 2-butanone; polar aprotic solvents, such as acetonitrile, dimethylsulfoxide, dimethylformamide, and the like; or combinations of two or more solvents. In a preferred embodiment, dichloromethane is the solvent used for the cyclopropanation when a dialkyl zinc and diiodomethane is used.

Following synthesis of the cyclopropanated steroidal alkaloid core, the compound may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

In the presence of Lewis or Bronsted acids the cyclopropyl cyclopamine analogs of the present invention undergo a hereto unobserved rearrangement and ring expansion to afford novel cyclopamine analogs in which the D ring has been expanded by one carbon. The cyclopropyl ring may be substituted or unsubstituted. In cases where the cyclopropyl ring is substituted, the groups attached to the methylene of the cyclopropane will be installed onto the D ring after rearrangement and ring expansion. Suitable acids include, but are not limited to $ZnI_2$, $BF_3$, methanesulfonic acid, diaryloxyphosporic acids, and HCl. In a preferred embodiment of the invention the Lewis acid used is $BF_3$. These homologated analogs may be further functionalized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

Methods of the Invention

The present invention further provides methods for treating, ameliorating one or more of the symptoms of, and reducing the severity of hyperproliferative disorders, i.e. cancer, as well as other hedgehog pathway mediated disorders or conditions.

Hedgehog pathway antagonists are currently being explored in a large number of clinical conditions where a therapeutic effect can be obtained for a condition or disorder by inhibiting one or more aspects of Hedgehog pathway activity. Although the primary focus has been on cancer, investigators have found that small molecule inhibition of the hedgehog pathway ameliorates the symptoms of psoriasis (Tas, et al., 2004 Dermatology 209: 126–131, published US patent application 20040072913 (herein incorporated by reference)). Psoriasis is a very common, chronic skin disorder typically characterized by skin lesions usually containing erythematous papules and plaques with a silver scale, although there are variations both on the skin and in other parts of the body. Psoriasis is currently thought to be an autoimmune disease but its etiology is still poorly understood. In one study, topical application of cyclopamine to psoriasis lesions led to full or partial regression of the lesion with a decrease in inflammatory cells (Tas et al., supra).

The hedgehog pathway antagonists of the present invention may be used to treat or prevent psoriasis when administered as a single agent or when administered in combination with one or more other anti-psoriasis agents including, but not limited to, corticosteroids, tar, calcipotriene, tazarotene, calcineurin inhibitors, ultraviolet irradiation, methotrexate, retinoids, cyclosporine, immunomodulatory drugs, etanercept, alefacept, efalizumab, and infliximab.

Many tumors and proliferative conditions have been shown to depend on the hedgehog pathway. The growth of such cells and survival can be affected by treatment with the compounds of the present invention. For example, small molecule inhibition of the hedgehog pathway has been shown to inhibit the growth of basal cell carcinoma (Williams, et al., 2003 PNAS 100: 4616–21), medulloblastoma (Berman et al., 2002 Science 297: 1559–61), pancreatic cancer (Berman et al., 2003 Nature 425: 846–51), gastrointestinal cancers (Berman et al., 2003 Nature 425: 846–51, published PCT application WO 05/013800), esophageal cancer (Berman et al., 2003 Nature 425: 846–51), lung cancer (Watkins et al., 2003. Nature 422: 313–7), and prostate cancer (Karhadkar et al., 2004. Nature 431: 707–12).

In addition, it has been shown that many cancer types have uncontrolled activation of the hedgehog pathway, for example, breast cancer (Kubo et al., 2004. Cancer Research 64: 6071–4), heptacellular cancer (Patil et al., 2005. $96^{th}$ Annual AACR conference, abstract #2942 Sicklick et al., 2005. ASCO annual meeting, abstract #9610), hematological malignancies (Watkins and Matsui, unpublished results), basal carcinoma (Bale & Yu, 2001. Human Molec. Genet. 10:757–762 Xie et al., 1998 Nature 391: 90–92), medulloblastoma (Pietsch et al., 1997. Cancer Res. 57: 2085–88), and gastric cancer (Ma et al., 2005 Carcinogenesis May 19, 2005 (Epub)).

Cancers or neoplastic diseases and related disorders that can be treated by administration of compounds and compositions of the present invention, include, but are not limited to Adrenal Cortical Cancer, Anal Cancer, Aplastic Anemia, Bile Duct Cancer, Bladder Cancer, Bone Cancer, Brain/CNS Tumors, Breast Cancer, Cervical Cancer, Non-Hodgkin's Lymphoma, Colon Cancer, Rectum Cancer, Endometrial Cancer, Esophagus Cancer, Ewing's Family of Tumor, Eye Cancer, Gallbladder Cancer, Gastrointestinal Carcinoid Tumors, Gastrointestinal Stromal Tumors, Gestational Trophoblastic Disease, Hodgkin's Disease, Kaposi's Sarcoma Kidney Cancer, Laryngeal and Hypopharyngeal Cancer, Acute Lymphocytic Leukemia, Acute Myeloid Leukemia, Children's Leukemia, Chronic Lymphocytic Leukemia, Chronic Myeloid Leukemia, Liver Cancer, Lung Cancer, Lung Carcinoid Tumor, Non-Hodgkin's type Lymphoma, Male Breast Cancer, Malignant Mesothelioma, Multiple Myeloma, Myelodysplastic Syndrome, Nasal Cavity and Paranasal Cancer, Nasopharyngeal Cancer, Neuroblastoma, Oral Cavity Cancer, Oropharyngeal Cancer, Osteosarcoma, Ovarian Cancer, Pancreatic Cancer, Penile Cancer, Pituitary Tumor, Prostate Cancer, Retinoblastoma, Rhabdomyosarcoma, Salivary Gland Cancer, Sarcoma, Melanoma Skin Cancer, Nonmelanoma Skin Cancer, Stomach Cancer, Testicular Cancer, Thymus Cancer, Thyroid Cancer, Uterine Sarcoma, Vaginal Cancer, Vulvar Cancer, Waldenstrom's Macroglobulinemia, and Wilms' Tumor.

The methods and compositions of the present invention can be used in the treatment of human cancers, for example basal cell carcinomas and other tumors of epithelial tissues such as the skin. Additionally, compounds of the present invention can be employed as part of a treatment basal cell carcinoma, pancreatic cancer, prostate cancer, sarcoma, lymphomas, leukemia, gastrointestinal cancer, multiple myeloma, small cell lung cancer, glioma, breast cancer, hepatocellular, or medulloblastoma by administering a therapeutically effective amount of at least one of the compounds of the present invention as a single agent or in combination with another anti-cancer agent.

The methods and compositions of the present invention can be used in the treatment of neoplastic or hyperplastic transformations such as may occur in the central nervous system. For instance, the compounds of the present invention can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In one embodiment, the present method can be used as part of a treatment regimen for malignant medulloblastoma and other primary CNS malignant neuroectodermal tumors.

In certain embodiments, the present invention relates to a method of treating cancer, comprising administering to a subject in need thereof a therapeutically effective amount of one or more of any of the aforementioned compounds.

In certain embodiments, the present invention relates to a method of treating cancer, comprising administering to a subject in need thereof a therapeutically effective amount of a compound of any one or more of the aforementioned compounds, wherein the cancer is located in the subjects head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain.

In certain embodiments, the present invention relates to a method of treating cancer, comprising administering to a subject in need thereof a therapeutically effective amount of a compound of one or more of any of the aforementioned compounds, wherein the cancer is basal cell carcinoma, pancreatic cancer, prostate cancer, sarcoma, lymphomas, leukemia, gastric cancer, esophageal cancer, biliary cancer, colon cancer, multiple myeloma, small cell lung cancer, glioma, breast cancer, hepatocellular, or medulloblastoma.

In certain embodiments, the present invention relates to the aforementioned method wherein the compound is used in combination with radiation therapy or another anti-cancer chemotherapeutic agent.

In certain embodiments, the present invention relates to any aforementioned method wherein the compound is administered locally to a tumor or systemically to a patient.

In certain embodiments, the present invention relates to any aforementioned method wherein the mode of administration of said compound is inhalation, oral, intravenous, sublingual, ocular, transdermal, rectal, vaginal, topical, intramuscular, intra-arterial, intrathecal, subcutaneous, buccal, or nasal.

In certain embodiments, the present invention relates to any aforementioned method wherein the mode of administration is oral, intravenous, or topical.

In certain embodiments, the present invention relates to a method for antagonizing the hedgehog pathway in a cell, comprising contacting a cell expressing smoothened with an effective amount of any one or more of the aforementioned compounds.

In certain embodiments, the present invention relates to a method for antagonizing the hedgehog pathway in a cell, comprising contacting a cell expressing smoothened with an effective amount of any one or more of the aforementioned compounds, wherein said cell expressing smoothened is contacted with said compound in vitro.

In certain embodiments, the present invention relates to a method for antagonizing the hedgehog pathway in a cell, comprising contacting a cell expressing smoothened with an effective amount of any one or more of the aforementioned compounds, wherein said cell expressing smoothened is contacted with said compound in vivo.

In certain embodiments, the present invention relates to a method for antagonizing the hedgehog pathway in a cell, comprising contacting a cell expressing smoothened with an effective amount of any one or more of the aforementioned compounds, wherein said cell expressing Smo is within the body of a patient.

In certain embodiments, the present invention relates to a method of treating or preventing psoriasis in a subject, comprising administering to a subject in need thereof a therapeutically effective amount of any one or more of the aforementioned compounds.

In certain embodiments, the present invention relates to the aforementioned method of treating or preventing psoriasis wherein the mode of administration of said compound is topical.

In certain embodiments, one or more compounds of the present invention are used to treat or prevent psoriasis in combination with one or more anti-psoriasis agents including, but not limited to, corticosteroids, tar, calcipotriene, tazarotene, calcineurin inhibitors, ultraviolet irradiation, methotrexate, retinoids, cyclosporine, immunomodulatory drugs, etanercept, alefacept, efalizumab, and infliximab.

Treatment of Cancer in Combination with Chemotherapy or Radiotherapy

In certain embodiments, one or more compounds of the present invention are used to treat or prevent cancer or neoplastic disease in combination with one or more anti-cancer, chemotherapeutic agents including, but not limited to, gemcitabine, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, one or more compound of the present invention is used to treat or prevent cancer or neoplastic disease in combination with one or more chemotherapeutic or other anti-cancer agents including, but not limited to radiation (e.g. γ-radiation), nitrogen mustards (e.g. cyclophosphamide, Ifosfamide, Trofosfamide, Chlorambucil, Estramustine, and Melphalan), Nitrosoureas (e.g. carmustine (BCNU) and Lomustine (CCNU)), Alkylsulphonates (e.g. busulfan and Treosulfan), Triazenes (e.g. Dacarbazine and Temozolomide), Platinum containing compounds (e.g. Cisplatin, Carboplatin, and oxaliplatin), Vinca alkaloids (e.g. vincristine, Vinblastine, Vindesine, and Vinorelbine), Taxoids (e.g. paclitaxel and Docetaxol), Epipodophyllins (e.g. etoposide, Teniposide, Topotecan, 9-Aminocamptothecin, Camptoirinotecan, Crisnatol, Mytomycin C, and Mytomycin C), Anti-metabolites, DHFR inhibitors (e.g. methotrexate and Trimetrexate), IMP dehydrogenase Inhibitors (e.g. mycophenolic acid, Tiazofurin, Ribavirin, and EICAR), Ribonucleotide reductase Inhibitors (e.g. hydroxyurea and Deferoxamine), Uracil analogs (e.g. Fluorouracil, Floxuridine, Doxifluridine, Ratitrexed, and Capecitabine), Cytosine analogs (e.g. cytarabine (ara C), Cytosine arabinoside, and Fludarabine), Purine analogs (e.g.

mercaptopurine and Thioguanine), Anti-estrogens (e.g. Tamoxifen, Raloxifene, and Megestrol), LHRH agonists (e.g. goscrclin and Leuprolide acetate), Anti-androgens (e.g. flutamide and Bicalutamide), Vitamin D3 analogs (e.g. EB 1089, CB 1093, and KH 1060), Photodyamic therapies (e.g. vertoporfin (BPD-MA), Phthalocyanine, photosensitizer Pc4, and Demethoxy-hypocrellin A (2BA-2-DMHA)), Cytokines (e.g. Interferon α, Interferon γ, and Tumor necrosis factor), Isoprenylation inhibitors (e.g. Lovastatin), Dopaminergic neurotoxins (e.g. 1-methyl-4-phenylpyridinium ion), Cell cycle inhibitors (e.g. staurosporine), Actinomycins (e.g. Actinomycin D and Dactinomycin), Bleomycins (e.g. bleomycin A2, Bleomycin B2, and Peplomycin), Anthracyclines (e.g. daunorubicin, Doxorubicin (adriamycin), Idarubicin, Epirubicin, Pirarubicin, Zorubicin, and Mitoxantrone), MDR inhibitors (e.g. verapamil), $Ca^{2+}$ ATPase inhibitors (e.g. thapsigargin), Antibodies (e.g. Avastin, Erbitux, Rituxan, and Bexxar), corticosteroids (e.g. prednilone, predisone, etc), Imatinib, Thalidomide, Lenalidomide, Bortezomib, Gemcitabine, Erlotinib, Gefitinib, Sorafenib, and Sutinib.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents, and observed adverse affects.

Also, in general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with a compound of the present invention.

If a compound of the present invention and the chemotherapeutic agent and/or radiation are not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

Pharmaceutical Compositions

In another embodiment, the present invention provides pharmaceutically acceptable compositions which comprise a therapeutically-effective amount of one or more of the compounds described above (Formula 1 and 2), formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) pulmonarily, or (9) nasally. As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Pharmaceutical compositions of the present invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the compounds of the present invention in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of the present invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The subject receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutical effects of the first administered, one is not entirely disappeared when the subsequent is administered.

Exemplification

The invention now being generally described, it will be more readily understood by reference to the following examples, which are included merely for purposes of illustration of certain aspects and embodiments of the present invention, and are not intended to limit the invention.

EXAMPLE 1

Preparation of a Derivative of Cyclopamine

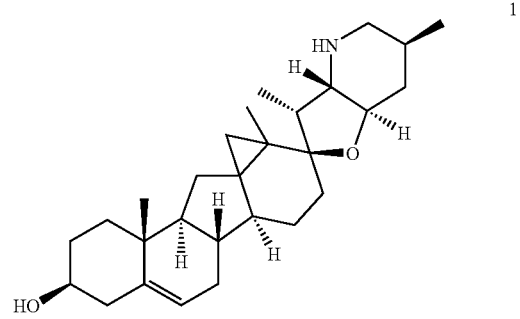

Part A

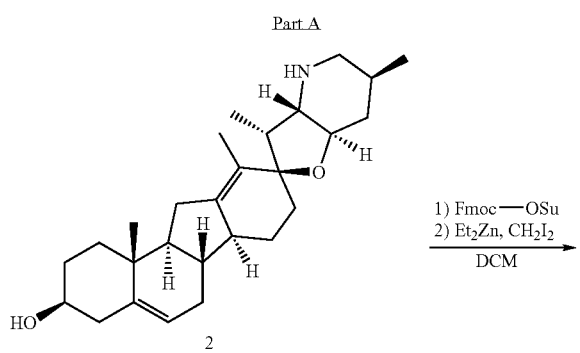

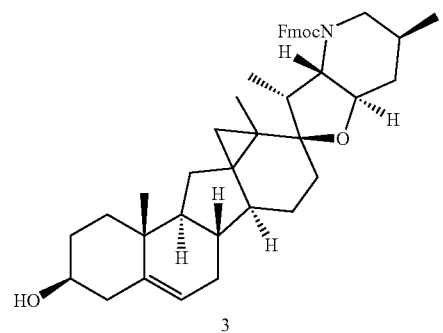

To a solution of cyclopamine 2 (250 mg, 0.6 mmol, 1 eq) in DCM (10 mL) at rt was added Fmoc-OSu (205 mg, 0.6 mmol, 1 eq) and the resulting mixture was stirred at rt overnight. The resulting solution of crude Fmoc-cyclopamine was then cooled to 0° C. and was treated with 15% diethylzinc in toluene (0.5 mL, 0.6 mmol, 1 eq) and stirred for 30 min (Flask A).

Diiodomethane (0.4 mL, 6 mmol, 10 eq) in DCM (20 mL) at 0° C. was treated with 15% diethylzinc in toluene (3 mL, 3 mmol, 5 eq) and the resulting solution was stirred for 5 min (Flask B).

The contents of Flask B were transferred to Flask A via cannula and the resulting suspension was stirred for 5 h at rt. The reaction was quenched with HCl (1 M), stirred for 10 min (until all white solid redissolved) and extracted with DCM (5×). The organic extracts were dried (MgSO$_4$), filtered over Celite and concentrated in vacuo. The residue was purified by flash chromatography (1:1 Hex/AcOEt). The target 11,12-monocyclopropane was obtained as a 9:1 mixture of diastereoisomers, along with 20% of diastereomeric bis-cyclopropanated products (80% total recovery). This mixture was separated using preparative SFC chromatography

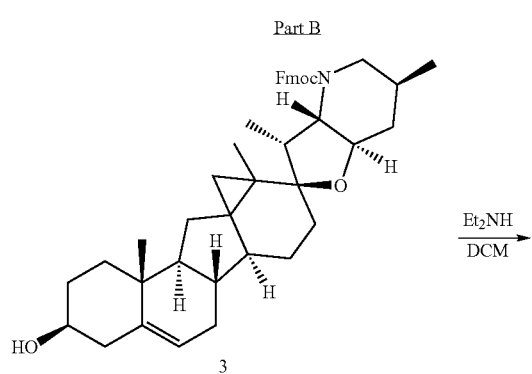

Fmoc-monocyclopropyl cyclopamine 3 (100 mg, 0.15 mmol, 1 eq) in DCM (2 mL) at rt was treated with diethylamine (0.5 mL, 4.8 mmol, 32 eq) overnight, the resulting solution was concentrated in vacuo and the residue absorbed on silica gel and purified by flash chromatography (2:14→1:1 Hex/AcOEt, and then 95:5→90:10→20:80 DCM/MeOH). The desired product was obtained as a white solid (95% yield). MS (ESI(+)) m/e 426.31 (M+H)$^+$.

EXAMPLE 2

Preparation of a Derivative of Cyclopamine

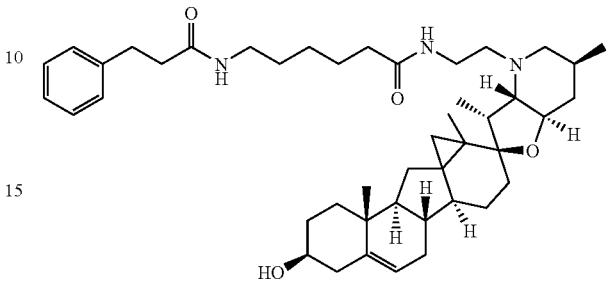

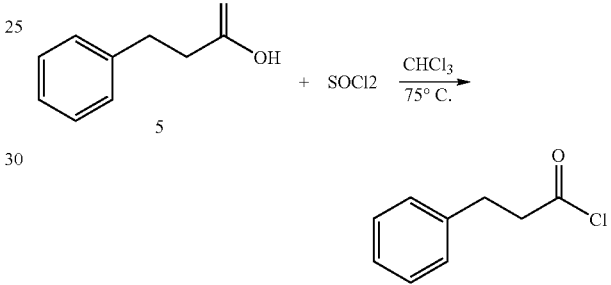

To a solution of hydrocinnamic acid 5 (3.01 g, 20 mmol, 1 eq) in anhydrous chloroform (30 mL) at 75° C. was added thionyl chloride (1.75 mL, 24.1 mmol, 1.2 eq) dropwise over a period of 3 min. The mixture was refluxed for 3.5 h. The solvent was distilled off to give the crude acid chloride as a light yellow viscous liquid. The crude was used without further purification.

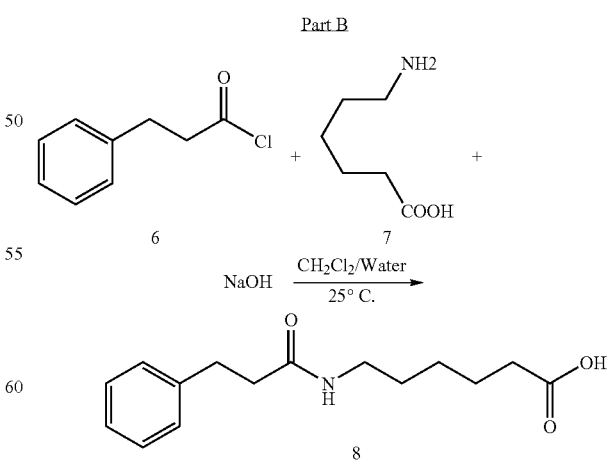

To a biphasic mixture of 7 (3.16 g, 24.1 mmol, 1.2 eq) in DCM (30 mL) and an aqueous solution of NaOH (2.0 M, 30 mL, 3 eq) at 25° C. was added a solution of the acid chloride 6 (3.38 g, 20 mmol, 1 eq) in DCM (10 mL) and the resulting mixture was stirred at 25° C. for 3 h. The mixture was then neutralized with aqueous HCl (2 M, 30 mL). The organic layer was then separated and the aqueous layer was extracted with DCM (3×50 mL). The combined organic layers were washed with HCl (2.0 M, 25 mL), water (3×50 mL), saturated brine (50 mL), dried over magnesium sulfate and the solvent was evaporated under reduced pressure. The crude was chromatographed on silica gel using 5% MeOH:DCM as eluant and the column was then eluted with 10% MeOH:DCM to yield 1.141 g of compound 8.

Part C

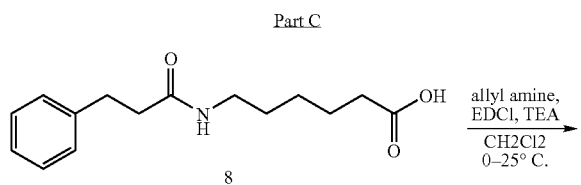

8 allyl amine, EDCl, TEA
CH2Cl2
0–25° C.

-continued

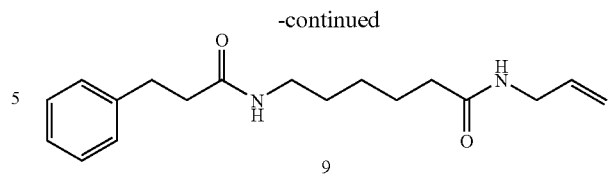

9

To a mixture of the acid 8 (264 mg, 1 mmol, 1 eq), EDCI (231 mg, 1.2 mmol, 1.2 eq), and triethyl amine (168 µL 1.2 mmo, 1.2 eq) in DCM (2 mL) at 0° C. was added allylamine (90.3 µL, 1.2 mmol, 1.2 eq), and the resulting mixture was stirred at 0° C. for 1 h and allowed to warm to 25° C. over a period of 2 h. The reaction mixture was added to water (50 mL), extracted with DCM (4×25 mL), the combined organic layers were washed with 1 M HCl (2×25 mL), water (3×25 mL), satd brine (25 mL), dried over magnesium sulfate and the solvent was evaporated off under reduced pressure to yield 287.5 mg of the desired product. This material was used without further purification.

Part D

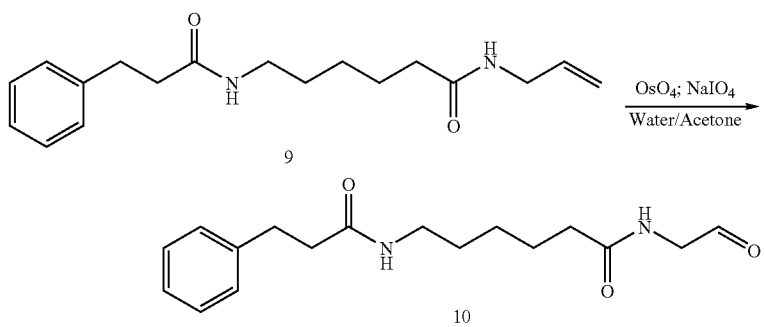

To a solution of the allyl amide 9 (70 mg, 0.23 mmol, 1 eq) in acetone (1 mL) and water (0.3 mL) was added a solution of osmium tetroxide (0.35 mL, 0.035 mmol, 0.15 eq, 2.5 w/w in t-butanol). The reaction mixture was immediately cooled in ice soon after the addition of the $OsO_4$ solution and the resulting dark brown solution was stirred at 0° C. for 15 min. Sodium periodate (110 mg, 0.51 mmol, 2.2 eq) was added in 5 portions to the above mixture and stirring continued for 1 h at 0° C. and allowed to warm to 25° C. over a period of 2 h. The reaction mixture was diluted with DCM (3 mL), filtered through a short plug of magnesium sulfate and the filter cake was washed with DCM (4×3 mL). The filtrate was concentrated and the residue (67.9 mg) was filtered through a short plug of RP silica gel using 5% MeOH:DCM to yield 38.9 mg of the desired product.

Part E

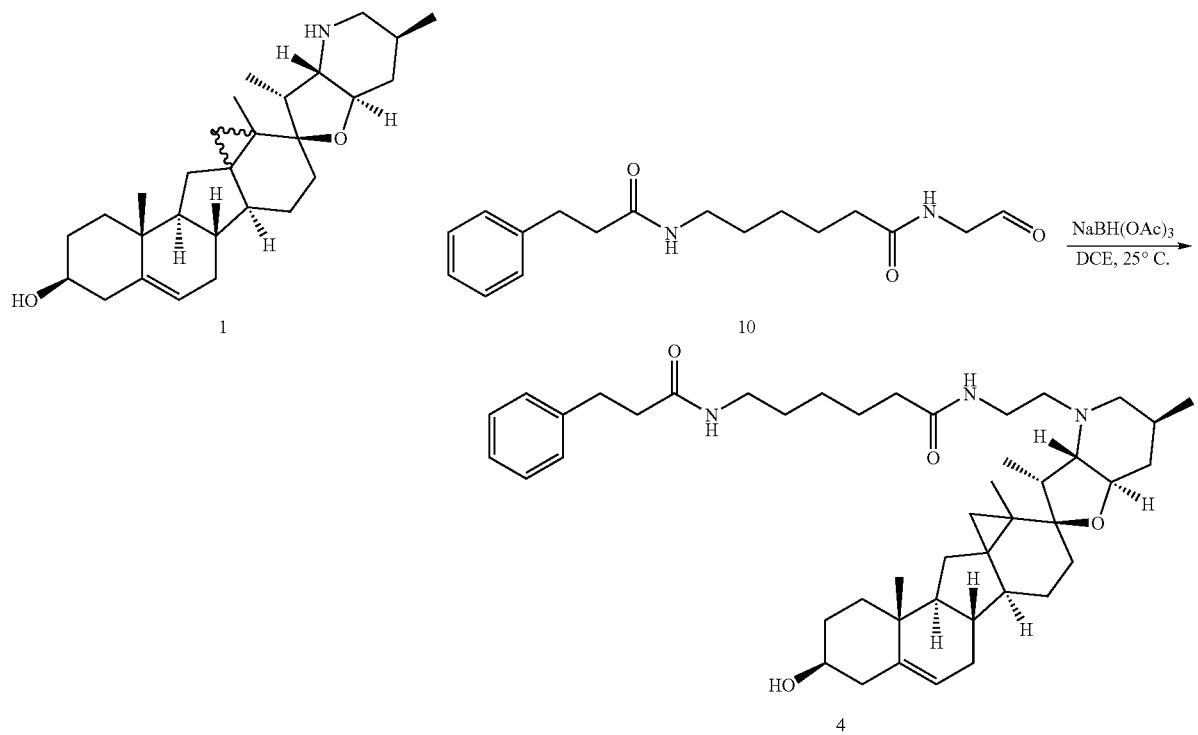

To a suspension of the 1 (10 mg, 0.023 mmol, 1 eq) in acetonitrile (2 mL) was added a solution of the aldehyde 10 (17 mg, 0.056 mmol, 2.4 eq) in acetonitrile (0.3 mL) followed by sodium triacetoxy borohydride (6.5 mg, 0.031 mmol, 1.3 eq) and the reaction mixture was stirred at 25° C. for 16 h. The solvent was then evaporated under reduced pressure and the residue was chromatographed on silica gel (7 cm×10 mm) using 3% Methanol:DCM to yield 24.6 mg of crude material. This material was re-subjected to column chromatography on silica gel using 2% MeOH:DCM and recovered 18.2 mg of an impure product which was further purified by preparation TLC using 3% MeOH:DCM as the developing solvent (2 run) to yield 6.3 mg of the desired product. MS (ESI(+)) m/e 714.4 (M+H)+.

EXAMPLE 3

Preparation of a Derivative of Cyclopamine

Part A

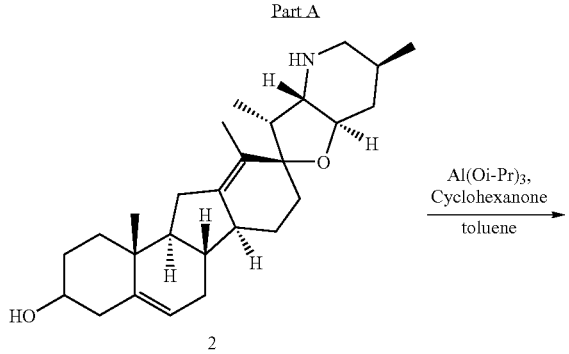

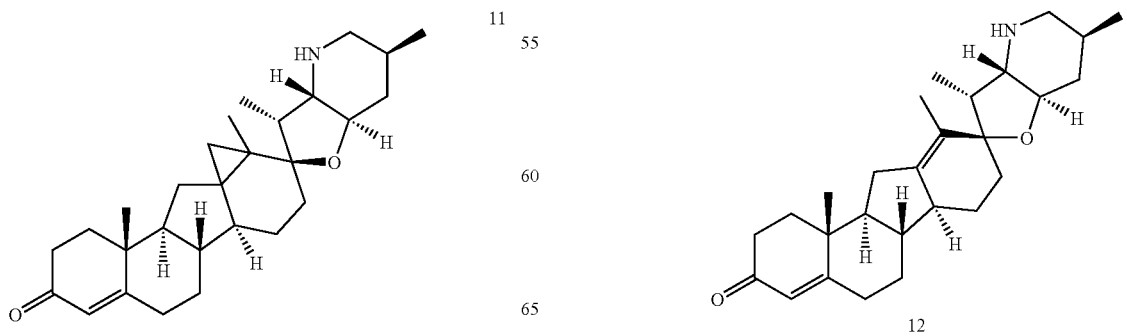

Cyclopamine 2 (20 mg, 0.049 mmol, 1 eq) was suspended in dry toluene (0.6 mL) and cyclohexanone (150 μL, 1.47 mmol, 30 eq) followed by aluminum isopropoxide (79 mg, 0.392 mmol, 8 eq) were added. The resulting mixture was heated to reflux for 2 h, cooled to rt, diluted with AcOEt and quenched with Rochelle's salt solution. The biphasic mixture was stirred overnight, the layers were separated, the aqueous extracted with AcOEt and the combined organic extracts dried (MgSO$_4$), filtered and concentrated in vacuo. The residue was purified by flash chromatography (DCM, DCM/MeOH 98:2 and 95:5). The target was obtained as a white crystalline solid (70% yield).

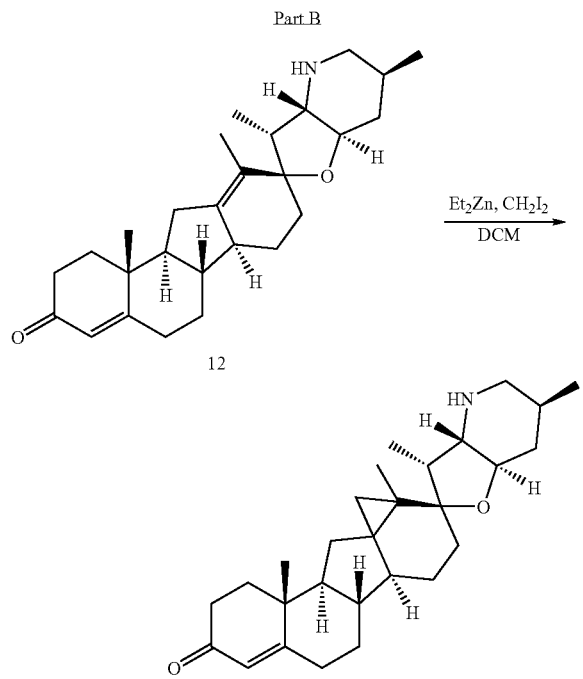

Diiodomethane (40 μL, 0.5 mmol, 25 eq) in DCM (0.52 mL) at 0° C. was treated with 15% diethylzinc in toluene (0.2 mL, 0.2 mmol, 10 eq) and the resulting solution was stirred for 5 min. Compound 12 (10 mg, 0.02 mmol, 1 eq) in DCM (0.35 mL) was added and the resulting mixture stirred at rt (ice bath removed) for 3 h, quenched with 2 N NaOH and stirred for 10 min, the layers separated and the aqueous one extracted with DCM (2×). The organic extracts were dried (MgSO4), filtered and concentrated in vacuo. The residue was purified by flash chromatography (DCM/MeOH 92:8). The cyclopropanated material was obtained as a white solid. MS (ESI(+)) m/e 424.5 (M+H)$^+$.

EXAMPLE 4

Preparation of a Derivative of Cyclopamine

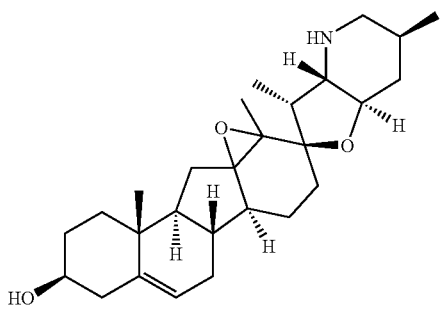

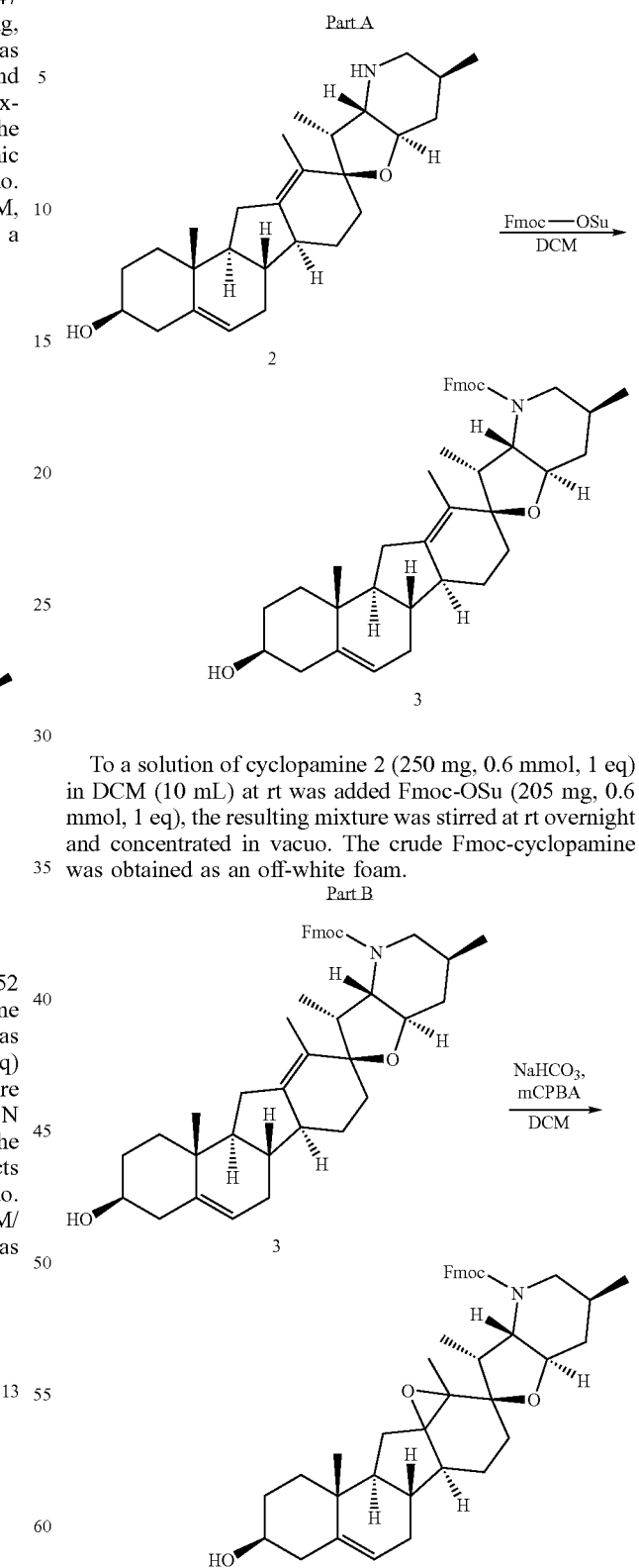

To a solution of cyclopamine 2 (250 mg, 0.6 mmol, 1 eq) in DCM (10 mL) at rt was added Fmoc-OSu (205 mg, 0.6 mmol, 1 eq), the resulting mixture was stirred at rt overnight and concentrated in vacuo. The crude Fmoc-cyclopamine was obtained as an off-white foam.

Part B

A solution of crude Fmoc-cyclopamine 3 (15 mg, 0.024 mmol, 1 eq) in DCM (0.5 mL) was cooled to −78° C. and treated with sodium hydrogencarbonate (4 mg, 0.047 mmol, 1.96 eq) followed by mCPBA (4 mg, 0.024 mmol, 1 eq). The reaction mixture was stirred at −78° C. for 1 h, diluted with H₂O and extracted with DCM (3×). The organic extracts were washed with 10% NaHCO₃ and brine, dried (MgSO₄), filtered and concentrated in vacuo. The crude material was purified by preparative TLC (Hex/AcOEt 1:2) to yield the epoxide as a white foam (70% yield).

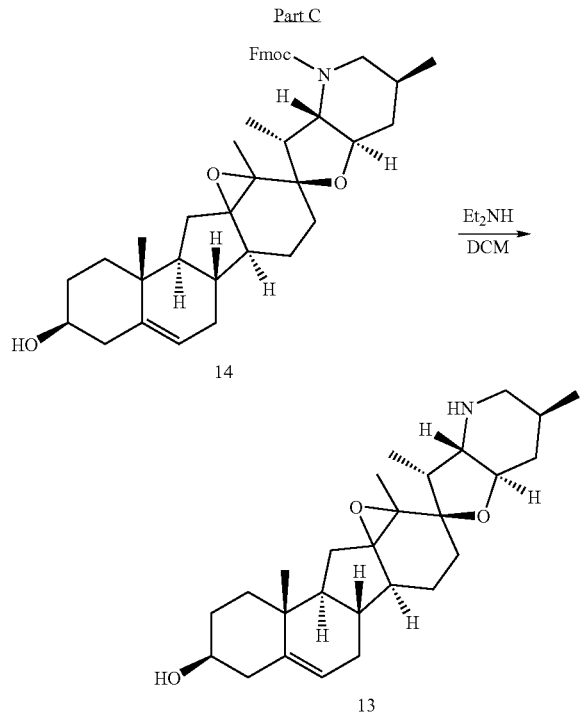

A solution of compound 14 (11 mg, 0.017 mmol, 1 eq) in DCM (0.5 mL) was treated at rt with Et₂NH (0.5 mL, 4.8 mmol, 282 eq), the resulting solution was stirred at rt overnight and concentrated in vacuo. The residue was purified by prep TLC (DCM/MeOH 9:1). Compound 13 was obtained as a white solid (90% yield). MS (ESI(+)) m/e 428.5 (M+H)⁺.

EXAMPLE 5

Preparation of a Derivative of Cyclopamine

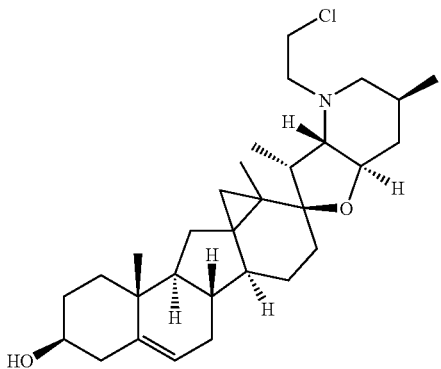

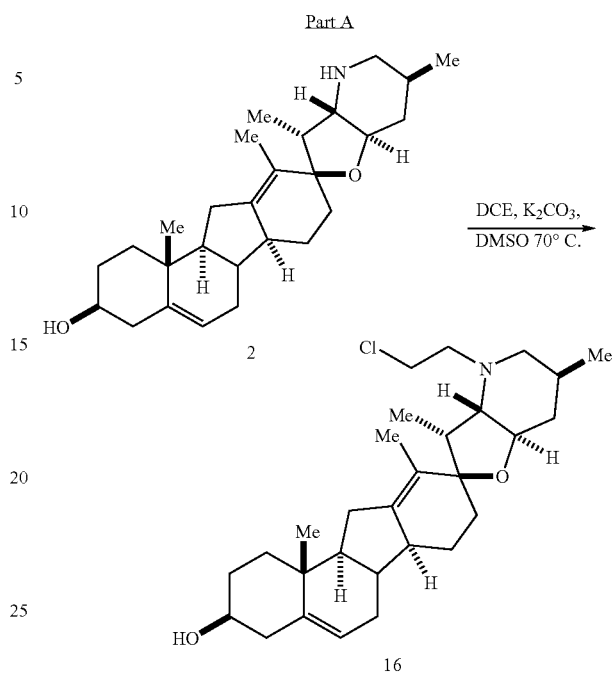

Compound 2 (1.30 g, 3.2 mmol, 1 eq) was massed out and charged into the reaction vessel. Potassium carbonate (0.91 g, 6.6 mmol, 2.1 eq) was massed out and charged into the reaction vessel followed by dichloroethane (6.0 mL, 76 mmol, 23.8 eq.) and anhydrous DMSO (5 mL). The reaction was heated to 70° C. for 36 h under a nitrogen atmosphere. The reaction was cooled to rt, diluted with DCM (15 mL) and washed twice with water (2×15 mL). The organic layer was dried over sodium sulfate, filtered (DCM rinse as necessary), and concentrated to dryness to afford a pale yellow solid. Flash chromatography (DCM/EtOAc) affords the target material as a white crystalline solid.

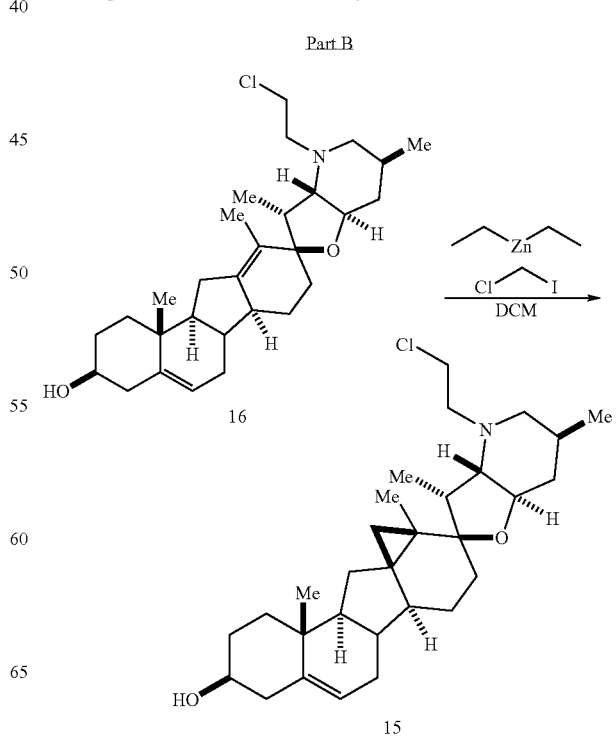

Compound 16 (0.111 g, 0.233 mmol, 1 eq) was transferred to the reaction flask, placed under a nitrogen atmosphere, and dissolved in anhydrous DCM (2 mL). Chloroiodomethane was added (0.238 mL, 3.27 mmol, 14 eq.) The solution was cooled to −15° C. Diethyl zinc (1M in heptane, 1.63 mL, 1.63 mmol, 6.5 equivalents) was added dropwise over 30 minutes carefully controlling the exotherm. The reaction was held between −10° C. and −14° C. for several hours, until TLC indicated that the starting material had been consumed. The reaction was then quenched by the careful addition of THF (6 mL) and then aqueous citrate buffer (pH 4.5, 10 mL). The layers were allowed to warm to rt. Saturated sodium sulfate (10 mL). The layers were mixed well, transferred to a seperatory funnel with excess DCM and the organic layer was collected. The organic layer was washed with aqueous sodium hydroxide (1N, 10 mL), and saturated sodium sulfate (10 mL), dried over sodium sulfate before concentrating to dryness. The crude material was purified by flash chromatography to yield the desired product in 55% yield.

EXAMPLE 6

Preparation of a Derivative of Cyclopamine

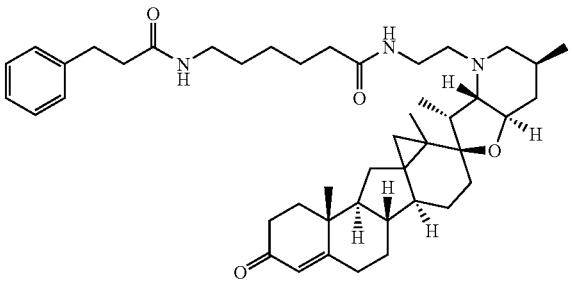

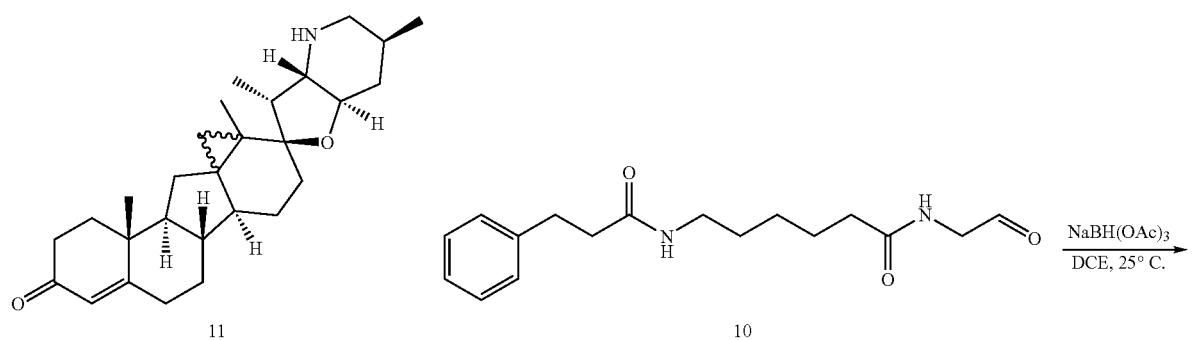

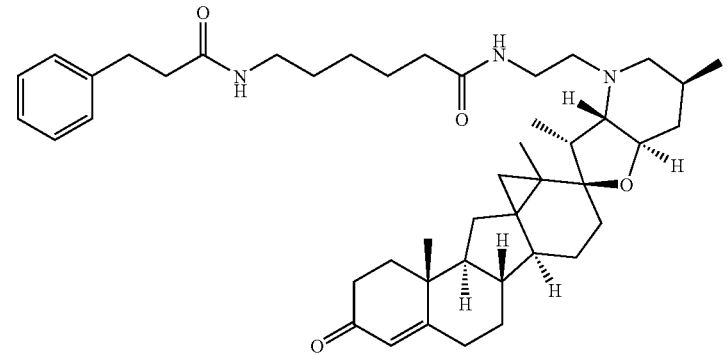

To a solution of compound 11 (5 mg, 0.01 mmol, 1 eq) and compound 10 (10 mg, 0.04 mmol, 3 eq) in anhydrous DCM (5 mL) was added solid sodium triacetoxy borohydride (8 mg, 0.04 mmol, 3 eq) and the resulting suspension was stirred at 25° C. for 2 h. The reaction mixture was quenched with sodium bicarbonate, extracted with DCM (4×10 mL), the organic layer were collected and washed with saturated brine (1×20 mL), dried over magnesium sulfate and concentrated under reduced pressure. The crude was purified by PTLC (DCM/MeOH 95:5) to yield 8 mg of the desired product.

EXAMPLE 7

Preparation of a Derivative of Cyclopamine

Cyclopamine 2 (20 mg, 0.049 mmol) was suspended in dry toluene (0.6 mL) and cyclohexanone (150 µL, 1.47 mmol, 30 eq), followed by aluminum isopropoxide (79 mg, 0.392 mmol, 8 eq), were added. The resulting mixture was heated to reflux for 2 h, cooled to rt, diluted with ethyl acetate and quenched with Rochelle's salt solution. The biphasic mixture was stirred overnight, the layers were separated, the aqueous extracted with ethyl acetate and the combined organic extracts dried (over MgSO$_4$), filtered and concentrated in vacuo. The residue was purified by flash chromatography (DCM, DCM/methanol 98:2 and 95:5). The target 12 was obtained as a white crystalline solid (70% yield).

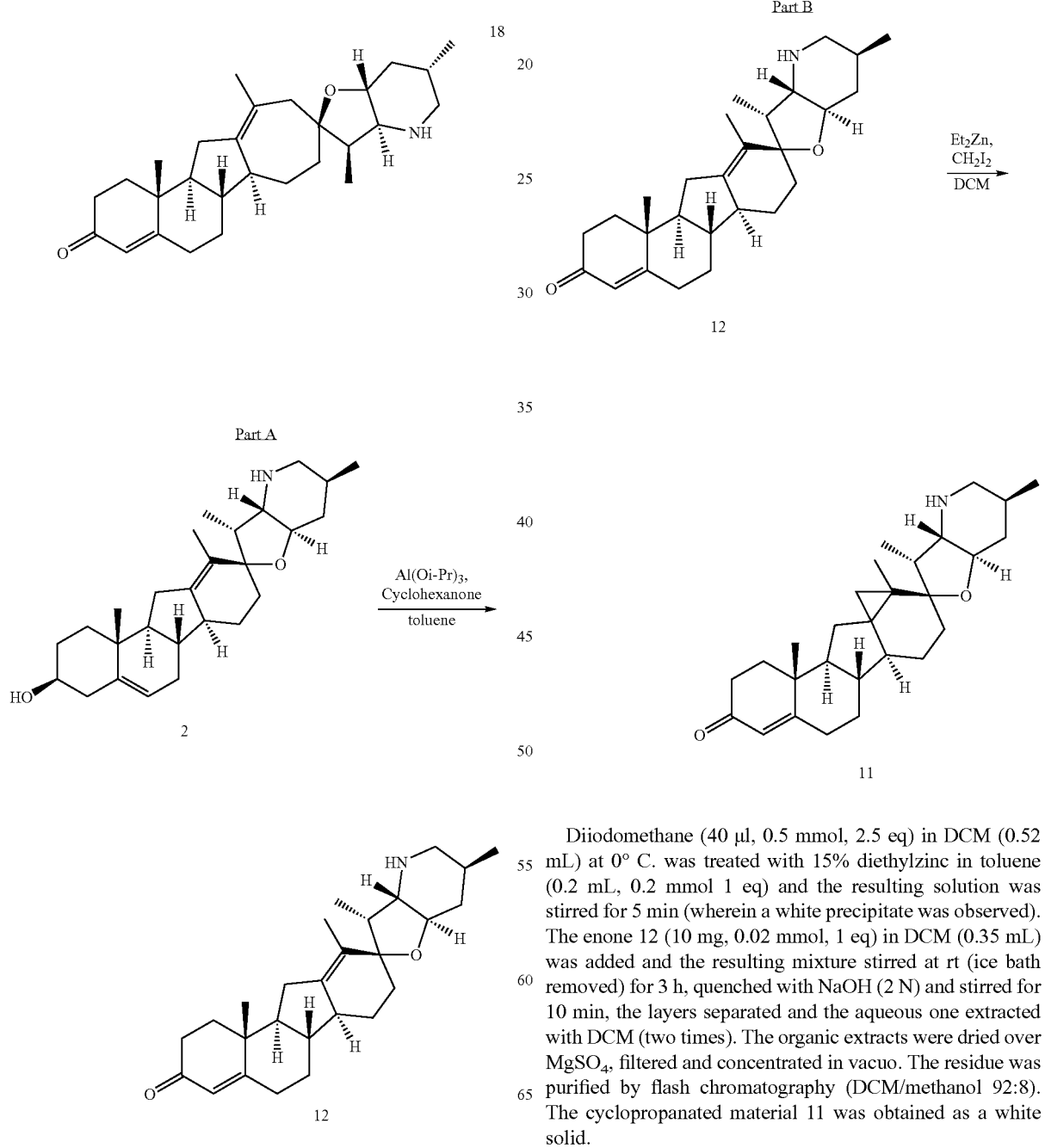

Diiodomethane (40 µl, 0.5 mmol, 2.5 eq) in DCM (0.52 mL) at 0° C. was treated with 15% diethylzinc in toluene (0.2 mL, 0.2 mmol 1 eq) and the resulting solution was stirred for 5 min (wherein a white precipitate was observed). The enone 12 (10 mg, 0.02 mmol, 1 eq) in DCM (0.35 mL) was added and the resulting mixture stirred at rt (ice bath removed) for 3 h, quenched with NaOH (2 N) and stirred for 10 min, the layers separated and the aqueous one extracted with DCM (two times). The organic extracts were dried over MgSO$_4$, filtered and concentrated in vacuo. The residue was purified by flash chromatography (DCM/methanol 92:8). The cyclopropanated material 11 was obtained as a white solid.

Part C

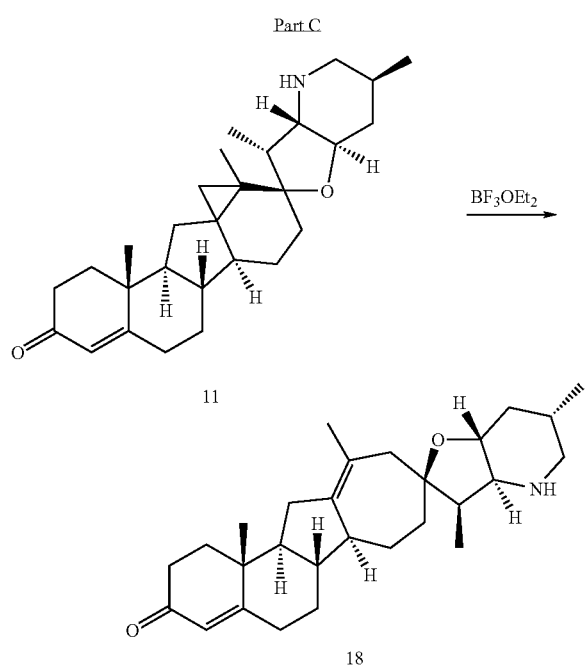

To a solution of cyclopropylenone 11 (10 mg, 24 μmol. 1 eq) in DCM (0.5 ml) at 0° C. under argon was added BF$_3$.Et$_2$O (30 μL, 0.24 mmol, 10 eq) and the resulting solution stirred at 0° C. for 1.5 h, diluted with DCM and quenched with saturated sodium bicarbonate. The organic phase was washed with sat. sodium bicarbonate and the aqueous layers combined were extracted with DCM. The combined organic layers were washed with brine, dried over MgSO$_4$, filtered and concentrated in vacuo. The residue was purified by preparative TLC (DCM/methanol 9:1). The target 18 was obtained as a white solid (90% yield). MS (ESI(+)) m/e 424.62 (M+H)$^+$.

EXAMPLE 8

Preparation of a Derivative of Cyclopamine

To a solution of cyclopamine 2 (250 mg, 0.6 mmol, 1 eq) in DCM (10 mL) at rt was added Fmoc-OSu (205 mg, 0.6 mmol, 1 eq) and the resulting mixture was stirred at rt overnight. The resulting solution of crude Fmoc-cyclopamine was then cooled to 0° C. and was treated with 15% diethylzinc in toluene (0.5 mL, 0.6 mmol, 1 eq) and stirred for 30 min (Flask A, yellowish solution).

Diiodomethane (0.4 mL, 6 mmol, 10 eq) in DCM (20 mL) at 0° C. was treated with 15% diethylzinc in toluene (3 mL, 3 mmol, 5 eq) and the resulting solution was stirred for 5 min (Flask B, white precipitate).

The contents of Flask B were transferred to Flask A via cannula and the resulting suspension was stirred for 5 h at rt. The reaction was quenched with 1 N hydrochloric acid, stirred for 10 min (until all white solid re-dissolved) and extracted with DCM (5×). The organic extracts were dried over MgSO$_4$, filtered over Celite and concentrated in vacuo. The residue was purified by flash chromatography (hexanes/ethyl acetate 1:1). The target 11,12-monocyclopropane 5 was obtained as a 9:1 mixture of diastereoisomers, along with 20% of diastereomeric bis-cyclopropanated products (80% total recovery). This mixture was separated using preparative SFC chromatography.

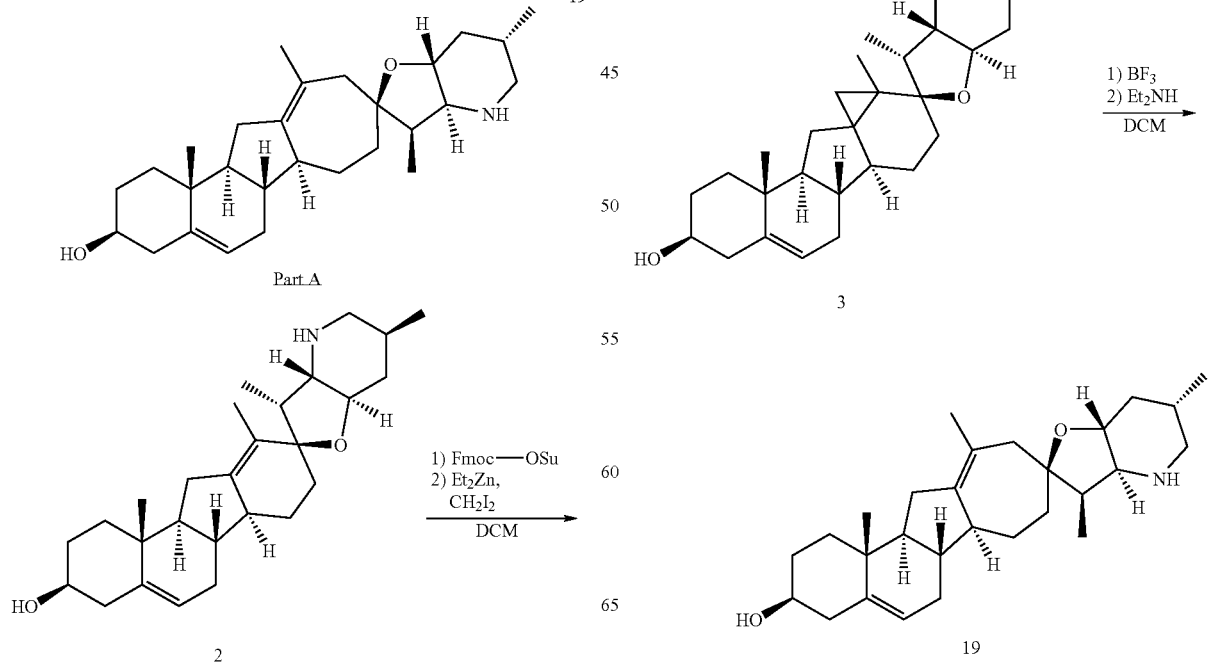

Fmoc-cyclopropylcyclopamine 3 (14 mg, 22 µmol, 1 eq) was dissolved in DCM (0.5 ml), cooled to 0° C. and treated with BF$_3$.Et$_2$O (27 µL, 0.22 mmol, 10 equiv) for 1 h, quenched with saturated sodium bicarbonate, the layers separated and the aqueous one extracted with DCM. The combined organic extracts were dried over MgSO$_4$, filtered and concentrated in vacuo. The residue was purified by preparative thin layer chromatography (hexane/ethyl acetate 2:1). The target, Fmoc-expanded cyclopamine, was obtained as a clear oil.

A solution of crude Fmoc-expanded cyclopamine (20 mg, 31 µmol, 1 eq) in DCM (0.5 ml) was treated with Et$_2$NH (0.5 mL, 4.8 mmol, 154 eq) overnight, concentrated in vacuo and the residue purified by flash chromatography (DCM, DCM/methanol 98:2 and 95:5). The desired compound was obtained as an oil, which crystallized upon standing. MS (ESI(+)) m/e 426.29 (M+H)$^+$.

EXAMPLE 9

Preparation of a Derivative of Cyclopamine

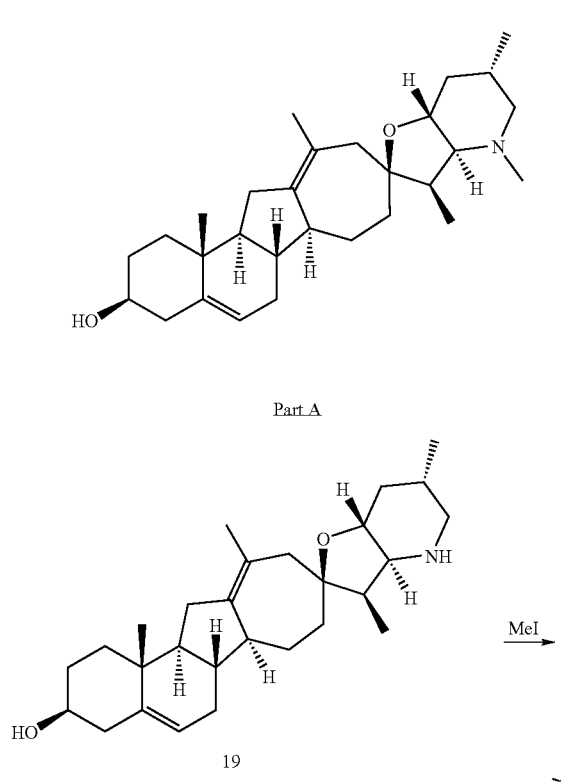

Compound 6 (23 mg, 54 µmol, 1 eq) was dissolved in DCM (1 mL) and methyl iodide (0.17 mL, 0.54 mmol, 10 eq) was added. The reaction was allowed to stir at rt under a nitrogen atmosphere overnight The next morning TLC/LC-MS indicated that there was still some SM. A spatula of Na$_2$CO$_3$ was added and the mixture was stirred for another h. The crude material was loaded onto Biotage 25 Si+M and eluted with DCM/EtOAc/MeOH (82.5/10/7.5). Amorphous material obtained: 16 mg. MS (ESI(+)) m/e 440.32 (M+H)$^+$.

EXAMPLE 10

Preparation of a Derivative of Cyclopamine

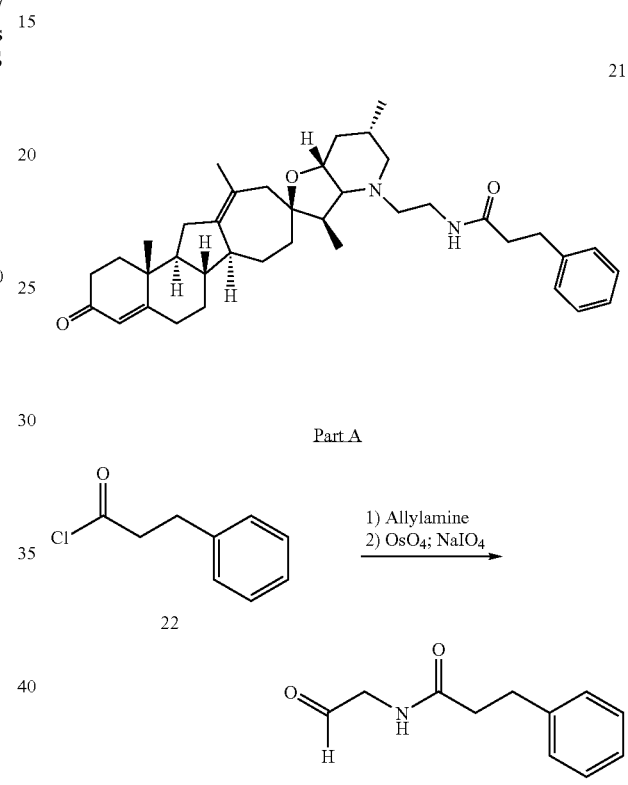

Hydrocinnamoyl chloride 22 (1.13 g, 6.7 mmol, 1 eq) and allyl amine (0.77 mL, 10 mmol, 1.5 eq) were solubilized in THF (20 mL) and the reaction was stirred at rt for 24 h. A white precipitate formed. The reaction mixture was filtered. The filtrate was dried over MgSO$_4$, filtered and concentrated under vacuum. Colorless oil that turned into a waxy solid (1.1 g) was isolated.

To a solution of the allyl amide (0.81 mg, 0.27 mmol, 1 eq) in a mixture of acetone:water (9 mL; 3:1) at 0° C. was added a solution of OsO$_4$ (0.55 mL, 2.5 w/w in t-BuOH) and the resulting brownish mixture was stirred for 10 min. Solid sodium periodate (0.13 g, 0.59 mmol, 2.2 eq) was added in three portions and the mixture was stirred at 0° C. and allowed to warm to 25° C. over a period of 2 h. The light off white creamy mixture was diluted with DCM (25 mL), dried with magnesium sulfate, the solids were filtered off through a pad of celite, the filtrate was concentrated under reduced pressure. The crude slowly develops a yellow black color. The crude material was loaded onto Biotage 25+S and purified eluting with hexane/EtOAc (1:1 to 1:2) to obtain a colorless oil, which solidified once dried (250 mg).

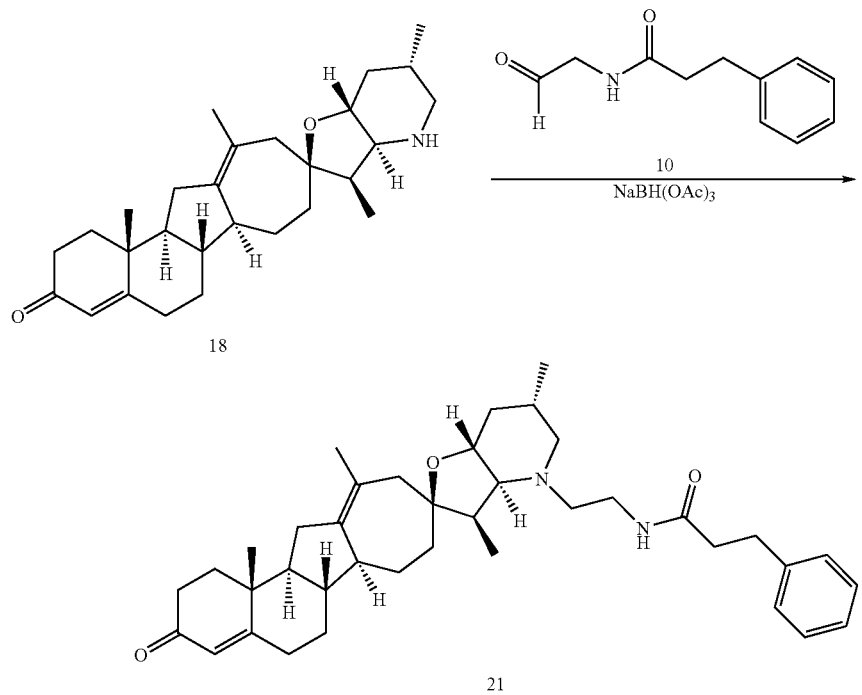

To a solution of 18 (108 mg, 0.25 mmol, 1 eq) and the aldehyde 21 (100 mg, 0.52 mmol, 2.1 eq) in DCM (5 mL) was added sodium triacetoxyborohydride (100 mg, 0.47 mmol, 1.9 eq) in one portion and the slurry was stirred at rt for 7 h. The reaction was quenched by adding MeOH and filtering through celite. Evaporation to dryness yield 230 mg of oil. Material was purified by chromatography (SiO$_2$, column 3 cm×4 cm) eluting with hexane/EtOAc (4:6 to 2:8) to yield 38 mg of the desired product. MS (ESI(+)) m/e 599.74 (M+H)$^+$.

EXAMPLE 11

Preparation of a Derivative of Cyclopamine

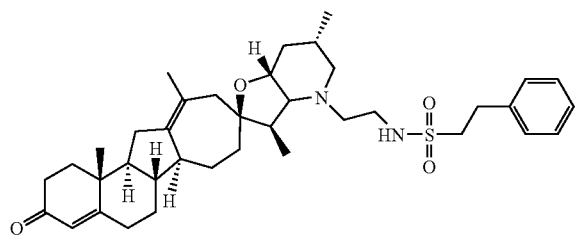

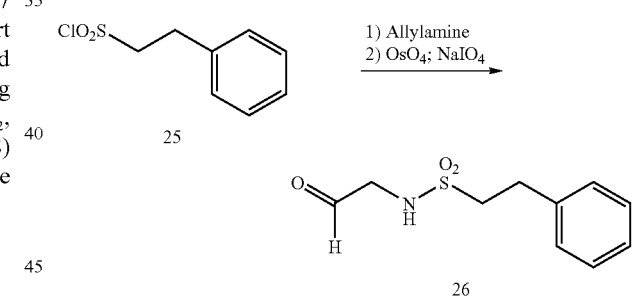

2-phenylethanesulfonyl chloride 25 (1.13 g, 5.5 mmol, 1 eq) and allyl amine (0.56 mL, 7.3 mmol, 1.3 eq) were solubilized in THF (20 mL) and allow to react overnight at rt for 24 h. A white precipitate formed. The reaction mixture was filtered. The filtrate was dried over MgSO$_4$, filtered and concentrated under vacuum. Slightly yellow oil (1.1 g) was isolated. The crude material was used directly in the next step.

To a solution of the allyl sulfonamide (0.15 g, 0.66 mmol, 1 eq) in acetone:water (4 mL, 3:1) at 0° C. was added a solution of OsO$_4$ (0.13 mL, 2.5 w/w in t-BuOH) and the resulting brownish mixture was stirred for 10 min. Solid sodium periodate (0.31 g, 1.46 mmol, 2.2 eq) was added in three portions and the mixture was stirred at 0° C. and allowed to warm to 25° C. over a period of 2 h. The light off white creamy mixture was diluted with DCM (25 mL), dried with magnesium sulfate, the solids were filtered off through a pad of celite, the filtrate was concentrated under reduced pressure. The crude material was purified on SiO$_2$ (column 2 cm×12 cm) eluting with hexane/EtOAc (7:3) to give the desired material (16 mg).

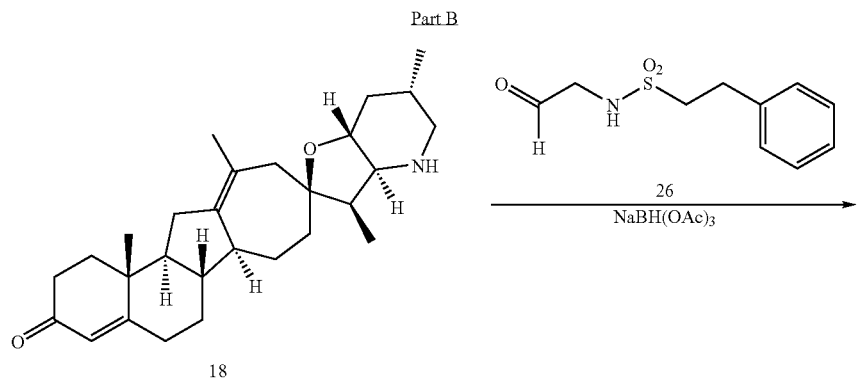

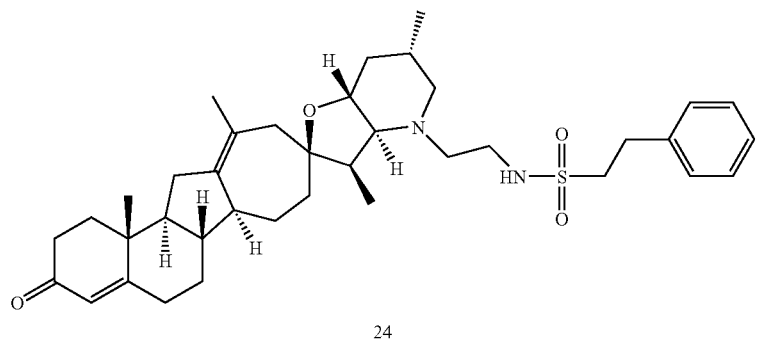

To a solution of 18 (15 mg 35.4 μmol, 1 eq) and the aldehyde 26 (16 mg, 70 μmol, 2 eq) in DCM (3 mL) was added sodium triacetoxyborohydride (20 mg, 94 μmol, 2.6 eq) in one portion at rt. After 24 h the reaction was quenched by adding a few drops of MeOH and filtered on celite. Crude was purified by prep TLC 1 mm (First elution: Toluene/Acetone (9:1), second elution: Tolune/Acetone (4:1)) to yield 4 mg of a colorless oil. MS (ESI(+)) m/e 635.43 (M+H)$^+$.

EXAMPLE 12

Preparation of a Derivative of Cyclopamine

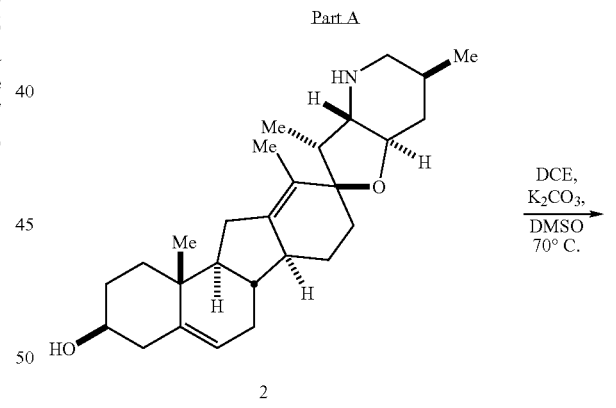

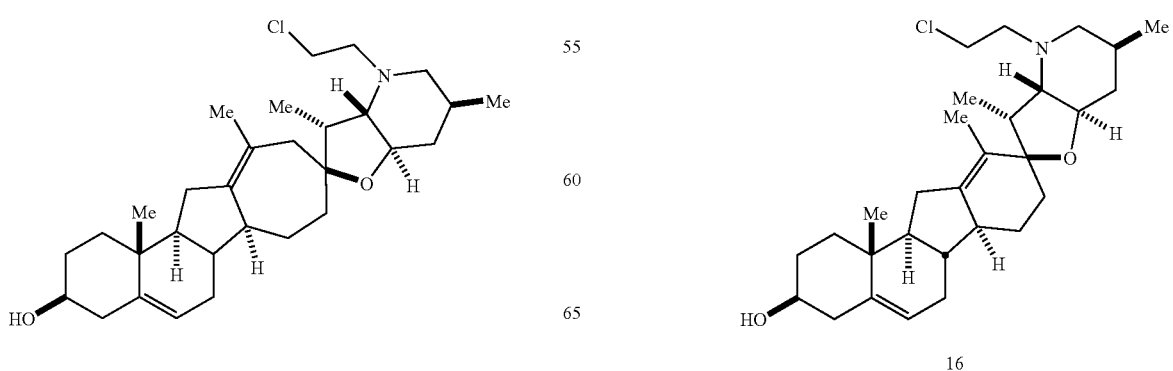

Compound 2 (1.30 g, 3.2 mmol, 1 eq) was massed out and charged into the reaction vessel. Potassium carbonate (0.91 g, 6.6 mmol, 2.1 eq) was massed out and charged into the reaction vessel followed by dichloroethane (6.0 mL, 76 mmol, 23.8 eq.) and anhydrous DMSO (5 mL). The reaction was heated to 70° C. for 36 hours under a nitrogen atmosphere. The reaction was cooled to rt, diluted with DCM (15 mL) and washed twice with water (2×15 mL). The organic layer was dried over sodium sulfate, filtered (DCM rinse as necessary), and concentrated to dryness to afford a pale yellow solid. Flash chromatography (DCM/EtOAc) affords the target material as a white crystalline solid.

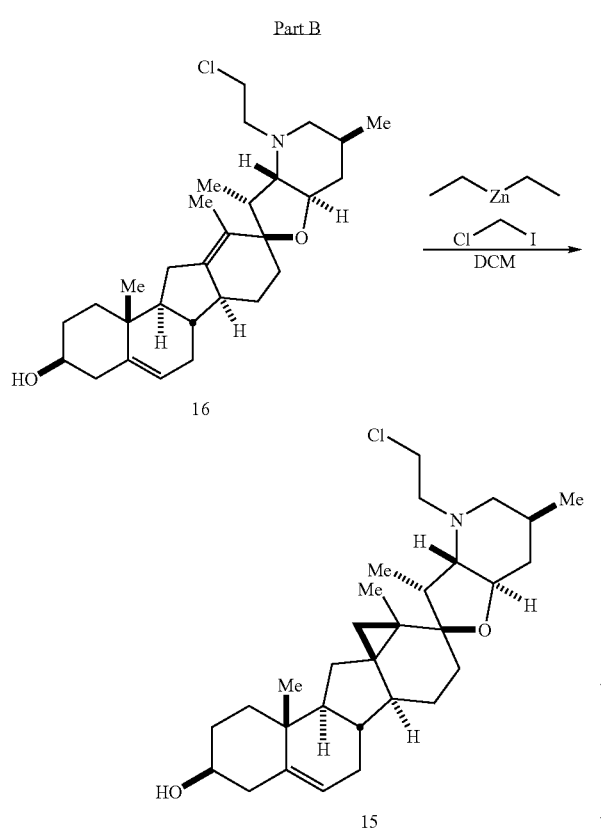

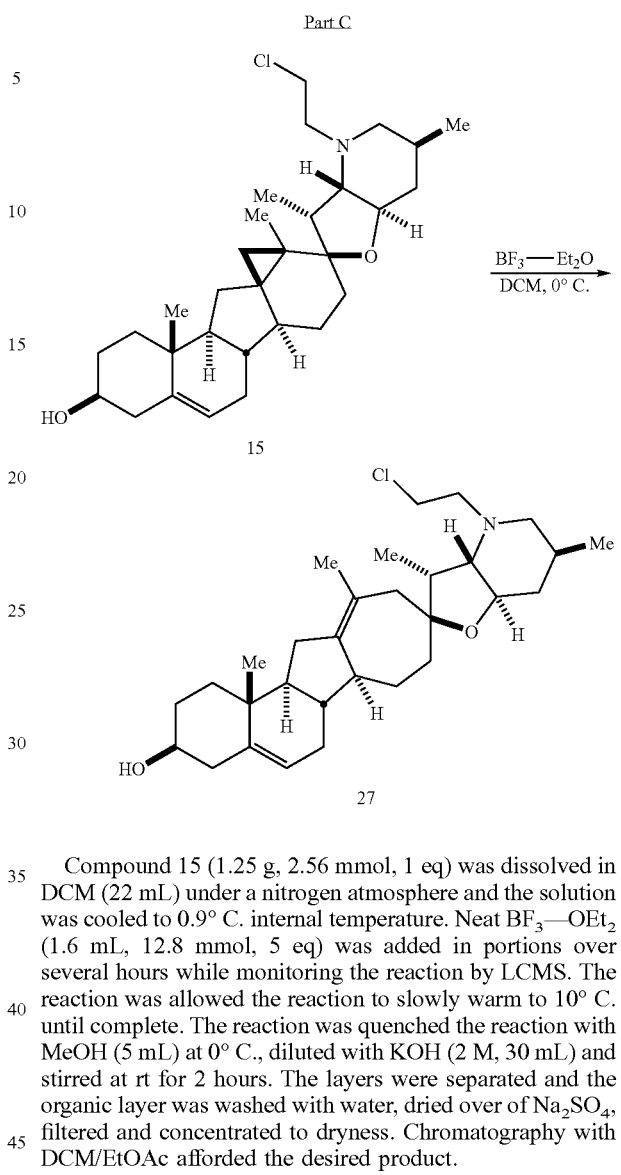

Compound 16 (0.111 g, 0.233 mmol, 1 eq) was transferred to the reaction flask, placed under a nitrogen atmosphere, and dissolved in anhydrous DCM (2 mL). Chloroiodomethane was added (0.238 mL, 3.27 mmol, 14 eq.) The solution was cooled to −15° C. Diethyl zinc (1M in heptane, 1.63 mL, 1.63 mmol, 6.5 equivalents) was added dropwise over 30 minutes carefully controlling the exotherm. The reaction was held between −10° C. and −14° C. for several hours, until TLC indicated that the starting material had been consumed. The reaction was then quenched by the careful addition of THF (6 mL) and then aqueous citrate buffer (pH 4.5, 10 mL). The layers were allowed to warm to rt. saturated sodium sulfate (10 mL). The layers were mixed well, transferred to a seperatory funnel with excess DCM and the organic layer was collected. The organic layer was washed with aqueous sodium hydroxide (1M, 10 mL), and saturated sodium sulfate (10 mL), dried over sodium sulfate before concentrating to dryness. The crude material was purified by flash chromatography to yield the desired product in 55% yield.

Compound 15 (1.25 g, 2.56 mmol, 1 eq) was dissolved in DCM (22 mL) under a nitrogen atmosphere and the solution was cooled to 0.9° C. internal temperature. Neat $BF_3$—$OEt_2$ (1.6 mL, 12.8 mmol, 5 eq) was added in portions over several hours while monitoring the reaction by LCMS. The reaction was allowed the reaction to slowly warm to 10° C. until complete. The reaction was quenched the reaction with MeOH (5 mL) at 0° C., diluted with KOH (2 M, 30 mL) and stirred at rt for 2 hours. The layers were separated and the organic layer was washed with water, dried over of $Na_2SO_4$, filtered and concentrated to dryness. Chromatography with DCM/EtOAc afforded the desired product.

EXAMPLE 13

Preparation of a Derivative of Cyclopamine

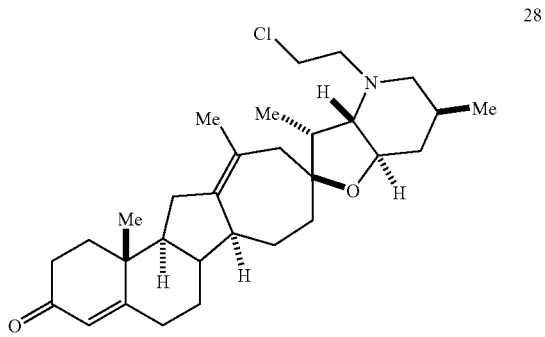

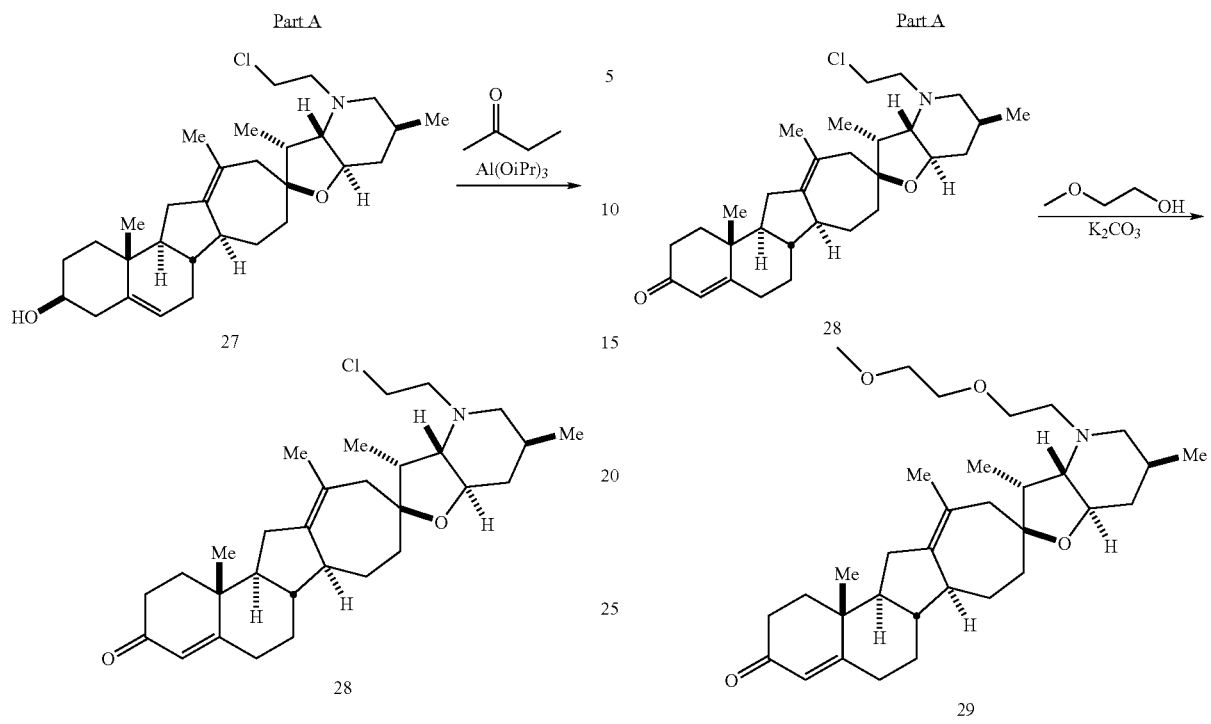

Compound 27 (29 mg, 60 μmol, 1 equiv) was placed into a 5 mL round bottom flask. Butanone (2 mL) and Al(OiPr)$_3$ (12.3 mg, 60 μmol, 1 equiv) were added. The contents of the round bottom were heated at reflux under argon for 7 h. The reaction mixture was then stirred at rt for 10 h. The reaction mixture was then quenched with a solution (2 mL) formed by mixing citric acid (500 g), NaOH (15.7 g) and water (500 mL). The resulting mixture was stirred rapidly until the emulsion dissipated. The mixture was then extracted with EtOAc (3×10 mL). The organic layers were collected, dried over Na$_2$SO$_4$ and concentrated. The crude material was purified by column chromatography. MS (ESI(+)) m/e 486.26 (M+H)$^+$.

Compound 28 (25 mg, 0.051 mmol, 1 eq) was dissolved in anhydrous 2-methoxyethanol (1 mL, 12.7 mmol, 234 eq). Potassium carbonate (7.1 mg, 0.051 mmol, 1 eq) was added and the reaction was heated to 120° C. The reaction was monitored by TLC. When TLC indicated that the reaction had stopped the reaction was cooled to rt. The reaction was then diluted with ethyl acetate and washed with water. The organic layer was dried over sodium sulfate and concentrated to dryness. Chromatography with DCM/EtOAc afforded the desired product. MS (ESI(+)) m/e 526.66 (M+H)$^+$.

EXAMPLE 14

Preparation of a Derivative of Cyclopamine

EXAMPLE 15

Preparation of a Derivative of Cyclopamine

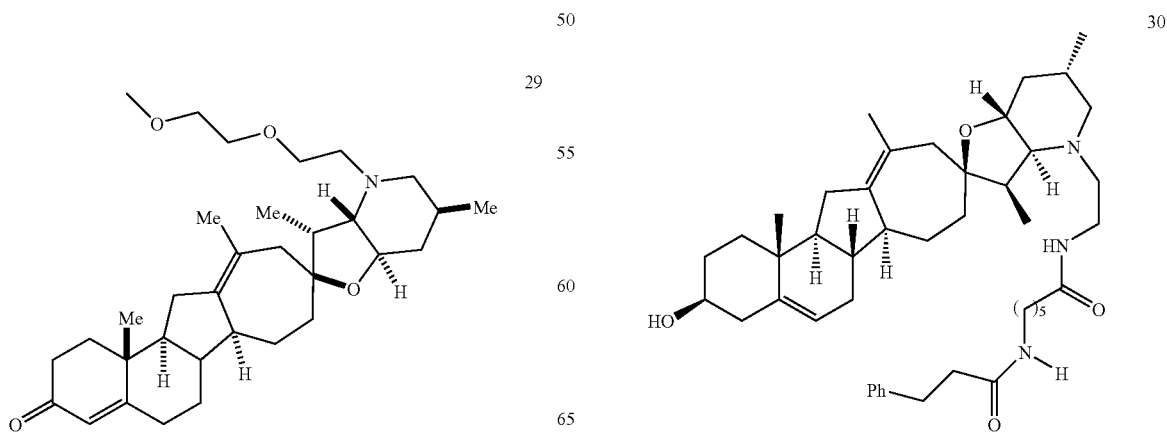

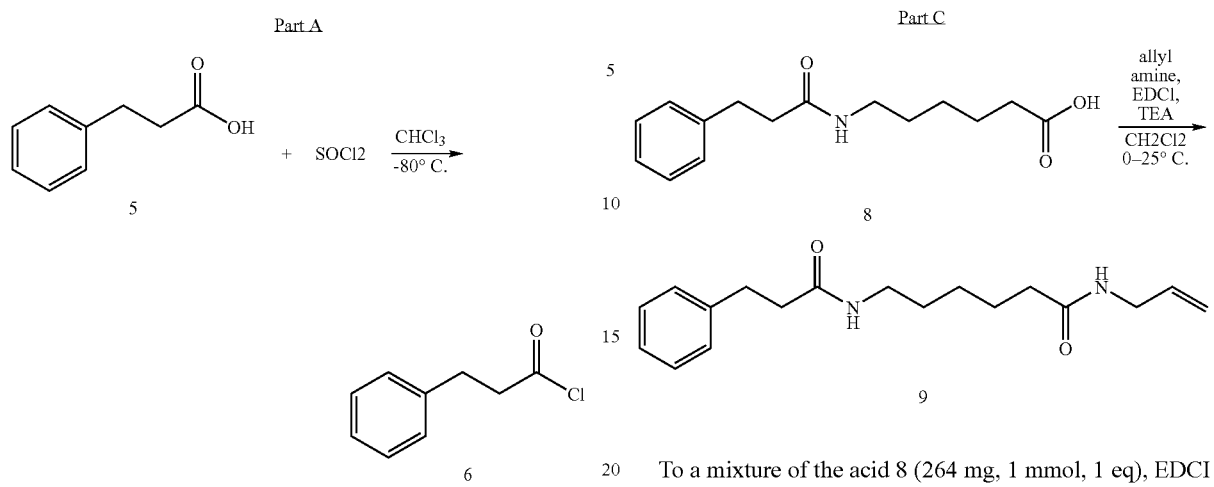

To a solution of hydrocinnamic acid 5 (3.01 g, 20 mmol, 1 eq) in 30 mL anhydrous chloroform at 75° C. was added thionyl chloride (1.75 mL, 24.1 mmol, 1.2 eq) dropwise over a period of 3 min. The mixture was refluxed for 3.5 h. The solvent was distilled off to give the crude acid chloride as a light yellow viscous liquid. The crude was used without further purification.

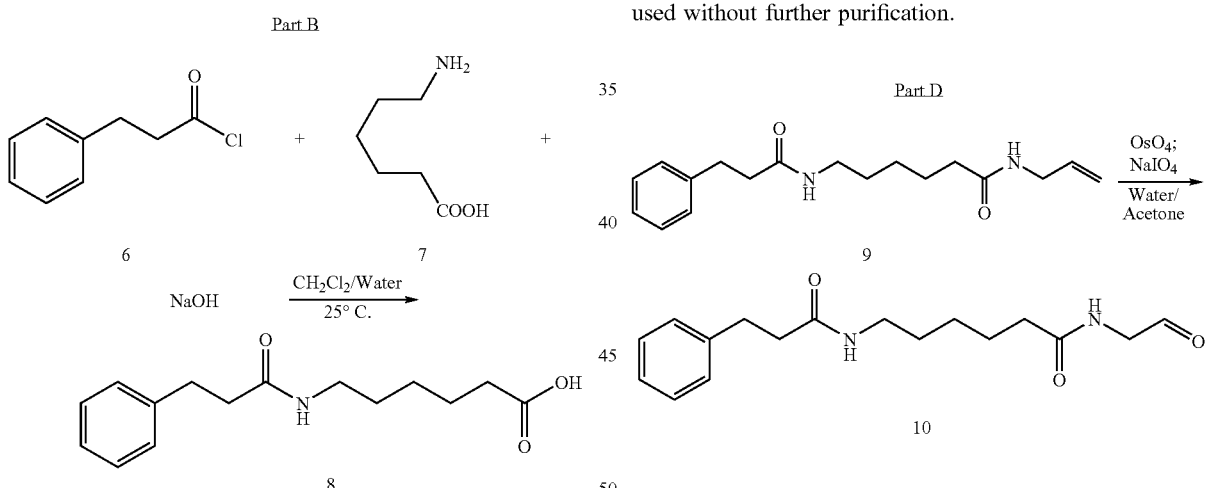

To a biphasic mixture of 7 (3.16 g, 24.1 mmol, 1.2 eq) in DCM (30 mL) and an aqueous solution of NaOH (2.0 M, 30 mL, 3 eq) at 25° C. was added a solution of the acid chloride 6 (3.38 g, 20 mmol, 1 eq) in DCM (10 mL) and the resulting mixture was stirred at 25° C. for 3 h. The mixture was then neutralized with aqueous HCl (2 M, 30 mL). The organic layer was then separated and the aqueous layer was extracted with DCM (3×50 mL). The combined organic layers were washed with HCl (2.0 M, 25 mL), water (3×50 mL), saturated brine (50 mL), dried over magnesium sulfate and the solvent was evaporated under reduced pressure. The crude was chromatographed on silica gel using 5% MeOH: DCM as eluant and the column was then eluted with 10% MeOH:DCM to yield 1.141 g of compound 8.

To a mixture of the acid 8 (264 mg, 1 mmol, 1 eq), EDCI (231 mg, 1.2 mmol, 1.2 eq), and triethyl amine (168 μL 1.2 mmo, 1.2 eq) in DCM (2 mL) at 0° C. was added allylamine (90.3 μL, 1.2 mmol, 1.2 eq), and the resulting mixture was stirred at 0° C. for 1 h and allowed to warm to 25° C. over a period of 2 h. The reaction mixture was added to water (50 mL), extracted with DCM (4×25 mL), the combined organic layers were washed with 1 M HCl (2×25 mL), water (3×25 mL), satd brine (25 mL), dried over magnesium sulfate and the solvent was evaporated off under reduced pressure to yield 287.5 mg of the desired product. This material was used without further purification.

To a solution of the allyl amide 9 (70 mg, 0.23 mmol, 1 eq) in 1 acetone (mL) and water (0.3 mL) was added a solution of osmium tetroxide (0.35 mL, 0.035 mmol, 2.5 w/w in t-butanol) and the reaction mixture was immediately cooled in an ice bath after the OsO4 solution was added. The resulting dark brown solution was stirred at 0° C. for 15 min. Sodium periodate (110 mg, 0.51 mmol, 2.2 eq) was added in 5 portions to the above mixture and stirring continued for 1 h at 0° C. and allowed to warm to 25° C. over a period of 2 h. The reaction mixture was diluted with DCM (3 mL), filtered through a short plug of magnesium sulfate and the filter cake was washed with DCM (several times). The filtrate was concentrated and the residue (67.9 mg) was filtered through a short plug of RP silica gel using 5% MeOH:DCM as eluant to yield 38.9 mg of the desired product.

Part E

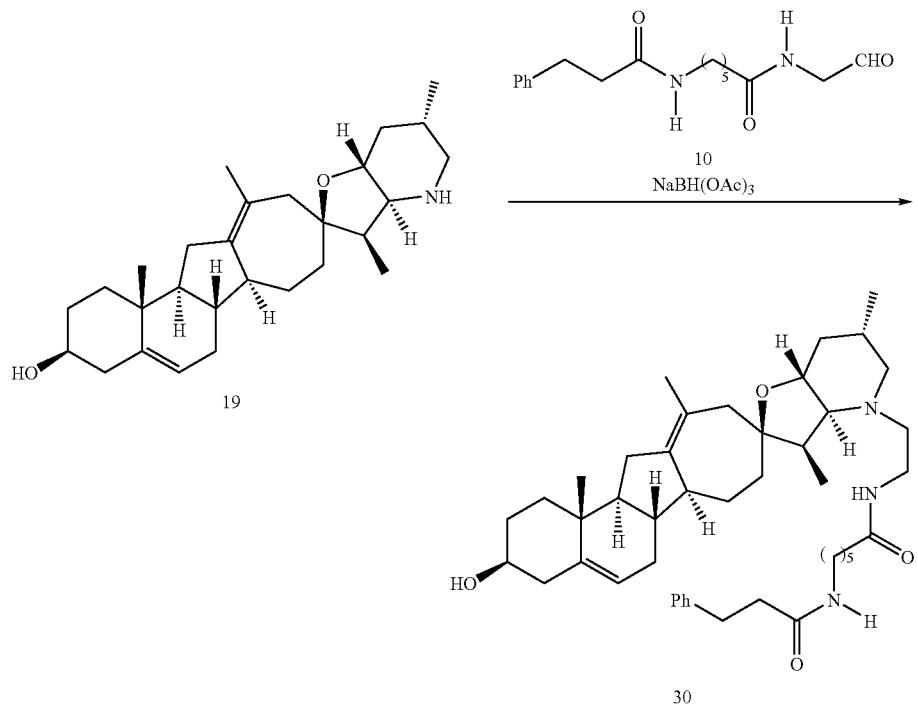

To a solution of 19 (0.0242 g, 0.0569 mmol, 1 eq), and the aldehyde 10 (0.0346 g, 0.114 mmol) in 3.0 mL DCM at 23° C. was added sodium triacetoxy borohydride (24.1 mg, 0.114 mmol, 2 eq) in one portion and the resulting mixture was stirred for 16 h. After complete conversion of stating material into desired product as evident from LCMS and TLC, the mixture was taken up in 2.5 mL methanol and purified by Reverse Phase preparative HPLC (Acetonitrile-20 mM ammonium carbonater buffer, basic method). The fractions were concentrated, and were taken up in minimum volume of acetonitrile, the solution was frozen and lyophilized to give 0.007 g (0.0098 mmol, 17%) as a white solid. MS (ESI(+)) m/e 714.6 (M+H)$^+$.

EXAMPLE 16

Preparation of a Derivative of Cyclopamine

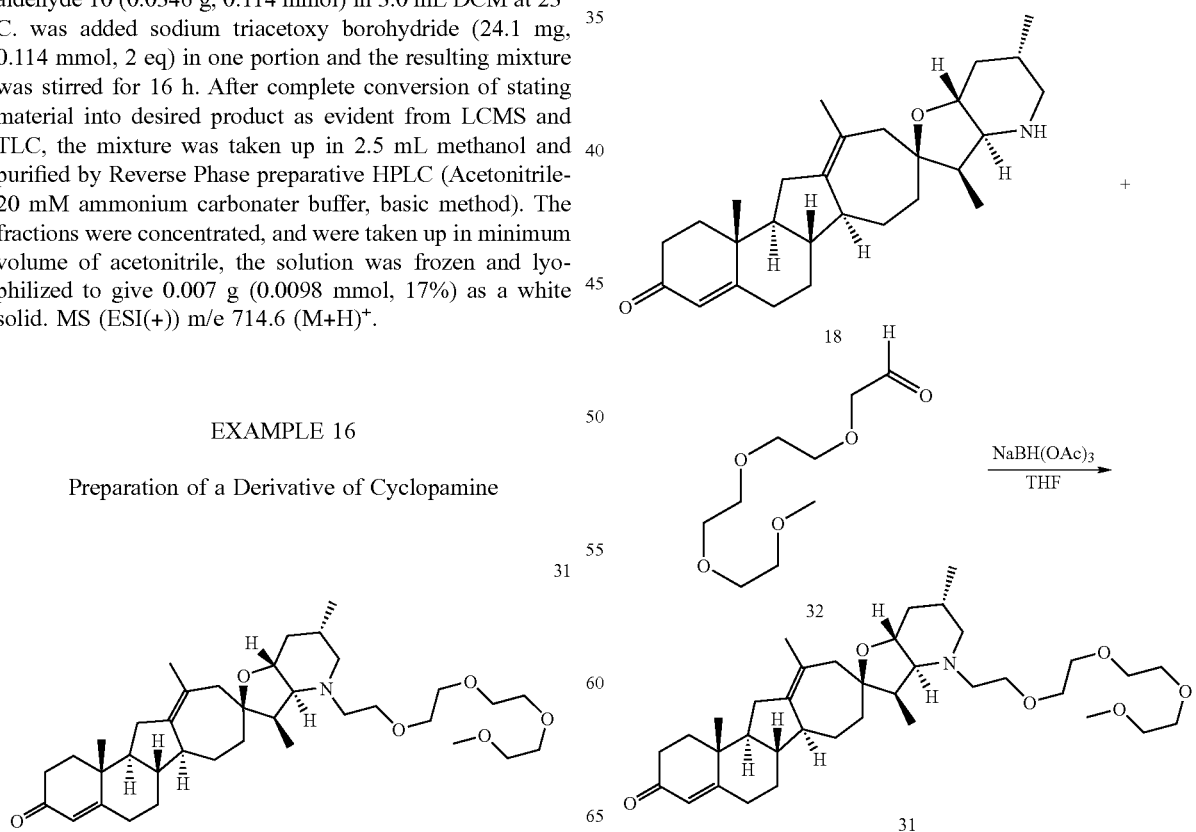

To a solution of 18 (35 mg, 0.08 mmol, 1 eq) and aldehyde 32 (34 mg, 0.17 mmol, 2.0 equiv) in THF (2.0 mL) was added sodium triacetoxyborohydride (35 mg, 0.17 mmol, 2.0 equiv) in one portion. The solution was allowed to stir at 23° C. for 12 h. The mixture was then concentrated and purified by silica gel chromatography using a gradient of 1:1 hexanes:ethyl acetate followed by 1:2, 1:4 and straight ethyl acetate. Some material was still eluting so the column was then flushed with 9:1 ethyl acetate:methanol. The desired product coeluted with some aldehyde so the material was then purified by preparative HPLC. (Basic method 50_100) The desired fractions were frozen and lyophilized to yield oily residue (12 mg, 0.02 mmol, 24% yield). MS (ESI(+)) m/e 614.44 (M+H)+.

EXAMPLE 17

Preparation of a Derivative of Cyclopamine

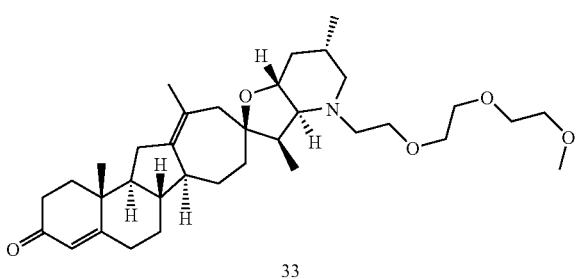

33

To a solution of 18 (8.0 mg, 0.02 mmol, 1 eq) and aldehyde 34 (6.0 mg, 0.04 mmol, 2.0 eq) in $CH_2Cl_2$ (1.0 mL) was added sodium triacetoxyborohydride (8.0 mg, 0.17 mmol, 2.0 eq) in one portion. The solution was allowed to stir at 23° C. for 12 h. The mixture was then concentrated and purified by silica gel chromatography using a gradient of 1:1 hexanes:ethyl acetate followed by 1:2, and 1:4 to isolate the desired product coeluting with some aldehyde. The material was then purified by preparative HPLC. The desired fractions were frozen and lyophilized to yield white powder (4.9 mg, 0.009 mmol, 46% yield). MS (ESI(+)) m/e 570.41 (M+H)+.

EXAMPLE 18

Preparation of a Derivative of Cyclopamine

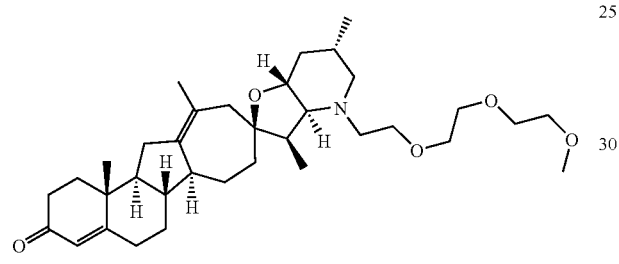

33

Part A

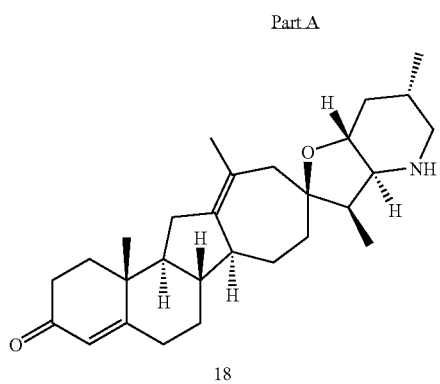

18

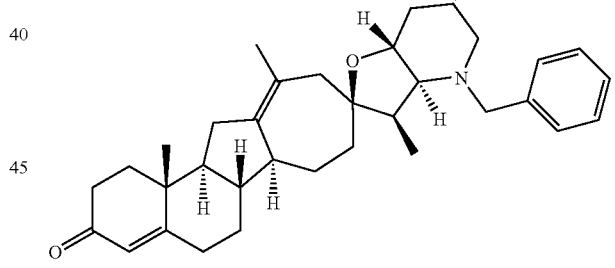

35

Part A

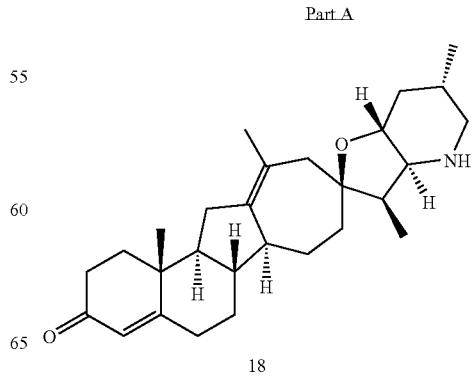

18

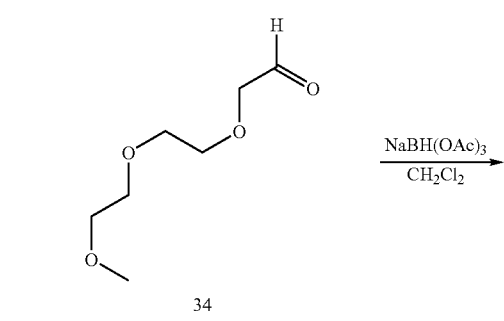

34

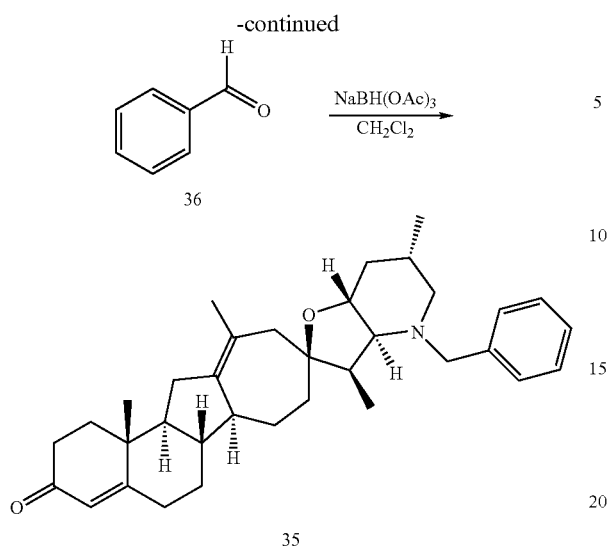

To a solution of 18 (6.0 mg, 0.01 mmol, 1 eq) and benzaldehyde 36 (3.0 mg, 0.02 mmol, 2.0 eq) in CH$_2$Cl$_2$ (0.5 mL) was added sodium triacetoxyborohydride (6.0 mg, 0.02 mmol, 2.0 eq) in one portion. The solution was allowed to stir at 23° C. for 12 h. The mixture was then concentrated and purified by silica gel chromatography using a gradient of 4:1 hexanes:ethyl acetate followed by 1:1 to isolate the desired product coeluting with some aldehyde. The material was then purified by preparative HPLC. The desired fractions were frozen and lyophilized to yield white powder (0.6 mg, 0.001 mmol, 8% yield).

EXAMPLE 19

Preparation of a Derivative of Cyclopamine

To a solution of 18 (6.0 mg, 0.01 mmol, 1 eq) and 4-phenoxybenzaldehyde 38 (6.0 mg, 0.02 mmol, 2.0 eq) in CH$_2$Cl$_2$ (0.5 mL) was added sodium triacetoxyborohydride (6.0 mg, 0.02 mmol, 2.0 eq) in one portion. The solution was allowed to stir at 23° C. for 12 h. The mixture was then concentrated and purified by silica gel chromatography using a gradient of 4:1 hexanes:ethyl acetate followed by 1:1 to isolate the desired product coeluting with some aldehyde. The material was then purified by preparative HPLC. The desired fractions were frozen and lyophilized to yield white powder (1.8 mg, 0.003 mmol, 21% yield). MS (ESI(+)) m/e 606.4 (M+H)$^+$.

EXAMPLE 20

Preparation of a Derivative of Cyclopamine

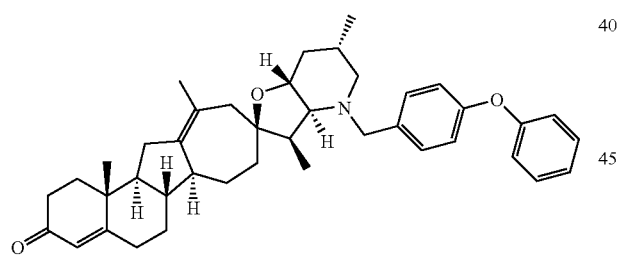

Part A

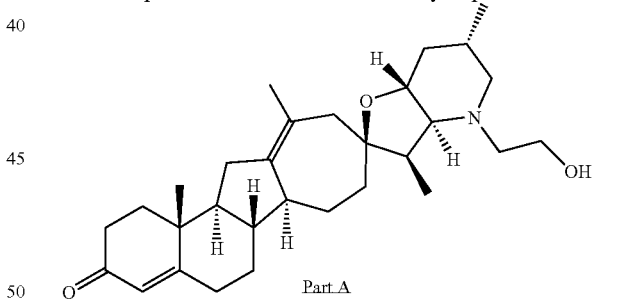

Part A

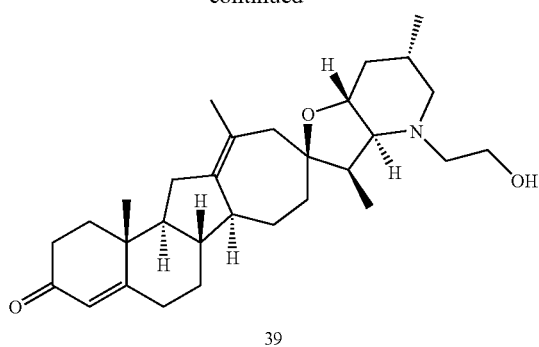

39

To a mixture of 18 (40 mg, 0.09 mmol, 1 eq) and sodium bicarbonate (15 mg, 0.18 mmol, 2.0 eq) in CH$_2$Cl$_2$ (0.5 mL) was added bromoethanol 40 (33 µL, 0.47 mmol, 5.0 eq). The solution was heated to reflux for 4 h. The mixture was then concentrated and purified by silica gel chromatography using a gradient of DCM followed by 38:1:1 dichloromethane:ethyl acetate:methanol, then 36:3:1, then 17:2:1 to isolate the desired product as an oil (12 mg, 0.026 mmol, 27% yield). MS (ESI(+)) m/e 468.24 (M+H)$^+$.

EXAMPLE 21

Preparation of a Derivative of Cyclopamine

41

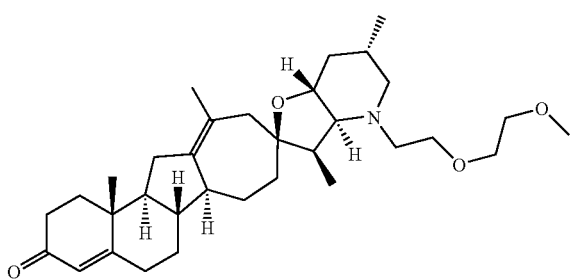

Part A

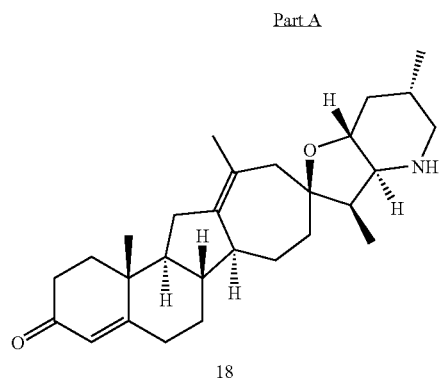

18

+

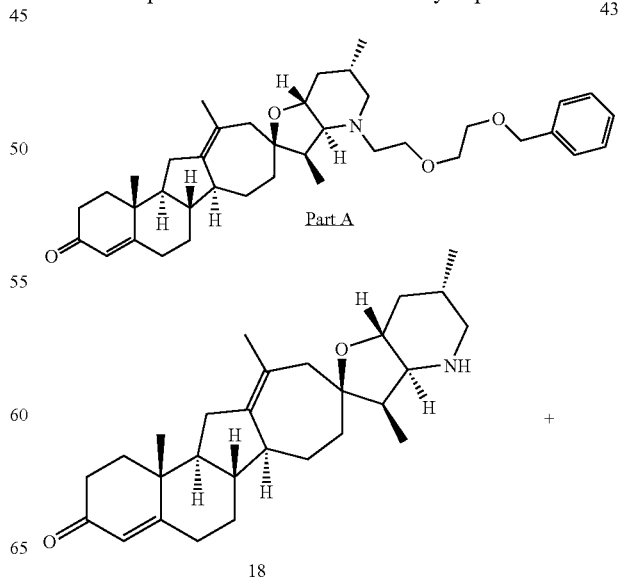

42

41

To a solution of 18 (100 mg, 0.24 mmol, 1 eq) and aldehyde 42 (42 mg, 0.35 mmol, 1.5 eq) in CH$_2$Cl$_2$ (2.5 mL) was added sodium triacetoxyborohydride (100 mg, 0.47 mmol, 2.0 eq) in one portion. The solution was allowed to stir at 23° C. for 12 h and shows only 50% conversion by LCMS. To the mixture was added an additional equivalent of aldehyde 36 (26 mg, 0.24 mmol, 1.0 eq) and sodium triacetoxyborohydride (48 mg, 0.24 mmol, 1.0 eq) and was allowed to stir for 2 h. The mixture was then concentrated and purified by silica gel chromatography using a gradient of 1:1 hexanes:ethyl acetate followed by 1:2, and 1:4 to isolate the desired product coeluting with some aldehyde. The material was then purified by preparative HPLC. The desired fractions were frozen and lyophilized to yield white powder (53 mg, 0.10 mmol, 43% yield). MS (ESI(+)) m/e 526.66 (M+H)$^+$.

EXAMPLE 22

Preparation of a Derivative of Cyclopamine

43

Part A

18

+

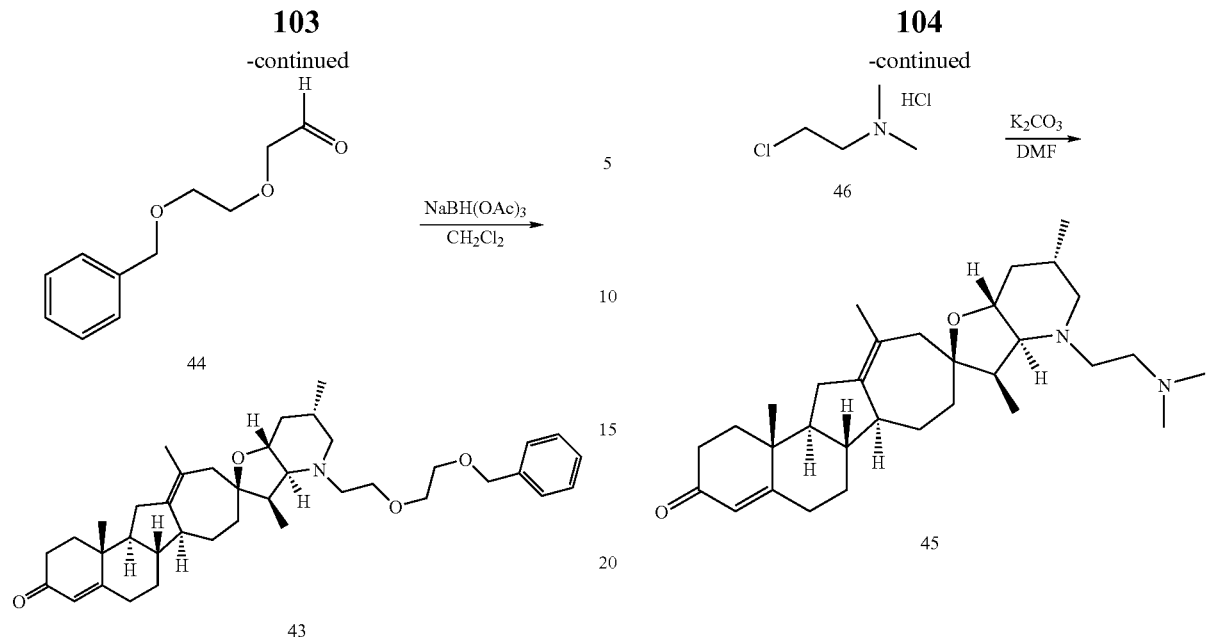

To a solution of 18 (15 mg, 0.04 mmol, 1 eq) and aldehyde 44 (6.9 mg, 0.04 mmol, 1.0 eq) in CH$_2$Cl$_2$ (0.6 mL) was added sodium triacetoxyborohydride (15 mg, 0.07 mmol, 2.0 eq) in one portion. The solution was allowed to stir at 23° C. for 12 h and shows only 50% conversion by LCMS. To the mixture was added an additional equivalent of aldehyde 44 (6.9 mg, 0.04 mmol, 1.0 eq) and sodium triacetoxyborohydride (7.5 mg, 0.04 mmol, 1.0 eq) and was allowed to stir for 12 h. The mixture was then concentrated and purified by silica gel chromatography using a gradient of 1:1 hexanes: ethyl acetate followed by 1:2, and 1:4 to isolate the desired product as an oil (12 mg, 0.19 mmol, 54% yield). MS (ESI(+)) m/e 635.43 (M+H)$^+$.

EXAMPLE 23

Preparation of a Derivative of Cyclopamine

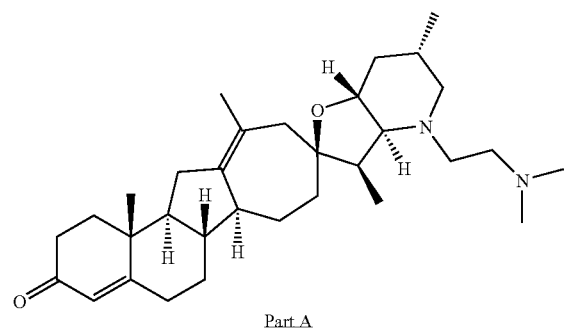

To a mixture of 18 (12 mg, 0.03 mmol, 1 eq) and potassium carbonate (40 mg, 0.28 mmol, 10 eq) in DMF (0.5 mL) was added 2-(dimethylamino)ethyl chloride hydrochloride 46 (20 mg, 0.14 mmol, 5.0 eq). The solution was stirred for 2 h at 23° C. and no reaction took place. The solution was then heated at 65° C. for 12 h, quenched with water (2 mL) and then extracted with diethyl ether (2×10 mL). The combined organic solutions were washed with brine and dried with MgSO$_4$. The mixture was then concentrated and purified by preparative HPLC. The desired fractions were frozen and lyophilized to yield white powder (17, 1.8 mg, 0.004 mmol, 13% yield). MS (ESI(+)) m/e 495.71 (M+H)$^+$.

EXAMPLE 24

Preparation of a Derivative of Cyclopamine

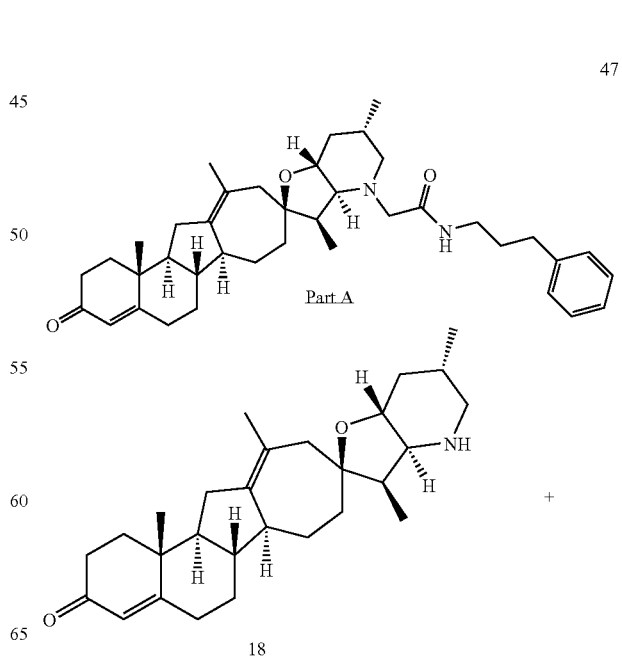

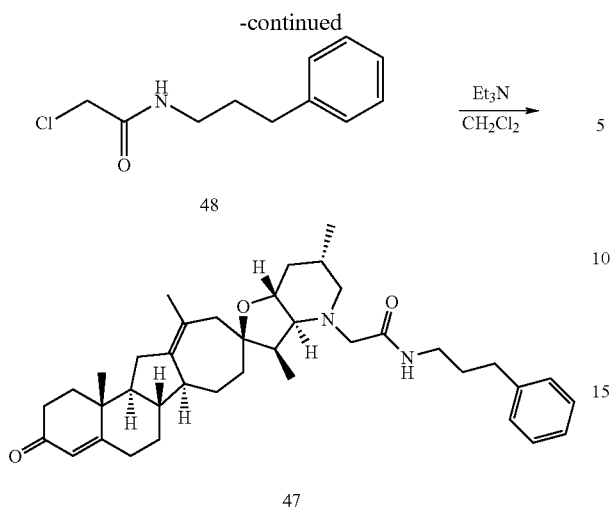

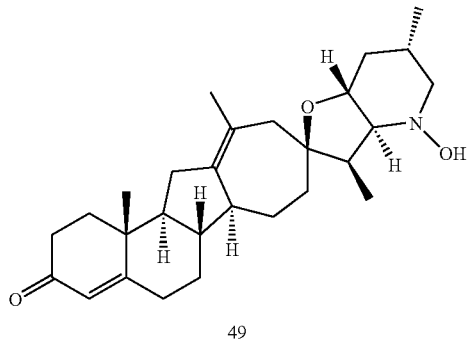

Compound 18 (103 mg, 0.24 mmol, 1 equiv) was dissolved in DCM (3.0 mL) and cooled to −78° C. To this solution was added mCPBA (77% wt, 54 mg, 0.24 mmol, 1.0 equiv) and then the solution was allowed to warm to 22° C. over 12 h. The reaction has gone to 50% conversion (LCMS). The solution was quenched with sodium bicarbonate and extracted with DCM. The combined organics were dried with magnesium sulfate, filtered and concentrated. The material was then purified by silica gel chromatography using a gradient of DCM:EtOAc:MeOH of 95:2.5:2.5 then 92.5:5.0:2.5 then 85:10:5 to isolate desired product coeluting with a small amount of something else. The combined fractions were concentrated and purified by prep HPLC to yield 3.4 mg of the desired product. MS (ESI(+)) m/e 440.63 (M+H)$^+$.

To a solution of 18 (100 mg, 0.24 mmol, 1 eq) and chloroacetamide 48 (250 mg, 1.2 mmol, 5.0 eq) in CH$_2$Cl$_2$ (1.0 mL) was added triethylamine (160 μL, 1.2 mmol, 5.0 eq). The solution was heated to reflux and stirred for 72 h. The mixture was then concentrated and purified by silica gel chromatography using a gradient of 4:1 hexanes:ethyl acetate followed by 2:1, 1:1 and 1:2 to isolate the desired product as a mixture of two spots. The same column conditions were repeated and the desired product was isolated as an oil (17 mg, 0.14 mmol, 12% yield).

EXAMPLE 25

Preparation of a Derivative of Cyclopamine

EXAMPLE 26

Inhibition of the Hedgehog Pathway in Cell Culture Using Analogs of Cyclopamine

Hedgehog pathway specific cancer cell killing effects may be ascertained using the following assay. C3H10T1/2 cells differentiate into osteoblasts when contacted with the sonic hedgehog peptide (Shh-N). Upon differentiation; these osteoblasts produce high levels of alkaline phosphatase (AP) which can be measured in an enzymatic assay (Nakamura et al., 1997 *BBRC* 237: 465). Compounds that block the differentiation of C3H10T1/2 into osteoblasts (a Shh dependent event) can therefore be identified by a reduction in AP production (van der Horst et al., 2003 *Bone* 33: 899). The assay details are described below. The results approximate (EC$_{50}$ for inhibition) of the differentiation assay is shown below in Table 1.

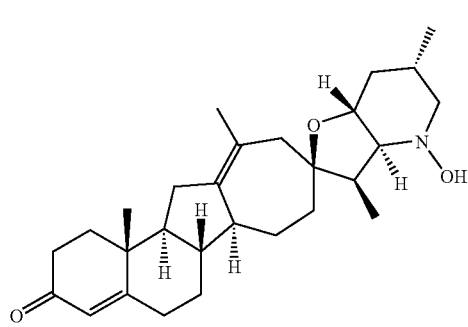

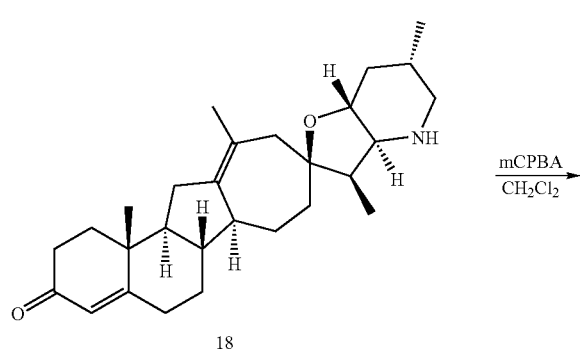

Assay Protocol
Cell Culture
Mouse embryonic mesoderm fibroblasts C3H10T1/2 cells (obtained from ATCC) were cultured in Basal MEM Media (Gibco/Invitrogen) supplemented with 10% heat inactivated FBS (Hyclone), 50 units/ml penicillin and 50 ug/ml streptomycin (Gibco/Invitrogen) at 37C with 5% CO$_2$ in air atmosphere.
Alkaline Phosphatase Assay
C3H10T1/2 cells were plated in 96 wells with a density of 8×10$^3$ cells/well. Cells were grown to confluence (72 hrs). After sonic Hedgehog (250 ng/ml), (R&D Systems) and/or compound treatment, the cells were lysed in 110 ul of lysis buffer (50 mM Tris pH 7.4, 0.1% TritonX100), plates were sonicated and lysates spun through 0.2 um PVDF plates (Corning). 40 ul of lysates was assayed for AP activity in alkaline buffer solution (Sigma) containing 1 mg/ml p-Nitrophenyl Phosphate. After incubating for 30 min at 37C, the plates were read on an Envision plate reader at 405 nm. Total protein was quantified with a BCA protein assay kit from Pierce according to manufacturer's instructions. AP activity was normalized against total protein. Note that "A" indicates that the $IC_{50}$ is less than 200 nM, "B" indicates that the $IC_{50}$ is 200–500 nM, "C" indicates that the $IC_{50}$ is >500 nM.

TABLE 1

Approximate $EC_{50}$ for Inhibition

| Compound | Differentiation Assay $EC_{50}$ |
|---|---|
| 1 | C |
| 4 | A |
| 11 | C |
| 17 | A |
| 18 | A |
| 19 | B |
| 20 | C |
| 21 | A |
| 24 | B |
| 27 | C |
| 28 | C |
| 29 | A |
| 30 | A |
| 31 | A |
| 33 | A |
| 35 | A |
| 37 | C |
| 39 | C |
| 41 | A |
| 43 | B |
| 45 | B |
| 47 | B |

EXAMPLE 27

Preparative Supercritical Fluid Chromatographic (SFC) Purification Method

Described is a preparative supercritical fluid chromatography method for purification of compounds of the present invention.
Hardware Used:
SFC: Berger PrepSFC System
Ultra-Violet Detector: Knauer Model K-2501
Column: Berger 5 micron Silica, 20 mm by 250 mm
SFC conditions:
Mobile phases: $CO_2$—95%; Methanol—5%
Flow rate: 50.00 mL/minute
Column Temperature: 35 C
Isocratic for 40 minutes at 5% methanol in supercritical CO2
Injection volume: 1000 uL
Sample concentrations are normally run at 5.0 mg/mL
Sample Preparation: Samples are dissolved in 20% DCM/80% methanol
Products elute between 25 and 40 minutes
Ultra-Violet Detector Parameters
Wavelength=210 nm; and Resolution=1.0 nm

EXAMPLE 28

Liquid Chromatography Mass Spectrometry (LCMS) Method

Described is a liquid chromatography mass spectrometry method for the compounds of the present invention.

| [A] Inlet Method Report | | | |
|---|---|---|---|
| Waters Alliance 2795 LC Mobile Phase | | | |
| Solvents | | | |
| A % | 0.0 | | |
| B % | 10.0 | | Acetonitrile |
| C % | 90.0 | | Water20 mM NH4HCO3 |
| D % | 0.0 | | Water0.1 A |
| Flow Ramp | 1.00 | | |
| Flow (ml/min) | 1.500 | | |
| Stop Time (mins) | 4.00 | | |
| Min Pressure (Bar) | 0 | | |
| Max Pressure (Bar) | 300 | | |
| Degasser | On | | |
| Stroke Volume | 100.0 µl | | |
| Waters Alliance 2795 LC Column | | | |
| Column Position | Column 3 | | |
| Equilibration Time (mins) | 0.00 | | |
| Column Temperature (° C.) | 35 | | |
| Column Temperature Limit (° C.) | 5 | | |
| Waters Alliance 2795 LC Rapid Equilibration | | | |
| System Path | Off | | |
| System Flow (ml/min) | 0.00 | | |
| System Time (mins) | 0.00 | | |
| Re-equilibration Time (mins) | 0.00 | | |
| Pre column volume (µl) | 0.00 | | |
| Waters Alliance 2795 I/O | | | |
| Switch 1 | No Change | | |
| Switch 2 | No Change | | |
| Switch 3 | No Change | | |
| Switch 4 | No Change | | |
| Analog Output Setting | Flow Rate | | |

| Waters Alliance 2795 LC Gradient Timetable | | | | | | |
|---|---|---|---|---|---|---|
| The gradient Timetable contains 5 entries which are: | | | | | | |
| Time | A % | B % | C % | D % | Flow | Curve |
| 0.00 | 0.0 | 10.0 | 90.0 | 0.0 | 1.500 | 1 |
| 3.00 | 0.0 | 85.0 | 15.0 | 0.0 | 1.500 | 6 |
| 3.10 | 0.0 | 100.0 | 0.0 | 0.0 | 1.500 | 6 |
| 3.50 | 0.0 | 100.0 | 0.0 | 0.0 | 1.500 | 6 |
| 3.60 | 0.0 | 10.0 | 90.0 | 0.0 | 1.500 | 6 |

| Waters Alliance 2795 LC External Event Timetable | |
|---|---|
| No Entries in the Pump External Event Timetable. | |
| Waters Alliance 2795 Injection Parameters | |
| Inject Type | Sequential |
| Fill Mode | Partial Loop |
| Pre-sample Air Boundary (µl) | 4.0 |
| Post-sample Air Boundary (µl) | 4.0 |
| Pre-load time (mins) | 0.00 |
| Waters Alliance 2795 Autosampler Parameters | |
| Sample Temperature (° C.) | 20 |
| Sample Temperature Limit (° C.) | 20 |
| Draw Depth (mm) | 0 |
| Draw Speed | Normal |
| Seek Well Bottom | False |
| Check Plate Height | False |
| Waters Alliance 2795 Wash Parameters | |
| Wash Frequency | Inject |
| Flush Time (s) | 3 |
| Wash Time (s) | 10 |
| Wash Cycles | 2 |
| Secondary Wash Volume (µl) | 600.0 |
| Wash Sequence | |

-continued

[A] Inlet Method Report

Waters996 PDA

| | |
|---|---|
| Start Wavelength (nm) | 220.00 |
| End Wavelength (nm) | 400.00 |
| Resolution (nm) | 1.2 |
| Sampling Rate (spectra/s) | 1.000 |
| Filter Response | 1 |
| Exposure Time(ms) | Automatic |
| Interpolate 656 | Yes |
| Acquisition stop time (mins) | 4.00 |
| Save to disk: | Yes |
| Waters996 PDA Analog Channel 1 | |
| Output Mode | Off |
| Waters996 PDA Analog Channel 2 | |
| Output Mode | Off |
| End Of Report | |

[B] Experiment Report

| | |
|---|---|
| Name | Default Experiment |
| Creation Time | Fri Jun. 04, 2004 10:25:33 |
| Instrument Identifier | |
| Version Number | 1.0 |
| Duration (min) | 4.0 |
| Calibration Filename | C:\MassLynx\Infinity_2002.PRO\ACQUDB\NAICS_040408.cal |
| Solvent Delay Divert Valve Enabled | 0 |
| Number Of Functions | 1 |
| Function 1: MS Scan, Time 0.00 to 3.50, Mass 200.00 to 1000.00 ES+ | |
| Type | MS Scan |
| Ion Mode | ES+ |
| Data Format | Centroid |
| Parameter File | C:\Masslynx\Infinity_2002.PRO\ACQUDB\default.ipr |
| Start Mass | 200.0 |
| End Mass | 1000.0 |
| Scan Time (sec) | 1.0 |
| InterScan Time (sec) | 0.2 |
| Start Time (min) | 0.0 |
| End Time (min) | 3.5 |

[C] ZQ Tune Parameters

| | Settings | Readbacks |
|---|---|---|
| Source (ES+) | | |
| Capillary (kV) | 3.20 | 3.27 |
| Cone (V) | 35.00 | 37.24 |
| Extractor (V) | 3.00 | 2.81 |
| RF Lens (V) | 0.0 | 0.0 |
| Source Temperature (° C.) | 130 | 129 |
| Desolvation Temperature (° C.) | 350 | 350 |
| Cone Gas Flow (L/Hr) | 20 | 33 |
| Desolvation Gas Flow (L/Hr) | 450 | 466 |
| Analyser | | |
| LM 1 Resolution | 15.0 | |
| HM 1 Resolution | 15.0 | |
| Ion Energy 1 | 0.5 | |
| Multiplier (V) | 550 | −547 |

-continued

[C] ZQ Tune Parameters

| | Settings | Readbacks |
|---|---|---|
| Pressure Gauges | | |
| Pirani Pressure(mbar) | <1e−4 mBars | |
| MUX Configuration | | |
| Probe | Standard | |

INCORPORATION BY REFERENCE

All of the U.S. patents and U.S. published patent applications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of Formula 1:

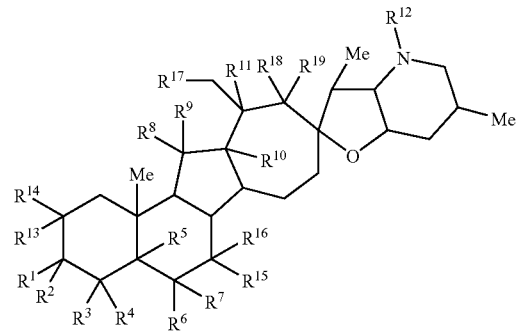

(1)

or a pharmaceutically acceptable salt thereof;

wherein each $R^1$ and $R^8$ is independently H, alkyl, alkenyl, alkynyl, aryl, cycloalkyl, heterocycloalkyl, aralkyl, heteroaryl, heteroaralkyl, halide, sulfhydryl, alkylthio, arylthio, aralkylthio, hydroxyl, alkoxyl, aryloxy, acyloxy, amino, alkylamino, arylamino, acylamino, aralkylamino, nitro, acylthio, carboxamide, sulfonamide, sulfate, —OP(L)(OR$^{20}$)$_2$, —X—C(L)—R$^{21}$ or —X—C(L)-X—R$^{21}$; wherein R$^1$ may also be a sugar;

each X is independently O or NR wherein R is H, alkyl, alkenyl, alkynyl, aryl, cycloalkyl or aralkyl;

L is O or S;

R$^2$ and R$^9$ are independently H, alkyl, alkenyl, alkynyl, aryl, cycloalkyl, heterocycloalkyl, nitrile, aralkyl, alkoxyl, aryloxy, acyloxy, carboxyl, halide, sulfhydryl, alkylthio, arylthio, aralkylthio, hydroxyl, amino, alkylamino, arylamino, acylamino, aralkylamino, heteroaryl, or heteroaralkyl;

each R$^5$ and R$^{11}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;

each R$^3$, R$^4$, R$^6$, R$^7$, R$^{13}$ and R$^{14}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, heteroaryl, or heteroaralkyl;

or R$^1$ and R$^2$ taken together and/or R$^8$ and R$^9$ taken together, along with the carbon to which they are bonded, form —(C=O)—, —(C=S)—, —(C=N (OR$^{20}$))—, —(C=N(R$^{20}$))—, —(C=N(N(R$^{20}$)(R$^{20}$)))—, or form an optionally substituted 3–8 membered ring containing up to two heteroatoms selected from N, O, and S; or R$^4$ and R$^5$ taken together and/or R$^5$ and R$^6$ taken together and/or R$^{10}$ and R$^{11}$ taken together form a double bond or form a group represented by 1b

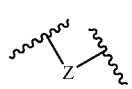
(1b)

wherein Z is NR$^{21}$, O, or C(R$^{23}$)(R$^{23}$);

R$^{12}$ is H, alkyl, alkenyl, alkynyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), —[C(R$^{21}$)$_2$]$_q$—R$^{21}$, —[(W)—N(R$^{21}$)C(O)]$_q$R$^{21}$, —[(W)—C(O)]$_q$R$^{21}$, —[(W)—C(O)O]$_q$R$^{21}$, —[(W)—OC(O)]$_q$R$^{21}$, —[(W)—SO$_2$]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—N(R$^{21}$)]$_q$R$^{21}$, or —[(W)—S]$_q$R$^{21}$;

wherein each W is independently a diradical, and q is 1, 2, 3, 4, 5, or 6;

R$^{15}$, R$^{16}$, and R$^{17}$ are independently H, alkoxyl, aryloxy, acyloxy, halide, hydroxyl, amino, alkylamino, arylamino, acylamino, aralkylamino; or R$^{15}$ and R$^{16}$ taken together, along with the carbon to which they are bonded, form —C(O)— or —C(S)—;

R$^{18}$ and R$^{19}$ are independently H, alkyl, araalkyl, halide, amido, or ester;

each R$^{20}$ is independently H, alkyl, alkenyl, alkynyl, aryl, cycloalkyl, heterocycloalkyl, aralkyl, heteroaryl, or heteroaralkyl; or any two occurrences of R$^{20}$ on the same substituent can be taken together to form a 4–8 membered optionally substituted ring;

each R$^{21}$ is independently H, alkyl, alkenyl, alkynyl, aryl, cycloalkyl, heterocycloalkyl, aralkyl, heteroaryl, heteroaralkyl or —[C(R$^{20}$)$_2$]$_p$—R$^{25}$ wherein p is 0–6; or any two occurrences of R$^{21}$ on the same substituent can be taken together to form a 4–8 membered optionally substituted ring which contains 0–3 heteroatoms selected from N, O, S, and P;

each R$^{23}$ is independently H, alkyl, alkenyl, alkynyl, aryl, cycloalkyl, heterocycloalkyl, aralkyl, heteroaryl, heteroaralkyl, halide, alkoxyl, aryloxy, acyloxy, silyloxy, nitrile, —C(O)R$^{21}$, —CO$_2$R$^{21}$, —SO$_2$R$^{21}$, and —C(O)N(R$^{21}$)$_2$;

each R$^{25}$ is independently H, hydroxyl, acylamino, —N(R$^{20}$)COR$^{20}$, —N(R$^{20}$)C(O)OR$^{20}$, —N(R$^{20}$)SO$_2$(R$^{20}$), —COR$^{20}$N(R$^{20}$)$_2$, —OC(O)R$^{20}$N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^{20}$, —S(O)$_2$OR$^{20}$, —OP(L)(OR$^{20}$)(OR$^{20}$), —NP(O)(OR$^{20}$)(OR$^{20}$), or —P(O)(OR$^{20}$)(OR$^{20}$).

2. The compound of claim 1, wherein R$^{13}$, R$^{14}$, R$^{15}$, R$^{16}$, and R$^{17}$ are hydrogen.

3. The compound of claim 1, wherein R$^1$ is hydroxyl, sugar, —OP(L)(OR$^{20}$)$_2$, —X—C(L)—R$^{21}$, or —X—C(L)—X—R$^{21}$; or R$^1$ and R$^2$ taken together, along with the carbon to which they are bonded, form —C(O)—.

4. The compound of claim 1, wherein R$^4$ and R$^5$ taken together form a double bond.

5. The compound of claim 4, wherein R$^1$ and R$^2$ taken together, along with the carbon to which they are bonded, form —C(O)—.

6. The compound of claim 1, wherein R$^1$ is hydroxyl and R$^2$ is H.

7. The compound of claim 6, wherein R$^5$ and R$^6$ taken together form a double bond;

or R$^5$ and R$^6$ taken together form a group represented by 1b;

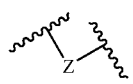
(1b)

wherein:

Z is $C(R^{23})(R^{23})$.

8. The compound of claim 1, wherein $R^{10}$ and $R^{11}$ taken together form a double bond; or $R^{10}$ and $R^{11}$ taken together form a group represented by 1b;

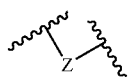

(1b)

wherein:

Z is $C(R^{23})(R^{23})$.

9. The compound of claim 1, wherein $R^5$ and $R^6$ taken together form a double bond and $R^{10}$ and $R^{11}$ taken together form a double bond.

10. The compound of claim 5, wherein $R^{10}$ and $R^{11}$ taken together form a double bond; or $R^{10}$ and $R^{11}$ taken together form a group represented by 1b;

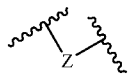

(1b)

wherein:

Z is $C(R^{23})(R^{23})$.

11. The compound of claim 6, wherein $R^{10}$ and $R^{11}$ taken together form a double bond; or $R^{10}$ and $R^{11}$ taken together form a group represented by 1b;

(1b)

wherein:

Z is $C(R^{23})(R^{23})$.

12. The compound of claim 1, wherein $R^8$ and $R^9$ are hydrogen; or $R^8$ and $R^9$ taken together, along with the carbon to which they are bonded, is —C(O)—.

13. The compound of claim 1, wherein $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

14. The compound of claim 2, wherein $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

15. The compound of claim 5, wherein $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

16. The compound of claim 6, wherein $R^{12}$ is H, alkyl, cycloalkyl, aralkyl, heteroaryl, heteroaralkyl, haloalkyl, hydroxyl, alkoxyl, —[(W)—N($R^{21}$)C(O)]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—C(O)]$_q R^{21}$, or —[(W)—C(O)O]$_q R^{21}$.

17. A compound of the formula:

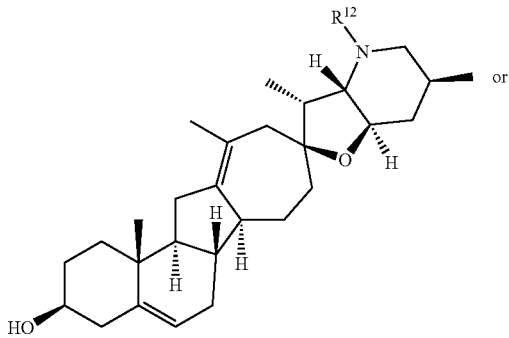

or

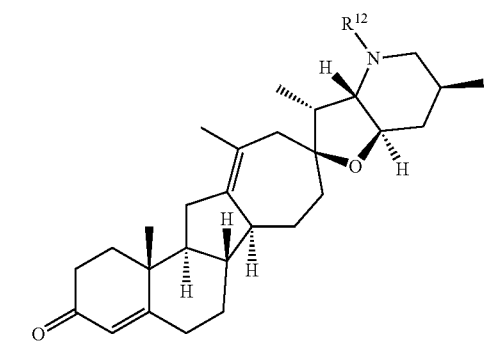

wherein:

$R^{12}$ is H, alkyl, aryl, cycloalkyl, heterocycloalkyl, hydroxyl, aralkyl, heteroaryl, heteroaralkyl, haloalkyl, alkoxyl, —C(O)$R^{21}$, —CO$_2 R^{21}$, —SO$_2 R^{21}$, —C(O)N($R^{21}$)($R^{21}$), —[C($R^{21}$)$_2$]$_p$—$R^{21}$, —[(W)—N($R^{21}$)C(O)]$_q R^{21}$, —[(W)—C(O)]$_q R^{21}$, —[(W)—C(O)O]$_q R^{21}$, —[(W)—OC(O)]$_q R^{21}$, —[(W)—SO$_2$]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—N($R^{21}$)]$_q R^{21}$, or —[(W)—S]$_q R^{21}$;

wherein each W is independently a diradical;

q is 1, 2, 3, 4, 5, or 6;

each $R^{20}$ is independently H, alkyl, alkenyl, alkynyl, aryl, cycloalkyl, heterocycloalkyl, aralkyl, heteroaryl, or heteroaralkyl; or any two occurrences of $R^{20}$ on the same substituent can be taken together to form a 4–8 membered optionally substituted ring containing 0–3 heteroatoms selected from O, N, S, and P;

each $R^{21}$ is independently H, alkyl, aryl, cycloalkyl, heterocycloalkyl, aralkyl, heteroaryl, heteroaralkyl or —[C($R^{20}$)$_2$]$_p$—$R^{25}$ wherein p is 0–6; or any two occurrences of $R^{21}$ on the same substituent can be taken together to form a 4–8 membered optionally substituted ring containing 0–3 heteroatoms selected from O, N, S, and P;

each $R^{25}$ is independently H, hydroxyl, acylamino, —N($R^{20}$)COR$^{20}$, —N($R^{20}$)C(O)OR$^{20}$, —N($R^{20}$)SO$_2$($R^{20}$), —COR$^{20}$N($R^{20}$)$_2$, —OC(O)R$^{20}$N($R^{20}$)($R^{20}$), —SO$_2$N($R^{20}$)($R^{20}$), —N($R^{20}$)($R^{20}$), —COOR$^{20}$, —C(O)N(OH)($R^{20}$), —OS(O)$_2$OR$^{19}$, —S(O)$_2$OR$^{20}$, —OP(O)(OR$^{20}$)(OR$^{20}$), —NP(O)(OR$^{20}$)(OR$^{20}$), or —P(O)(OR$^{20}$)(OR$^{20}$).

18. A compound selected from the group consisting of:
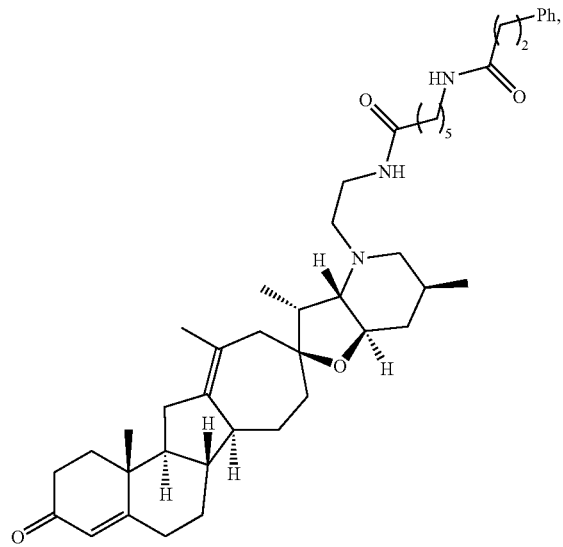
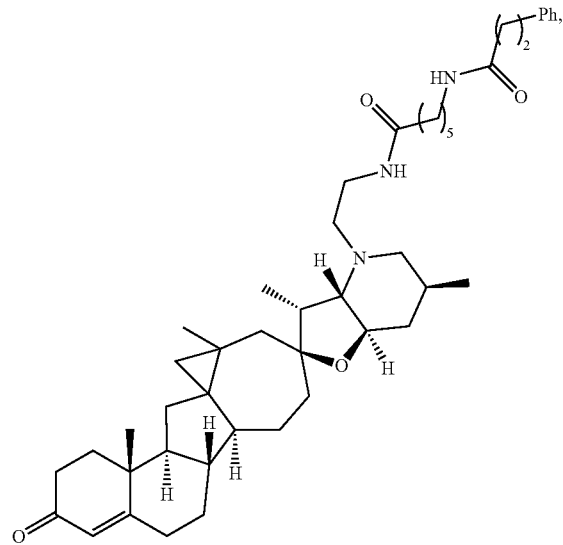
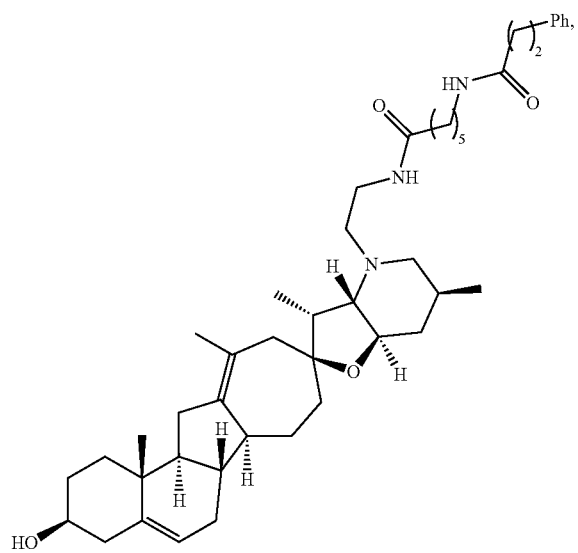
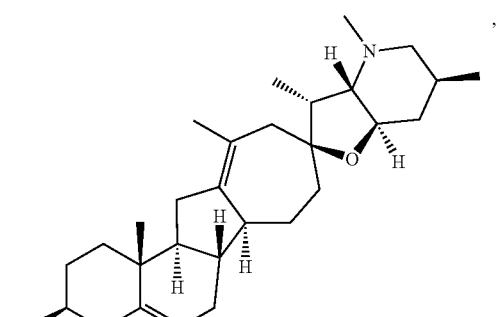
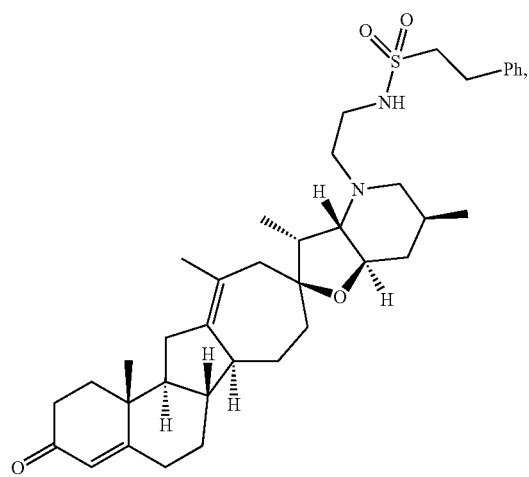
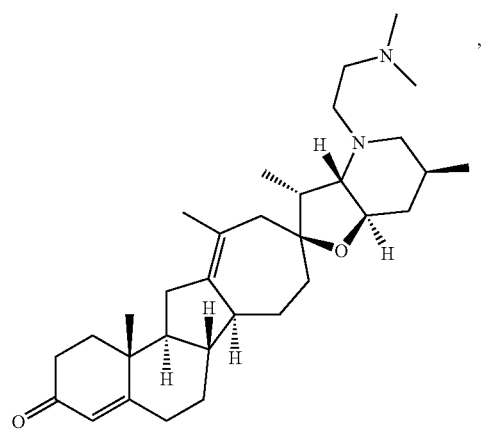

-continued
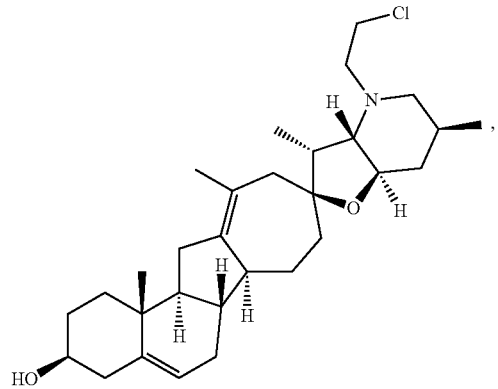
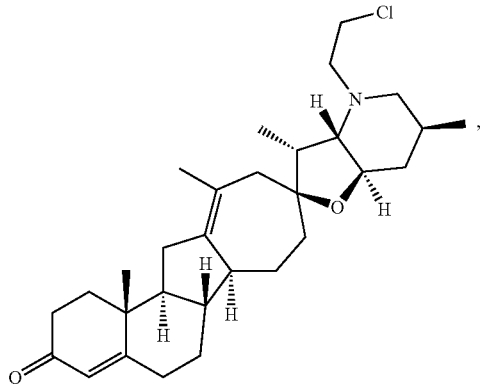
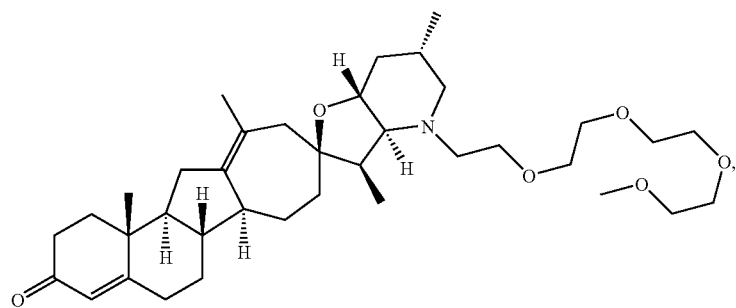
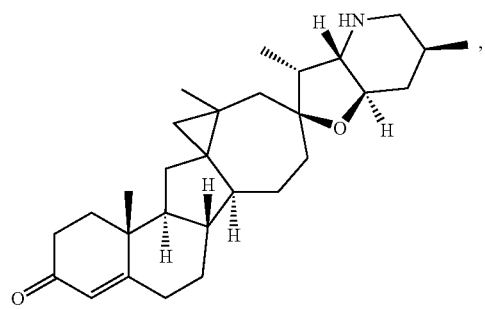
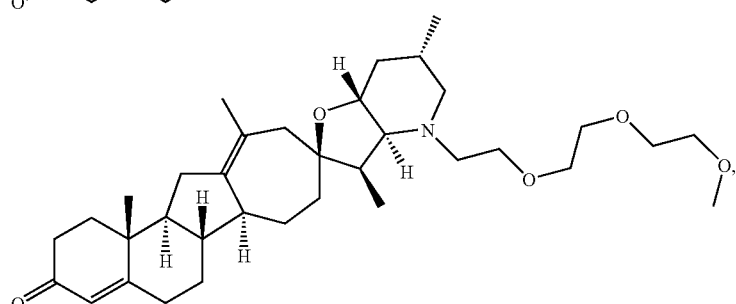
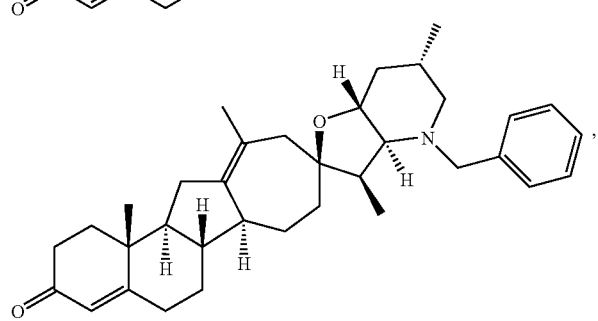

-continued
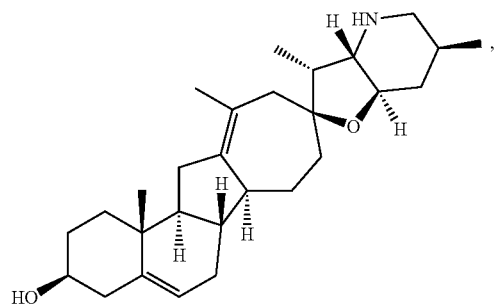
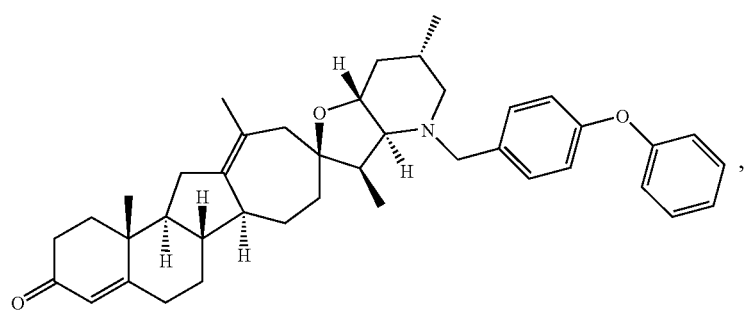
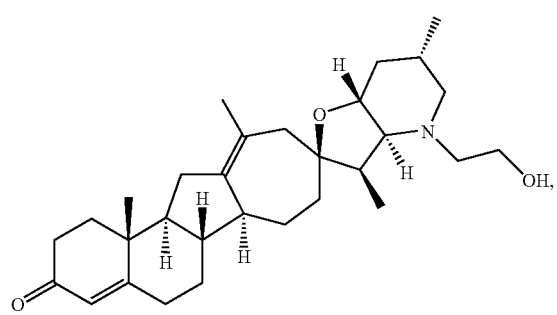
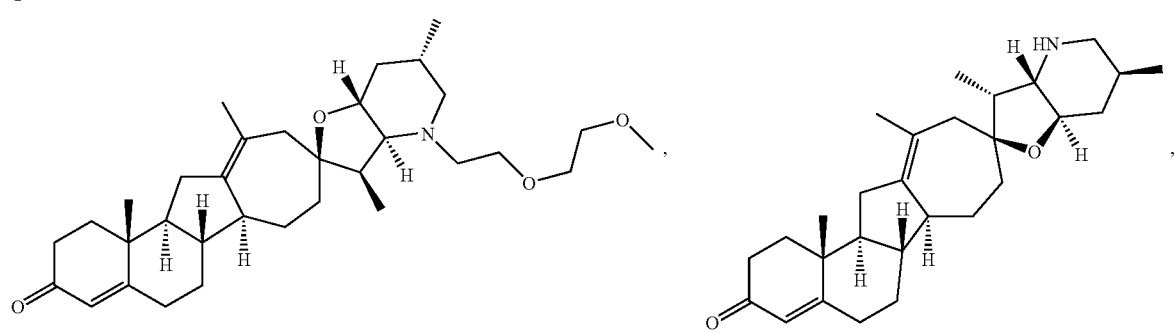
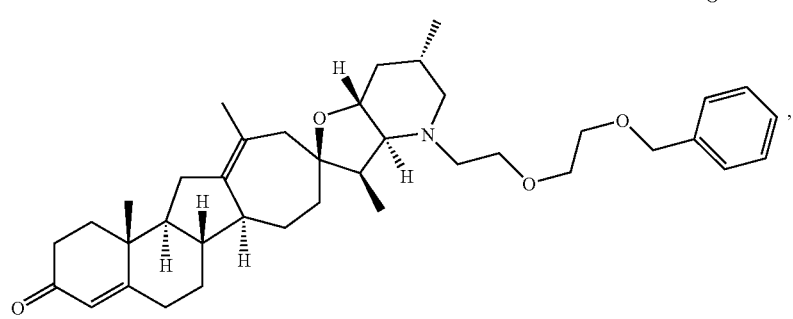

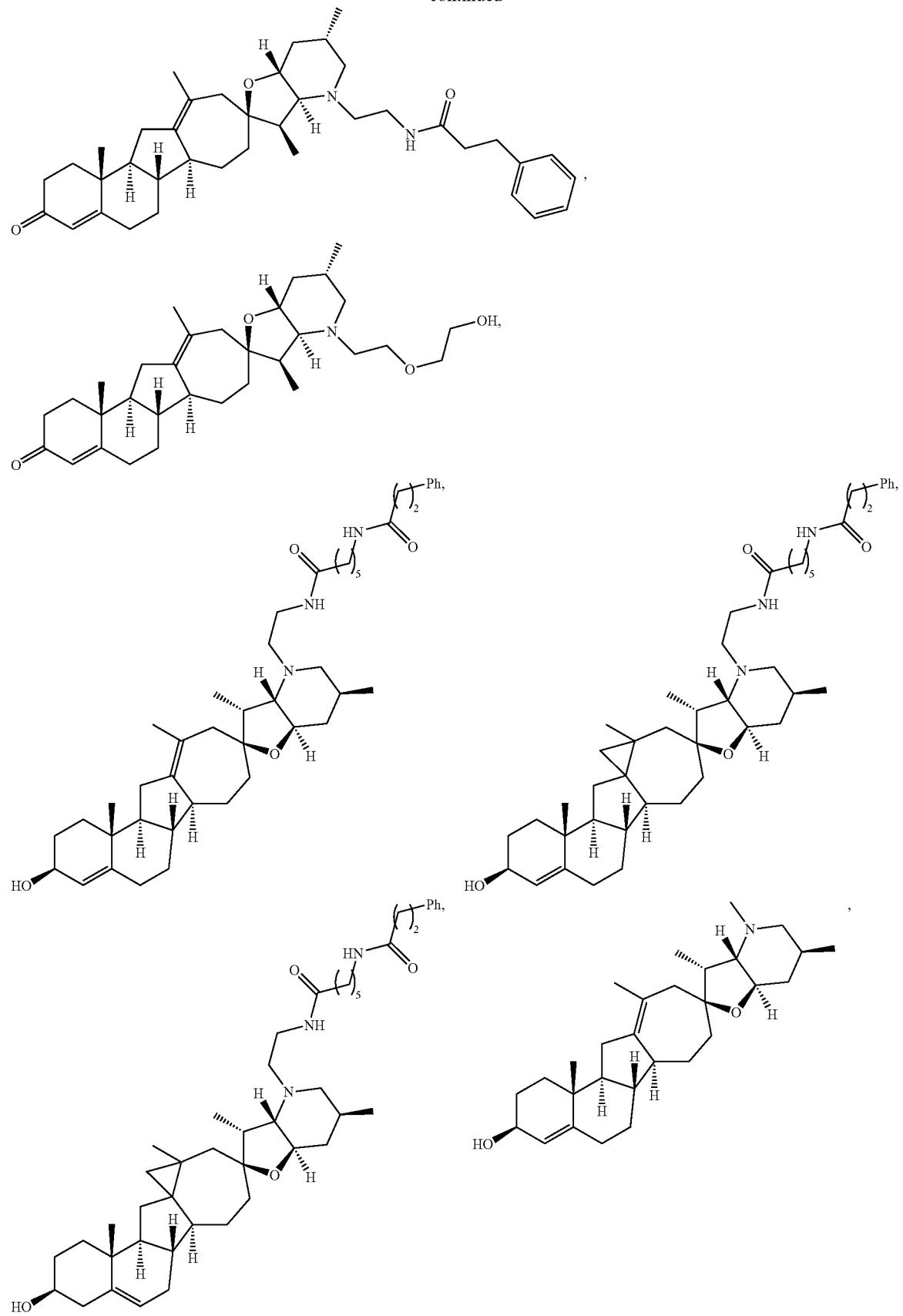

-continued
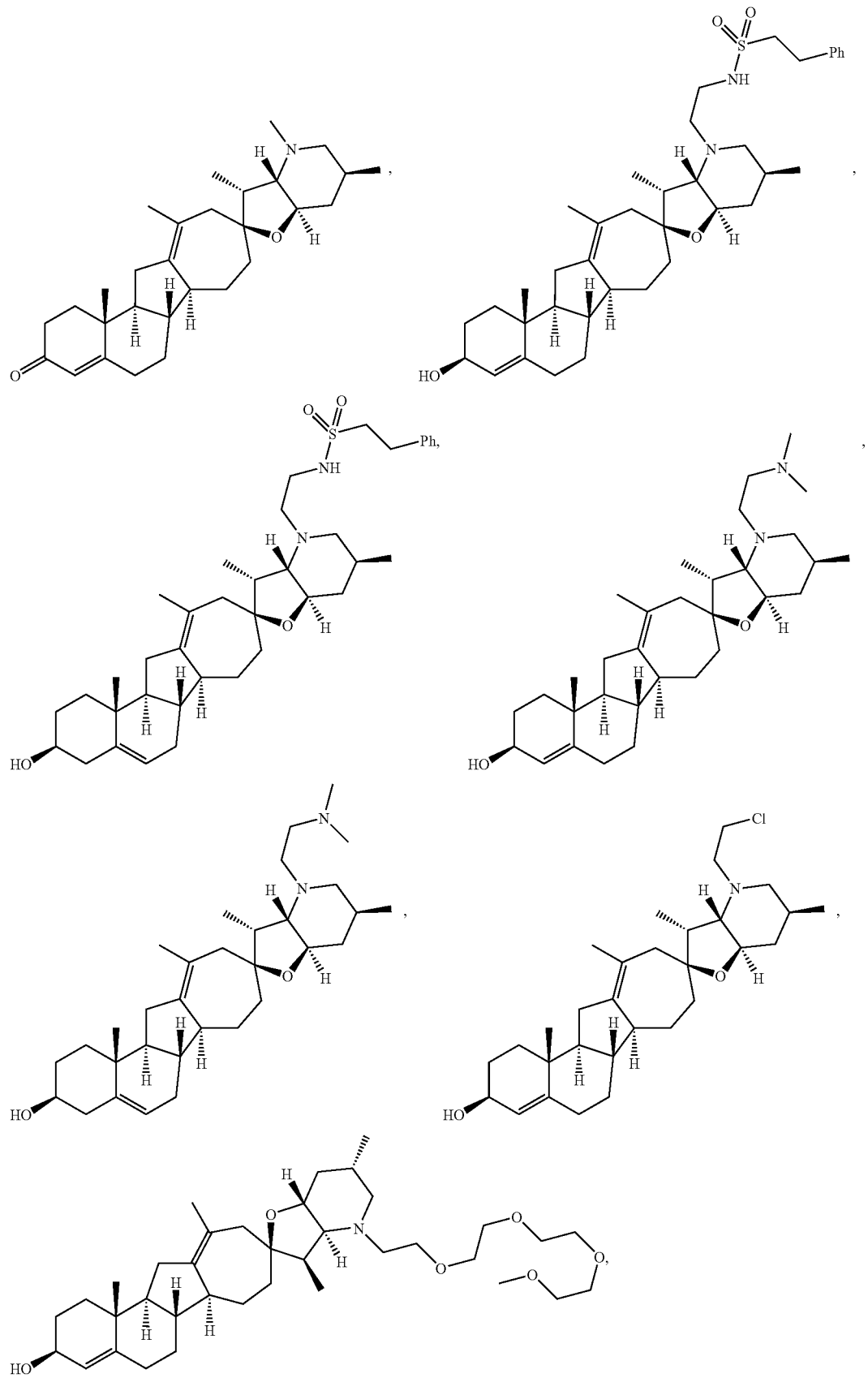

-continued
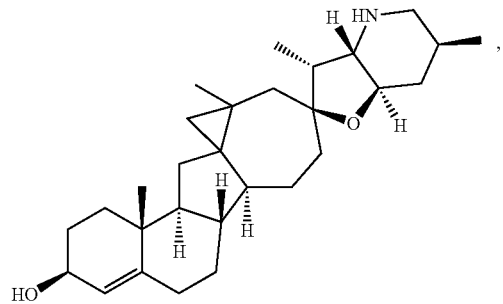
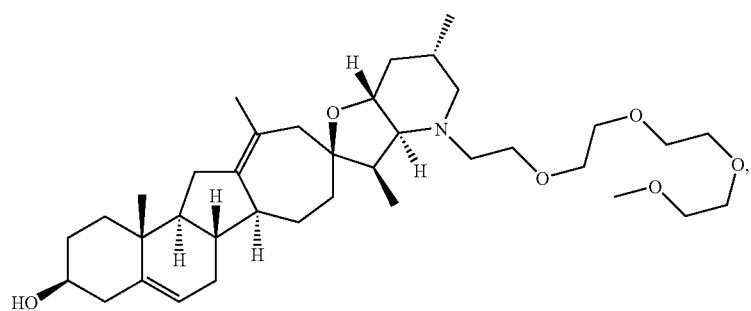
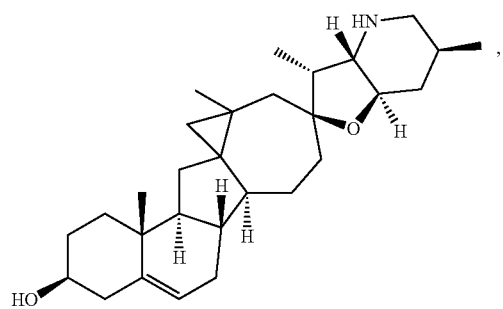
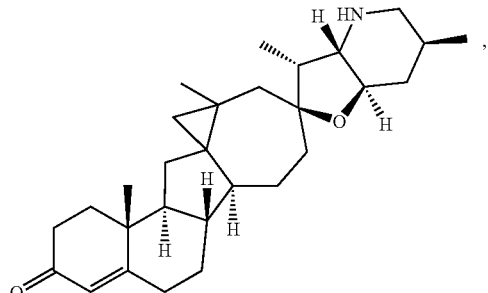
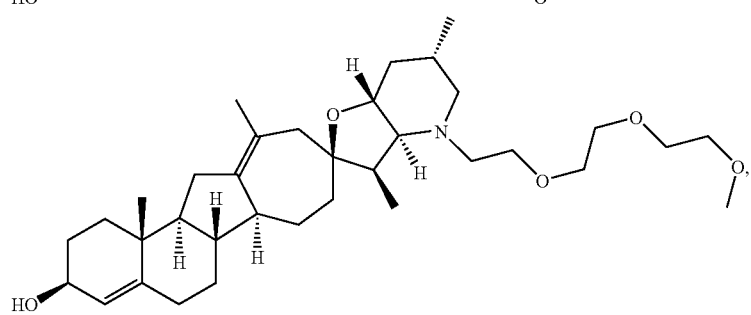
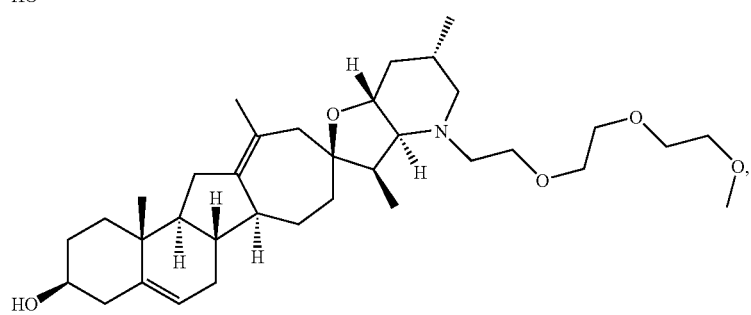

-continued
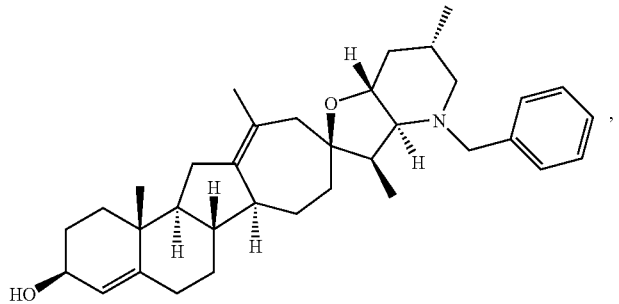
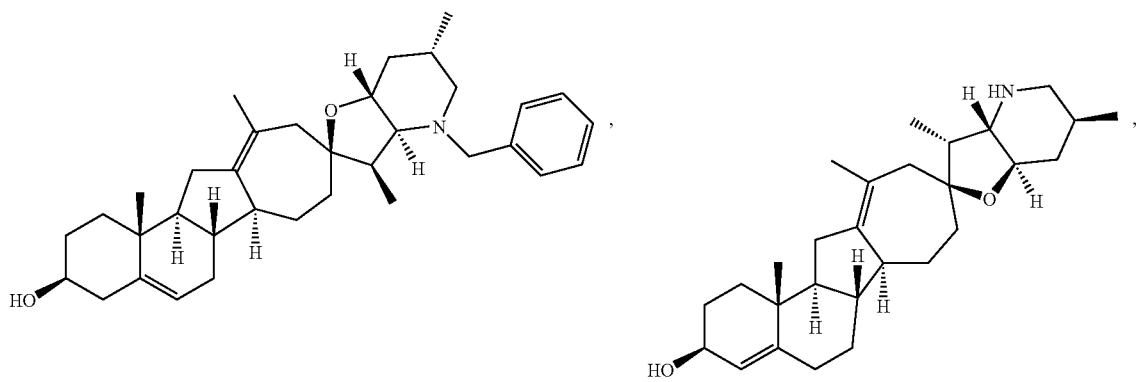
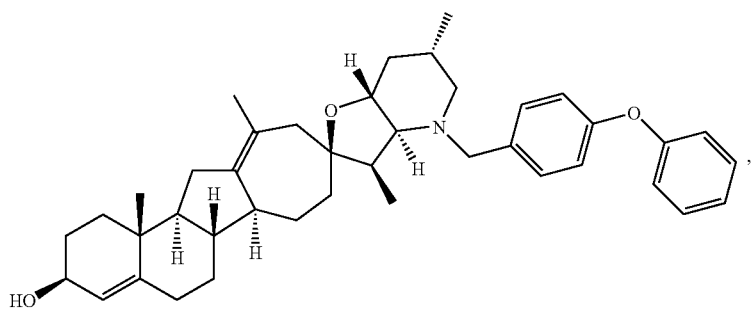
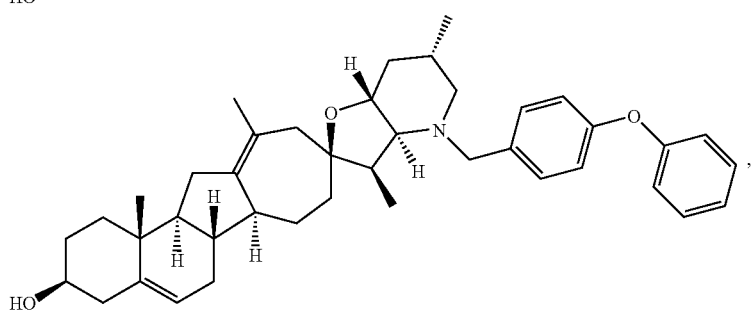
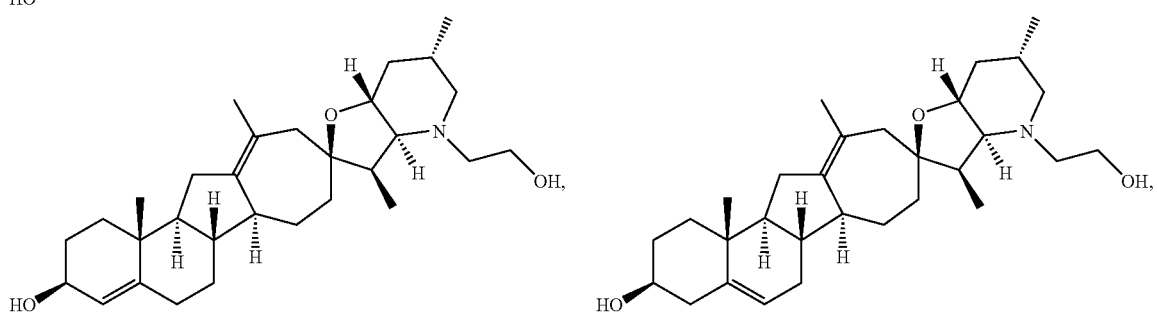

-continued
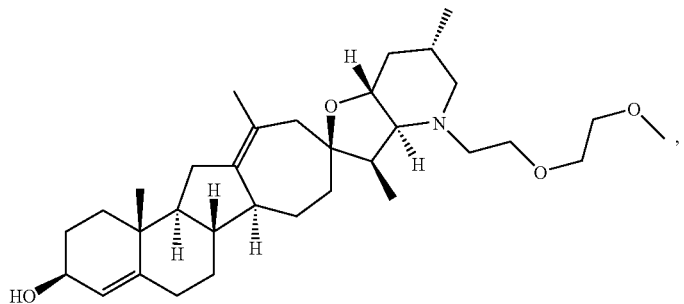
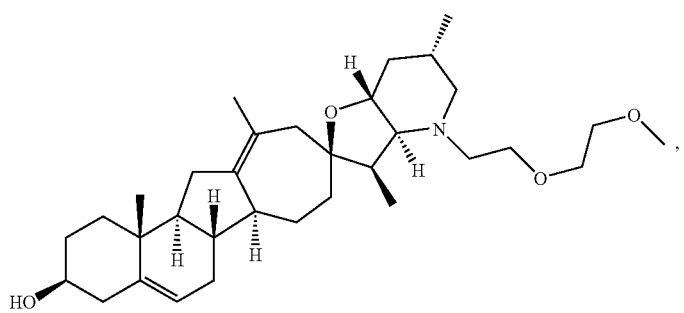
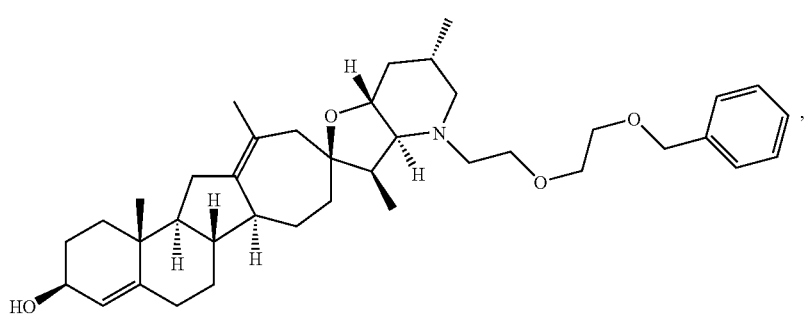
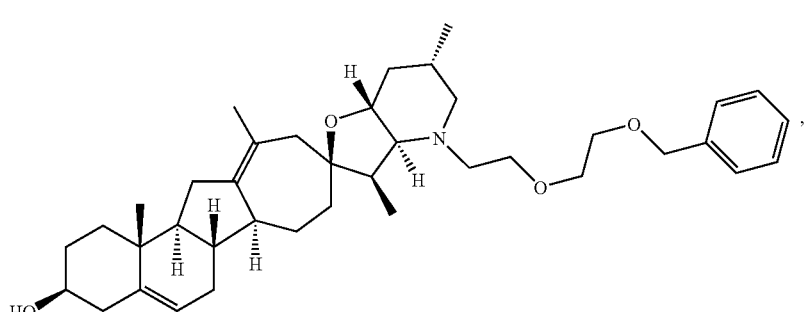
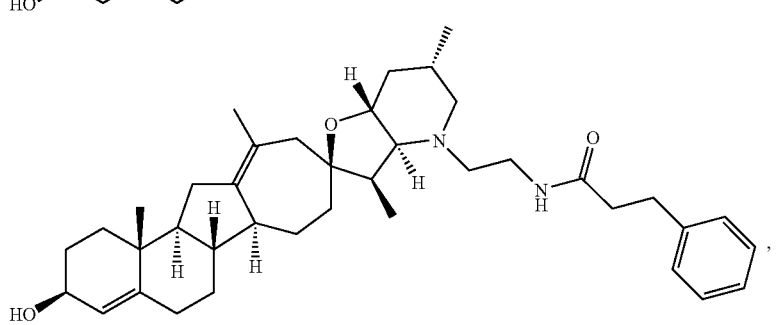

-continued
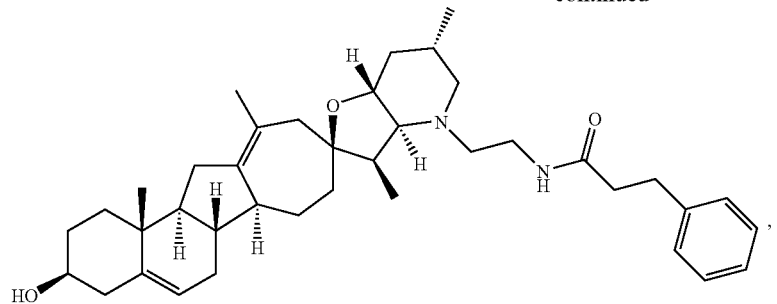,
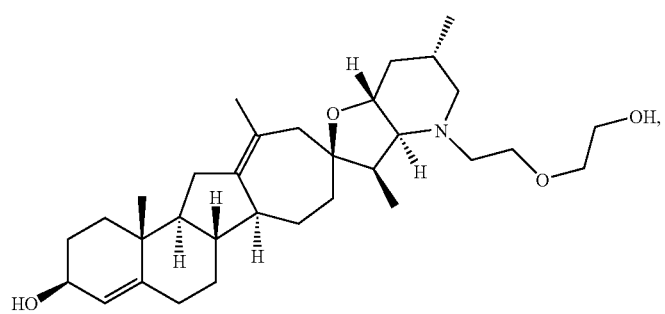
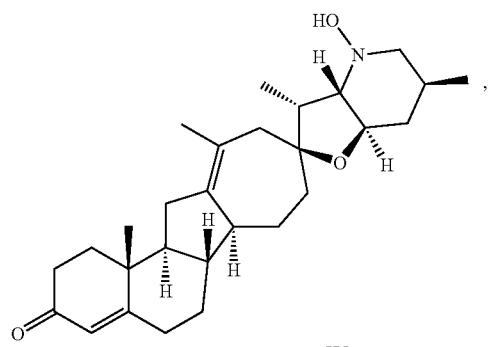, 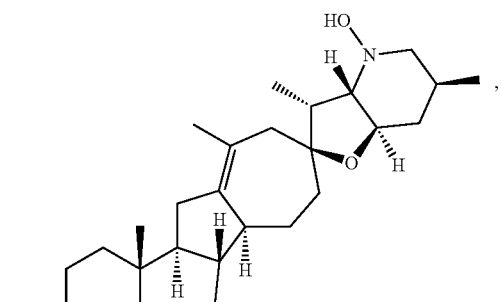
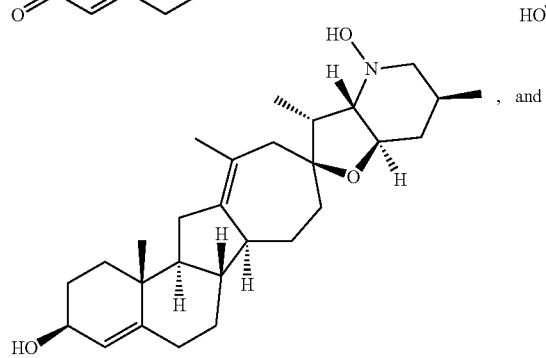, and
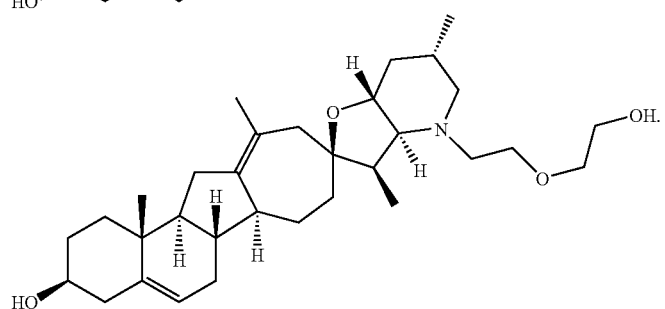

19. The compound of claim 1, which has the formula:

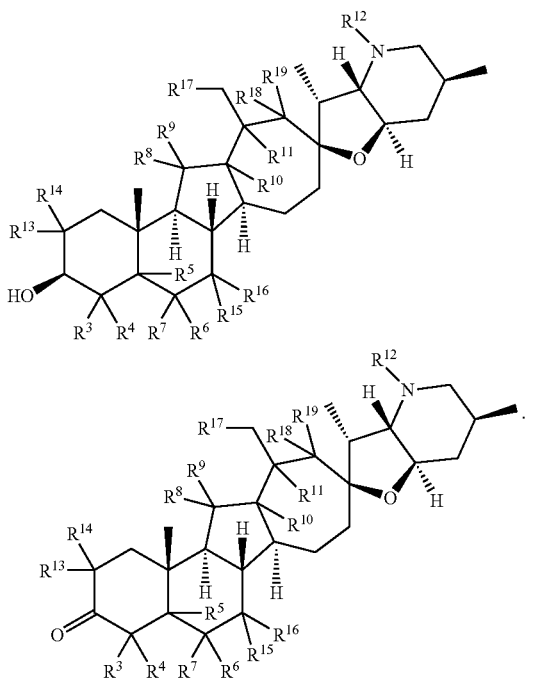

or

20. A compound of Formula 2:

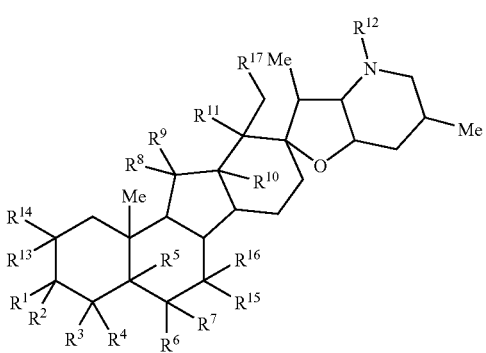

or a pharmaceutically acceptable salt thereof;
wherein each $R^1$ and $R^8$ is independently H, alkyl, alkenyl, alkynyl, aryl, cycloalkyl, heterocycloalkyl, aralkyl, heteroaryl, heteroaralkyl, halide, sulfhydryl, alkylthio, arylthio, aralkylthio, hydroxyl, alkoxyl, aryloxy, acyloxy, amino, alkylamino, arylamino, acylamino, aralkylamino, nitro, acylthio, carboxamide, sulfonamide, sulfate, —OP(L)($OR^{21}$)$_2$, —X—C(L)—$R^{21}$ or —X—C(L)—X—$R^{21}$;
wherein $R^1$ may also be a sugar;
each X is independently O or NR wherein R is H, alkyl, alkenyl, alkynyl, aryl, cycloalkyl or aralkyl;
L is O or S;
$R^2$ and $R^9$ are independently H, alkyl, alkenyl, alkynyl, aryl, cycloalkyl, heterocycloalkyl, nitrile, aralkyl, alkoxyl, aryloxy, acyloxy, carboxyl, halide, sulfhydryl, alkylthio, arylthio, aralkylthio, hydroxyl, amino, alkylamino, arylamino, acylamino, aralkylamino, heteroaryl, or heteroaralkyl;

each $R^5$ and $R^{11}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, alkylseleno, aralkylseleno, arylseleno, alkylthio, aralkylthio, arylthio, heteroaryl, or heteroaralkyl;
each $R^3$, $R^4$, $R^6$, $R^7$, $R^{13}$ and $R^{14}$ is independently H, alkyl, alkenyl, alkynyl, aryl, cycloalkyl, heterocycloalkyl, aralkyl, alkoxyl, aryloxy, acyloxy, halide, hydroxyl, amino, alkylamino, arylamino, acylamino, aralkylamino, heteroaryl, or heteroaralkyl;
or $R^1$ and $R^2$ taken together and/or $R^8$ and $R^9$ taken together, along with the carbon to which they are bonded, form —(C=O)—, —(C=S)—, —(C=N($OR^{20}$))—, —(C=N($R^{20}$))—, —(C=N(N($R^{20}$) ($R^{20}$)))—, or form an optionally substituted 3–8 membered ring containing up to two heteroatoms selected from N, O, and S; or
$R^4$ and $R^5$ taken together and/or $R^5$ and $R^6$ taken together and/or $R^{10}$ and $R^{11}$ taken together form a double bond or form a group represented by 1b

 (1b)

wherein Z is $NR^{21}$, or $C(R^{23})(R^{23})$;
$R^{12}$ is H, alkyl, alkenyl, alkynyl, aryl, cycloalkyl, heterocycloalkyl, hydroxyl, aralkyl, heteroaryl, heteroaralkyl, haloalkyl, alkoxyl, —C(O)$R^{21}$, —CO$_2R^{21}$, —SO$_2R^{21}$, —C(O)N($R^{21}$)($R^{21}$), —[C($R^{21}$)$_2$]$_q$—$R^{21}$, —[(W)—N($R^{21}$)C(O)]$_q R^{21}$, —[(W)—C(O)]$_q R^{21}$, —[(W)—C(O)O]$_q R^{21}$, —[(W)—OC(O)]$_q R^{21}$, —[(W)—SO$_2$]$_q R^{21}$, —[(W)—N($R^{21}$)SO$_2$]$_q R^{21}$, —[(W)—C(O)N($R^{21}$)]$_q R^{21}$, —[(W)—O]$_q R^{21}$, —[(W)—N($R^{21}$)]$_q R^{21}$, or —[(W)—S]$_q R^{21}$;
wherein each W is independently a diradical, and q is 1, 2, 3, 4, 5, or 6;
$R^{15}$, $R^{16}$, and $R^{17}$ are independently H, alkoxyl, aryloxy, acyloxy, halide, hydroxyl, amino, alkylamino, arylamino, acylamino, aralkylamino; or $R^{15}$ and $R^{16}$ taken together, along with the carbon to which they are bonded, form —C(O)— or —C(S)—;
$R^{18}$ and $R^{19}$ are independently H, alkyl, araalkyl, halide, amido, or ester;
each $R^{20}$ is independently H, alkyl, alkenyl, alkynyl, aryl, cycloalkyl, heterocycloalkyl, aralkyl, heteroaryl, or heteroaralkyl; or any two occurrences of $R^{20}$ on the same substituent can be taken together to form a 4–8 membered optionally substituted ring;
each $R^{21}$ is independently H, alkyl, alkenyl, alkynyl, aryl, cycloalkyl, heterocycloalkyl, aralkyl, heteroaryl, heteroaralkyl or —[C($R^{20}$)$_2$]$_p$—$R^{25}$ wherein p is 0–6; or any two occurrences of $R^{21}$ on the same substituent can be taken together to form a 4–8 membered optionally substituted ring which contains up two heteroatoms selected from N, O, S, and P;
each $R^{23}$ is independently H, alkyl, alkenyl, alkynyl, aryl, cycloalkyl, heterocycloalkyl, aralkyl, heteroaryl, heteroaralkyl, halide, alkoxyl, aryloxy, acyloxy, silyloxy, nitrile, —C(O)$R^{21}$, —CO$_2R^{21}$, —SO$_2R^{21}$, and —C(O)N($R^{21}$)$_2$;
each $R^{25}$ is independently H, hydroxyl, acylamino, —N($R^{20}$)COR$^{20}$, —N($R^{20}$)C(O)OR$^{20}$, —N($R^{20}$)S$_2$ ($R^{20}$), —COR$^{20}$N(R$^{20}$)$_2$, —OC(O)R$^{20}$N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^{20}$, —S(O)$_2$OR$^{20}$, —OP(L)(OR$^{20}$)(OR$^{20}$), —NP(O)(OR$^{20}$)(OR$^{20}$), or —P(O)(OR$^{20}$)(OR$^{20}$).

provided that there is at least one group represented by formula 1b on said compound of formula 2.

21. The compound of claim 20, wherein R$^{13}$, R$^{14}$, R$^{15}$, R$^{16}$, and R$^{17}$ are hydrogen.

22. The compound of claim 20, wherein R$^1$ is hydroxyl, sugar, —OP(L)(OR$^{20}$)$_2$, —X—C(L)-R$^{21}$, or —X—C(L)—X—R$^{21}$; or R$^1$ and R$^2$ taken together, along with the carbon to which they are bonded, form —C(O)—.

23. The compound of claim 20, wherein R$^4$ and R$^5$ taken together form a double bond.

24. The compound of claim 23, wherein R$^1$ and R$^2$ taken together, along with the carbon to which they are bonded, form —C(O)—.

25. The compound of claim 20, wherein R$^1$ is hydroxyl and R$^2$ is H.

26. The compound of claim 25, wherein R$^5$ and R$^6$ taken together form a double bond; or R$^5$ and R$^6$ taken together form a group represented by 1b;

(1b)

wherein:
Z is C(R$^{23}$)(R$^{23}$).

27. The compound of claim 20, wherein R$^{10}$ and R$^{11}$ taken together form a double bond; or R$^{10}$ and R$^{11}$ taken together form a group represented by 1b;

(1b)

wherein:
Z is C(R$^{23}$)(R$^{23}$).

28. The compound of claim 20, wherein R$^5$ and R$^6$ taken together and R$^{10}$ and R$^{11}$ taken together form a group represented by 1b;

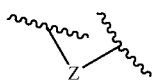
(1b)

wherein:
Z is C(R$^{23}$)(R$^{23}$).

29. The compound of claim 24, wherein R$^{10}$ and R$^{11}$ taken together form a double bond; or R$^{10}$ and R$^{11}$ taken together form a group represented by 1b;

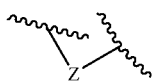
(1b)

wherein:
Z is C(R$^{23}$)(R$^{23}$).

30. The compound of claim 25, wherein R$^{10}$ and R$^{11}$ taken together form a double bond; or R$^{10}$ and R$^{11}$ taken together form a group represented by 1b;

(1b)

wherein:
Z is C(R$^{23}$)(R$^{23}$).

31. The compound of claim 20, wherein R$^8$ and R$^9$ are hydrogen; or R$^8$ and R$^9$ taken together, along with the carbon to which they are bonded, is —C(O)—.

32. The compound of claim 20, wherein R$^{12}$ is H, alkyl, cycloalkyl, aralkyl, heteroaryl, heteroaralkyl, haloalkyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

33. The compound of claim 21, wherein R$^{12}$ is H, alkyl, cycloalkyl, aralkyl, heteroaryl, heteroaralkyl, haloalkyl, hydroxyl, alkoxyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

34. The compound of claim 24, wherein R$^{12}$ is H, alkyl, cycloalkyl, aralkyl, heteroaryl, heteroaralkyl, haloalkyl, hydroxyl, alkoxyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

35. The compound of claim 25, wherein R$^{12}$ is H, alkyl, cycloalkyl, aralkyl, heteroaryl, heteroaralkyl, haloalkyl, hydroxyl, alkoxyl, —[(W)—N(R$^{21}$)C(O)]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—C(O)]$_q$R$^{21}$, or —[(W)—C(O)O]$_q$R$^{21}$.

36. A compound of the formula:

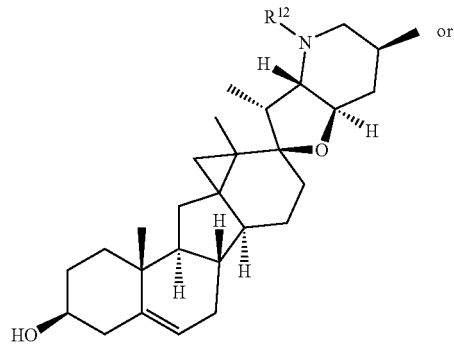
or
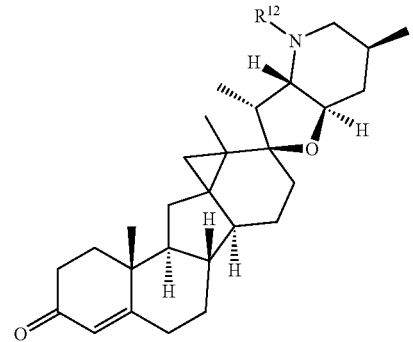

wherein:

R$^{12}$ is H, alkyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), —[C(R$^{21}$)$_2$]$_p$—R$^{21}$, —[(W)—N(R$^{21}$)C(O)]$_q$R$^{21}$, —[(W)—C(O)]$_q$R$^{21}$, —[(W)—C(O)O]$_q$R$^{21}$, —[(W)—OC(O)]$_q$R$^{21}$, —[(W)—SO$_2$]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—N(R$^{21}$)]$_q$R$^{21}$, or —[(W)—S]$_q$R$^{21}$;

q is 1, 2, 3, 4, 5, or 6;

each R$^{20}$ is independently H, alkyl, alkenyl, alkynyl, aryl, cycloalkyl, heterocycloalkyl, aralkyl, heteroaryl, or heteroaralkyl; or any two occurrences of R$^{20}$ on the same substituent can be taken together to form a 4–8 membered optionally substituted ring containing 0–3 heteroatoms selected from O, N, S, and P;

each R$^{21}$ is independently H, alkyl, aryl, cycloalkyl, heterocycloalkyl, aralkyl, heteroaryl, heteroaralkyl or —[C(R$^{20}$)$_2$]$_p$—R$^{25}$ wherein p is 0–6; or any two occurrences of R$^{21}$ on the same substituent can be taken together to form a 4–8 membered optionally substituted ring containing 0–3 heteroatoms selected from O, N, S, and P;

each R$^{25}$ is independently H, hydroxyl, acylamino, —N(R$^{20}$)COR$^{20}$, —N(R$^{20}$)C(O)OR$^{20}$, —N(R$^{20}$)SO$_2$(R$^{20}$), —COR$^{20}$N(R$^{20}$)$_2$, —OC(O)R$^{20}$N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^{19}$, —S(O)$_2$OR$^{20}$, —OP(O)(OR$^{20}$)(OR$^{20}$), —NP(O)(OR$^{20}$)(OR$^{20}$), or —P(O)(OR$^{20}$)(OR$^{20}$).

37. A compound selected from the group consisting of:

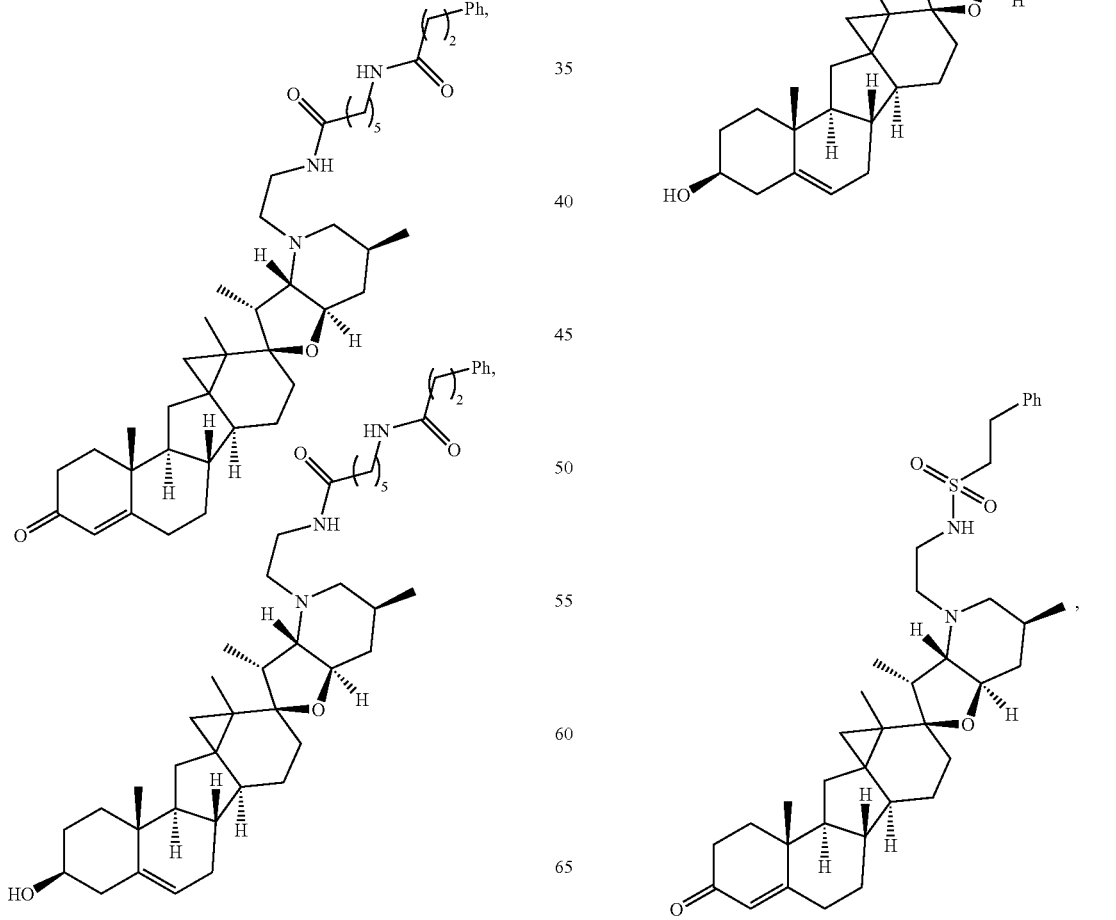

-continued
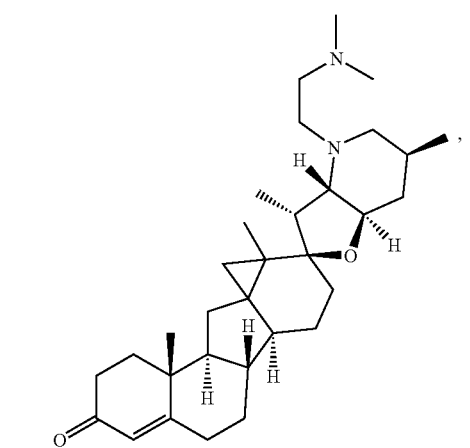
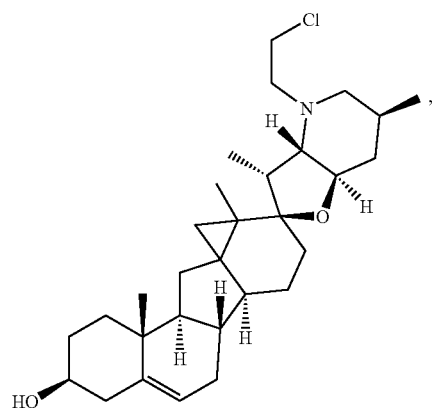
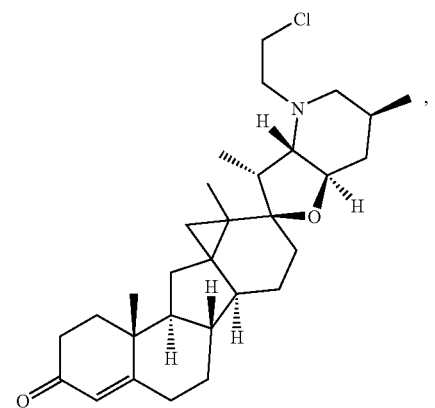
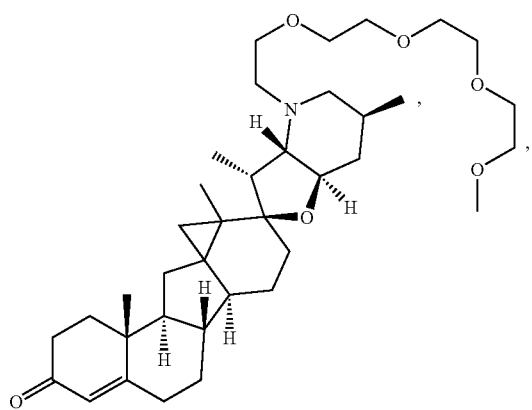
-continued
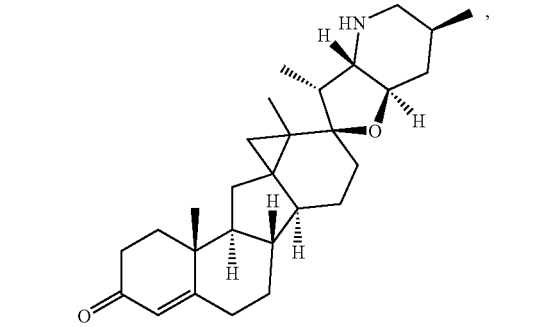
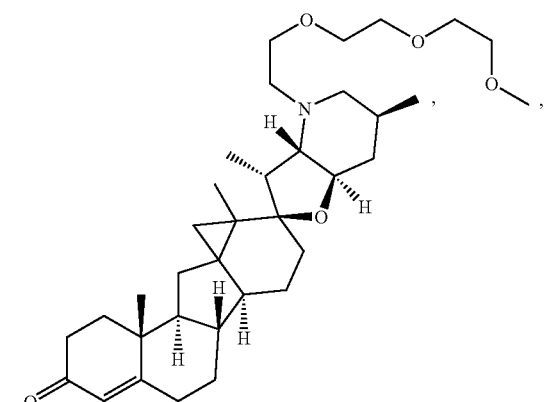
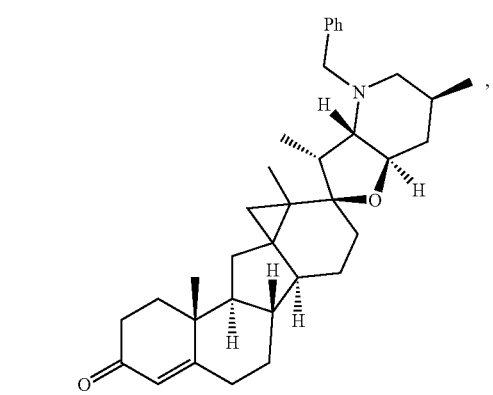
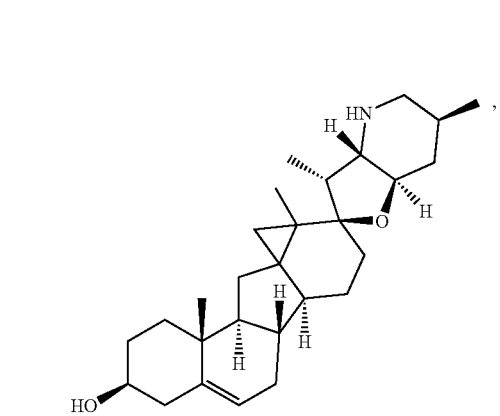

141
-continued
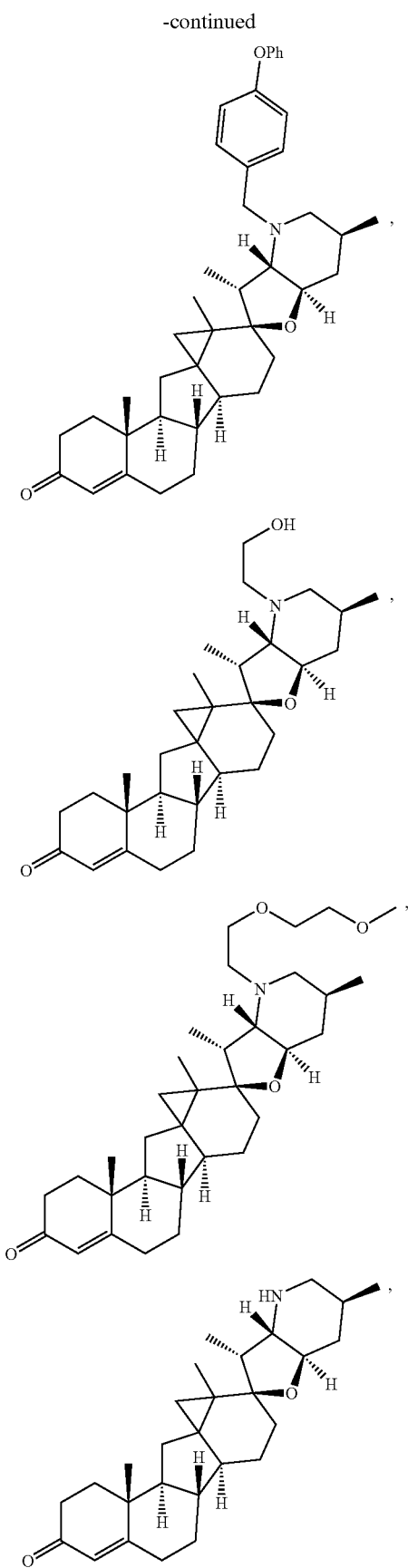
142
-continued
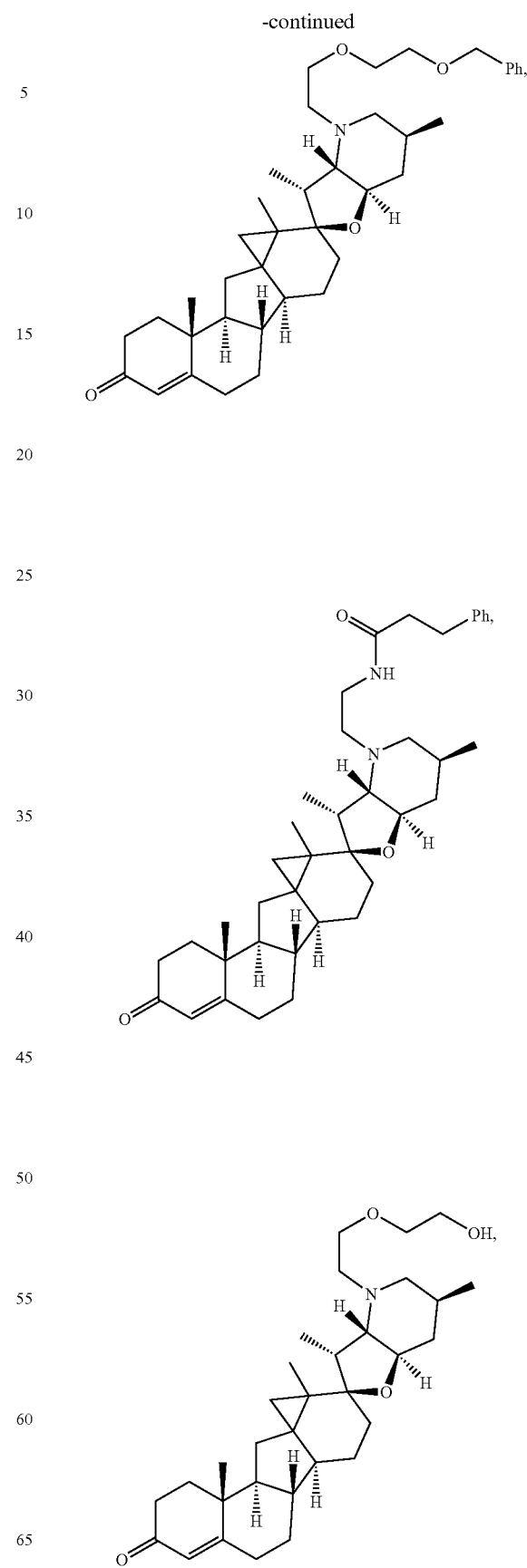

143
-continued
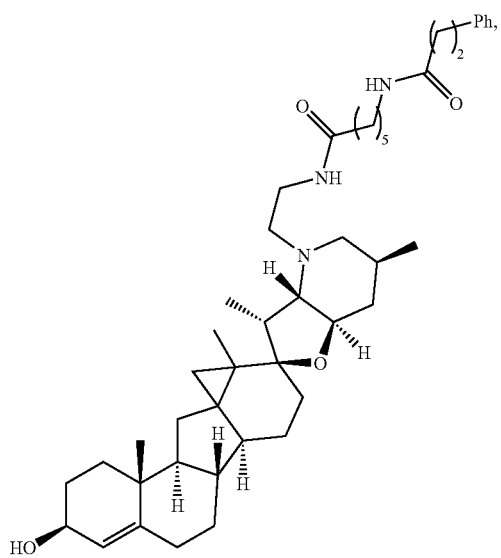
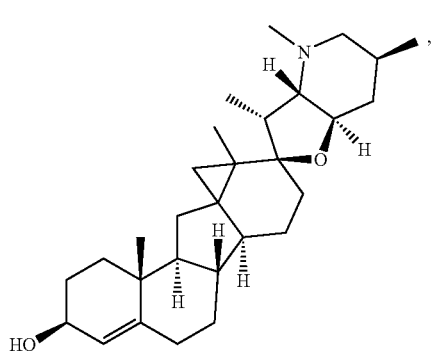
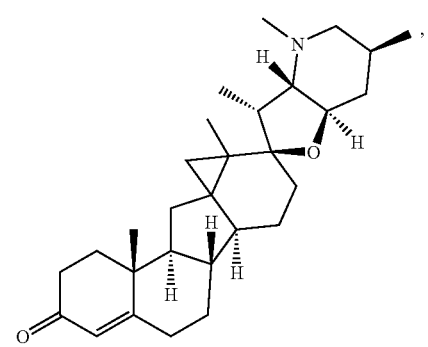
144
-continued
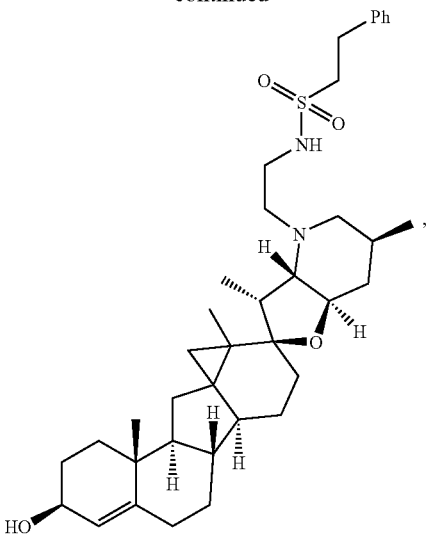
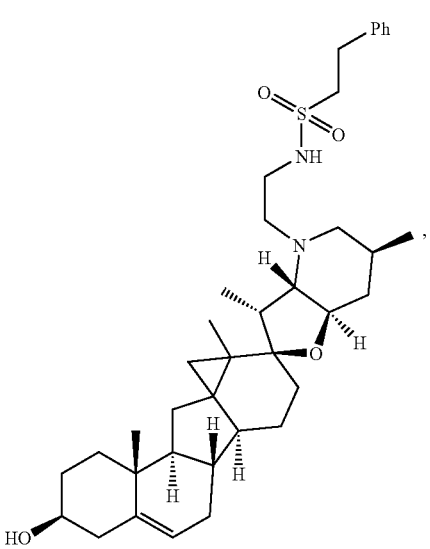
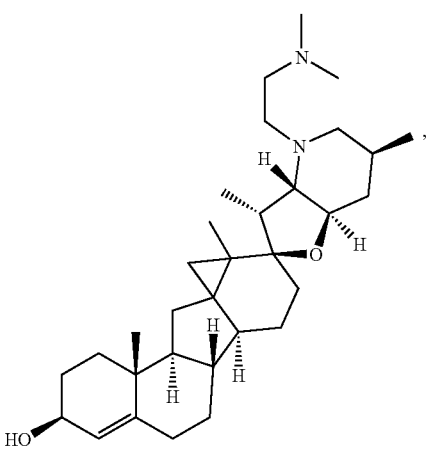

-continued
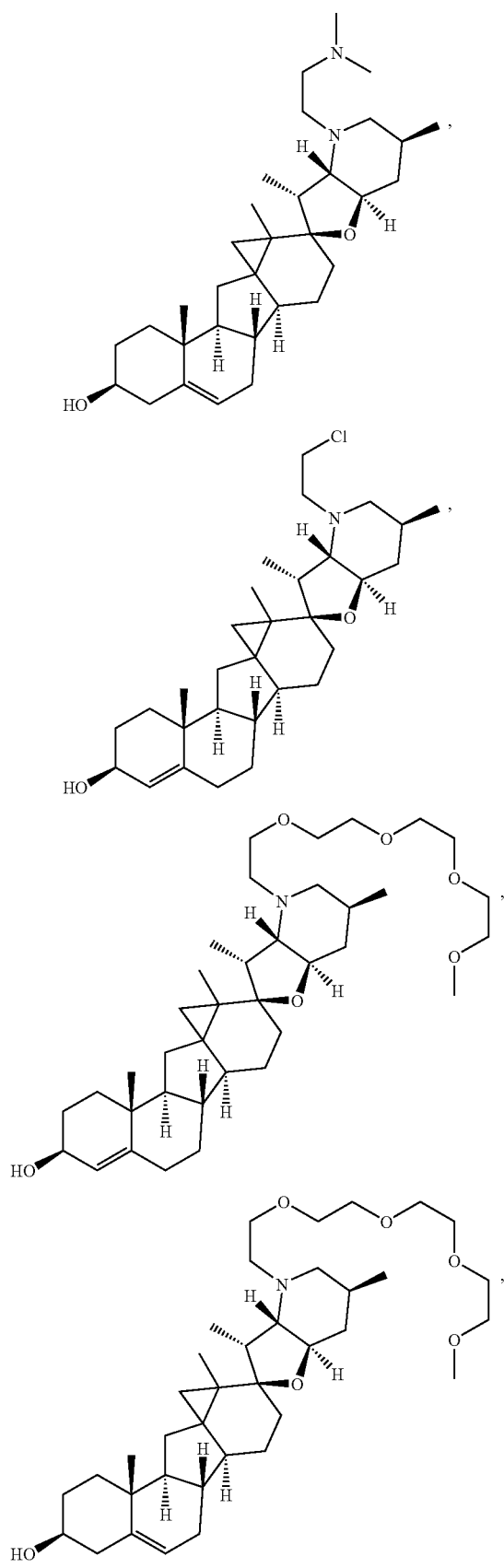
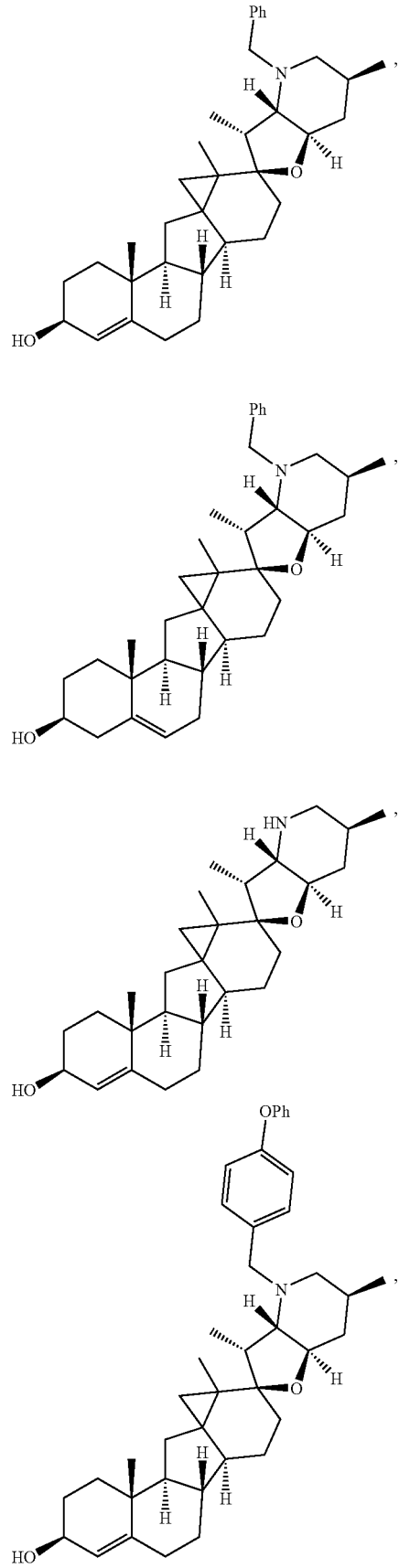

-continued
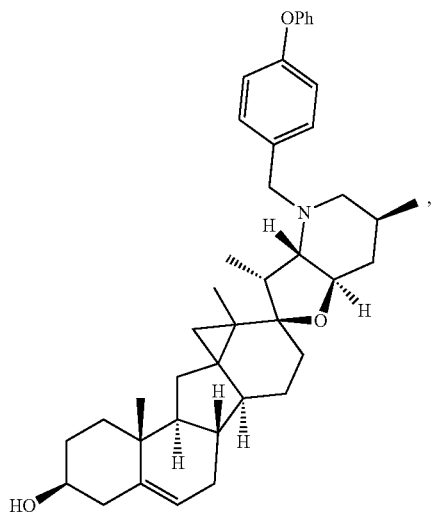
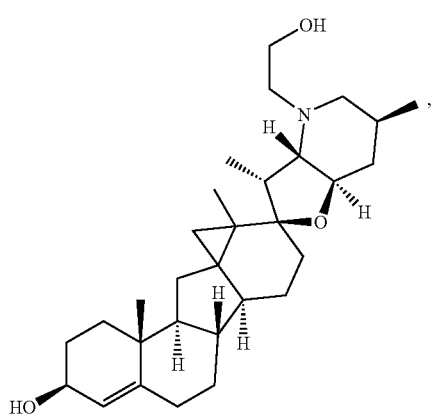
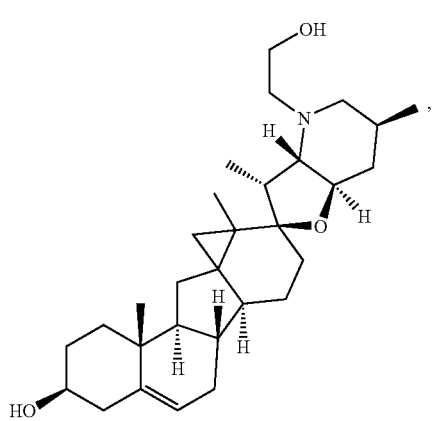
-continued
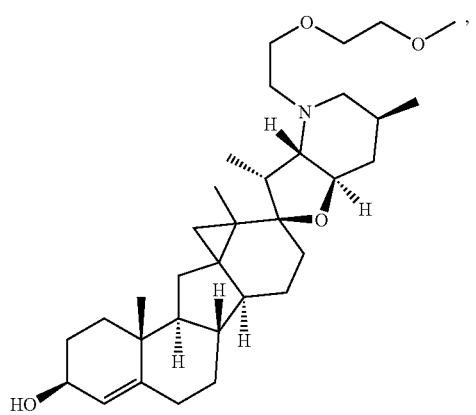
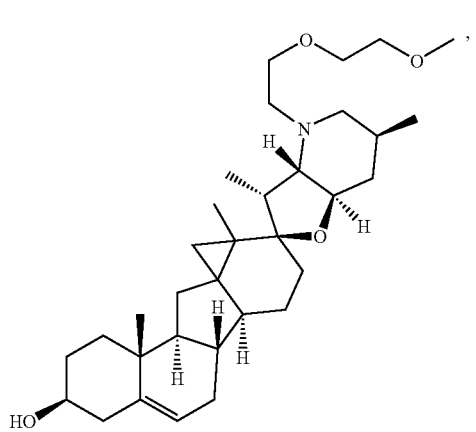
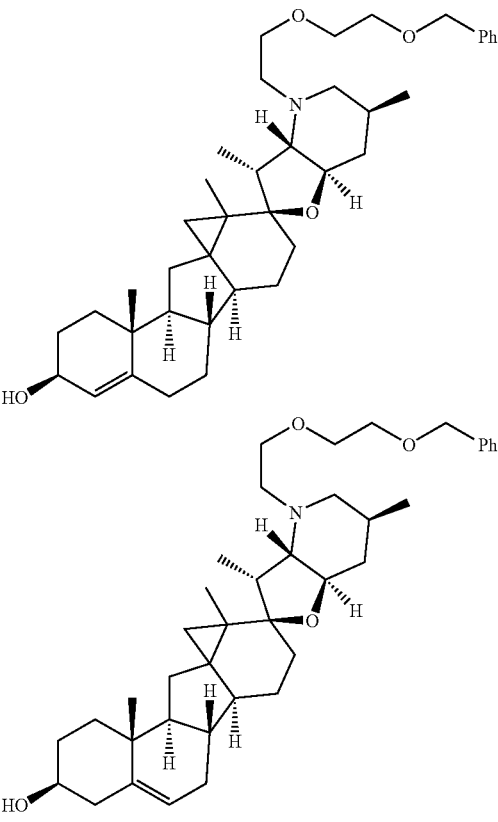

-continued
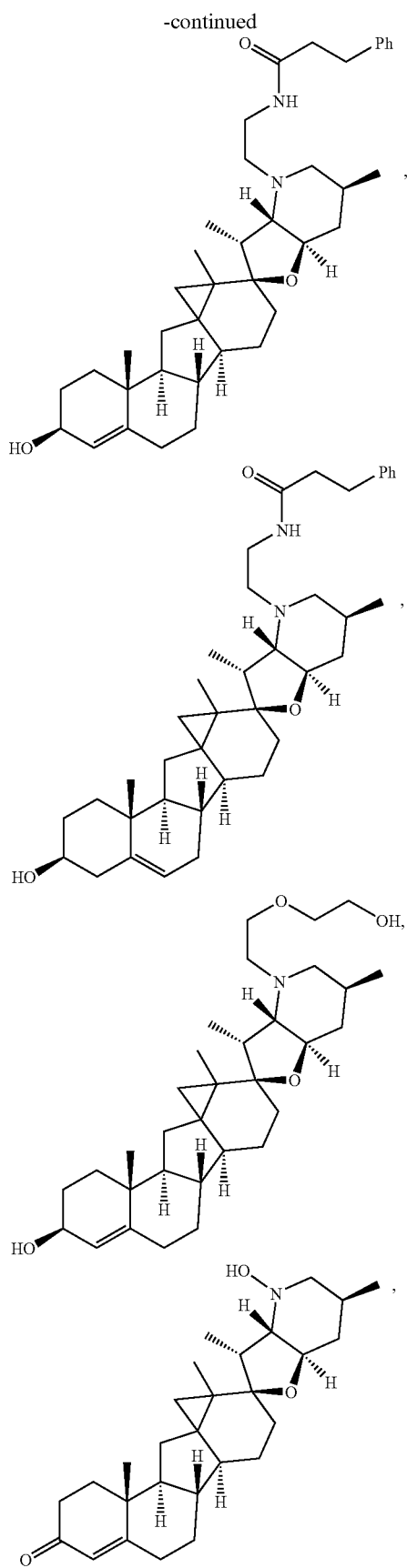
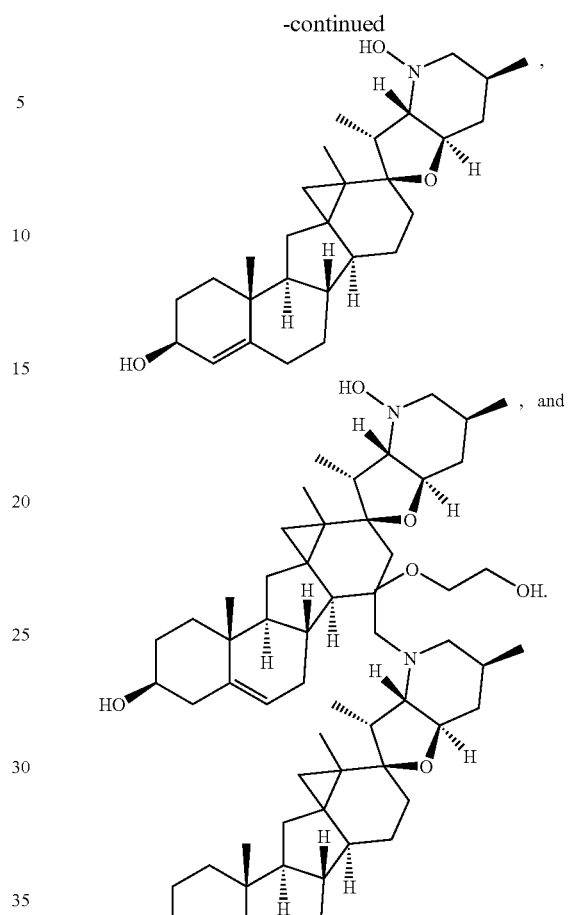
38. The compound of claim 20, which has the formula:
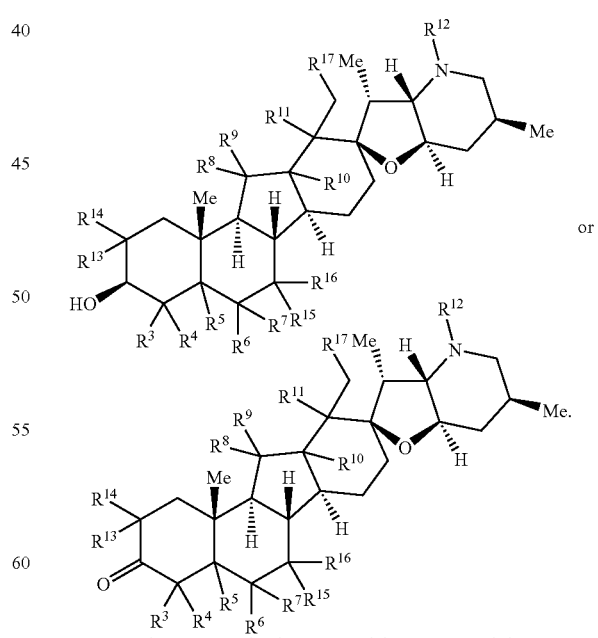
39. A pharmaceutical composition, comprising a compound of claim 1; and a pharmaceutically acceptable excipient.
* * * * *

UNITED STATES PATENT AND TRADEMARK OFFICE
CERTIFICATE OF CORRECTION

PATENT NO. : 7,230,004 B2
APPLICATION NO. : 11/213534
DATED : June 12, 2007
INVENTOR(S) : Julian Adams et al.

It is certified that error appears in the above-identified patent and that said Letters Patent is hereby corrected as shown below:

At column 133, line 31 through column 150, line 62, claims 20-38 should be deleted.

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,230,004 B2  Page 1 of 1
APPLICATION NO. : 11/213534
DATED : June 12, 2007
INVENTOR(S) : Julian Adams et al.

It is certified that error appears in the above-identified patent and that said Letters Patent is hereby corrected as shown below:

Column 8, the formula spanning line 5 to about line 8; that portion of the formula reading "-OR56" should read -- -R56 --.

Signed and Sealed this

Twenty-fourth Day of August, 2010

David J. Kappos
*Director of the United States Patent and Trademark Office*